US010918288B2

(12) United States Patent
Torres

(10) Patent No.: US 10,918,288 B2
(45) Date of Patent: Feb. 16, 2021

(54) SYSTEMS AND METHODS FOR TRACKING NEURO-DEVELOPMENT DISORDERS

(71) Applicant: RUTGERS, THE STATE UNIVERSITY OF NEW JERSEY, New Brunswick, NJ (US)

(72) Inventor: Elizabeth B. Torres, Piscataway, NJ (US)

(73) Assignee: RUTGERS, THE STATE UNIVERSITY OF NEW JERSEY, Brunswick, NJ (US)

( * ) Notice: Subject to any disclaimer, the term of this patent is extended or adjusted under 35 U.S.C. 154(b) by 0 days.

(21) Appl. No.: 16/342,170

(22) PCT Filed: Oct. 16, 2017

(86) PCT No.: PCT/US2017/056779
§ 371 (c)(1),
(2) Date: Apr. 15, 2019

(87) PCT Pub. No.: WO2018/071900
PCT Pub. Date: Apr. 19, 2018

(65) Prior Publication Data
US 2019/0254533 A1    Aug. 22, 2019

Related U.S. Application Data

(60) Provisional application No. 62/408,542, filed on Oct. 14, 2016.

(51) Int. Cl.
*A61B 5/0205*    (2006.01)
*A61B 5/00*    (2006.01)
(Continued)

(52) U.S. Cl.
CPC .............. *A61B 5/0205* (2013.01); *A61B 5/00* (2013.01); *A61B 5/0022* (2013.01); *A61B 5/02* (2013.01);
(Continued)

(58) Field of Classification Search
CPC ......... A61B 5/02; A61B 5/0205; A61B 5/024; A61B 5/02405; A61B 5/0245; A61B 5/04;
(Continued)

(56) References Cited

U.S. PATENT DOCUMENTS 5,454,376 A    10/1995   Stephens
5,747,266 A    5/1998    Beach
(Continued)

FOREIGN PATENT DOCUMENTS

WO    2016/094375 A1    6/2016

OTHER PUBLICATIONS

International Search Report in corresponding PCT/US2017/056779, dated Feb. 9, 2018.
(Continued)

*Primary Examiner* — Ahmed M Farah
(74) *Attorney, Agent, or Firm* — Wolter Van Dyke Davis, PLLC; Eugene J. Molinelli

(57) ABSTRACT

A system captures a baby's physical characteristics taken on two or more specified days since birth and sensor input from a device capturing a rhythm produced by the baby's nervous system on at least each of those two or more specified days since birth, and identify whether the baby is at risk for neuro-developmental issues. The system may estimate stochastic trajectories for each day's sensor data and, from the stochastic trajectories, determine a maximum shift amplitude and percentage of transitions within and between regions of a Gamma plane. The system may plot the change
(Continued)

in maximum shift amplitudes over successive days against the change in physical characteristics over those successive days, and perform a linear fit for the plot to track the neuro-development and identify risk of issues for the baby.

19 Claims, 41 Drawing Sheets

(51) Int. Cl.
    *A61B 5/04*         (2006.01)
    *A61B 5/107*      (2006.01)
    *A61B 5/02*         (2006.01)
    *G16H 40/67*      (2018.01)
    *A61B 5/08*         (2006.01)

(52) U.S. Cl.
    CPC ............ *A61B 5/04* (2013.01); *A61B 5/04012* (2013.01); *A61B 5/107* (2013.01); *A61B 5/7275* (2013.01); *A61B 5/08* (2013.01); *A61B 5/6801* (2013.01); *A61B 2503/04* (2013.01); *G16H 40/67* (2018.01)

(58) Field of Classification Search
    CPC ............ A61B 5/04001; A61B 5/04011; A61B 5/04012; A61B 5/04014; A61B 5/04017; A61B 5/0432; A61B 5/04325; A61B 5/053; A61B 5/0531; A61B 5/08; A61B 5/0803; A61B 5/107; A61B 5/1072; A61B 5/68; A61B 5/6801; A61B 5/6802; A61B 5/6813; A61B 5/683; A61B 5/6879; A61B 5/72; A61B 2503/00; A61B 2503/02; A61B 2503/04; A61B 2503/045; A61B 2503/06; A61B 2503/08; A61B 2503/012
    USPC ....... 600/301, 508, 511–516, 529, 544, 547; 128/898
See application file for complete search history.

(56) References Cited

U.S. PATENT DOCUMENTS

| | | | | |
|---|---|---|---|---|
| 6,454,729 | B1* | 9/2002 | Jacobs | G16H 50/50 600/587 |
| 8,563,610 | B2* | 10/2013 | Stein | A61K 31/202 514/560 |
| 2003/0068605 | A1* | 4/2003 | Kullok | G09B 23/28 434/258 |
| 2004/0030258 | A1 | 2/2004 | Williams et al. | |
| 2007/0066915 | A1* | 3/2007 | Frei | A61B 5/048 600/544 |
| 2011/0289606 | A1* | 11/2011 | Allen | A61K 39/245 800/8 |
| 2012/0108998 | A1 | 5/2012 | Molnar et al. | |
| 2013/0178731 | A1* | 7/2013 | Bosl | A61B 5/0476 600/409 |
| 2014/0336539 | A1 | 11/2014 | Torres et al. | |

OTHER PUBLICATIONS

Wang et al., "Power spectral density and coherence analysis of Alzheimer's EEG," Cognitive Neurodynamics, Dec. 16, 2014, vol. 9, p. 293, cols. 1-2, p. 294, col. 2, p. 296, col. 301, col. 1, p. 302, col. 2.

Sturman et al., "Deep brain stimulation and medication for Parkinsonian tremor during secondary tasks," Movement Disorders, vol. 8, pp. 1157-1163.

Barlow and Estep, Central pattern generation and the motor infrastructure for suck, respiration, and speech. J Commun Disord, 2006, pp. 366-380, vol. 39.

Box and Cox, An analyses of transformations, Journal of the Royal Statistical Society Series B, 1964, pp. 211-252, vol. 26.

Craig, C. et al., Detecting Motor Abnormalities in Preterm Infants, Experimental Brain Research, 2000, pp. 359-365, vol. 131(3).

Forkman, J., Estimator and Tests for Common Coefficients of Variation in Normal Distributions. Communications in statistics, Theory and Methods, 2009, pp. 233-251, vol. 38(2).

Singh, A. et al., A generalization of the Coefficient of variation with application to suppression of imprecise estimates, ASA Section on Survey Research Methods, 2004, pp. 4359-4365.

Lleonart et al., Removing Allometric Effects of Body Size in Morphological Analysis, J Theor Biol., 2000, pp. 85-93, vol. 205.

Shimazaki and Shinomoto, A Method for Selecting the Bin Size of a Time Histogram, Neural Comput, 2007, pp. 150-327, vol. 19(6).

Torres et al., Toward Precision Psychiatry: Statistical Platform for the Personalized Characterization of Natural Behaviors, Front Neurol, 2016, vol. 7, Article 8.

Extended EP Search Report in EP application No. 17860794.1 dated Feb. 13, 2020, pp. 1-9.

* cited by examiner

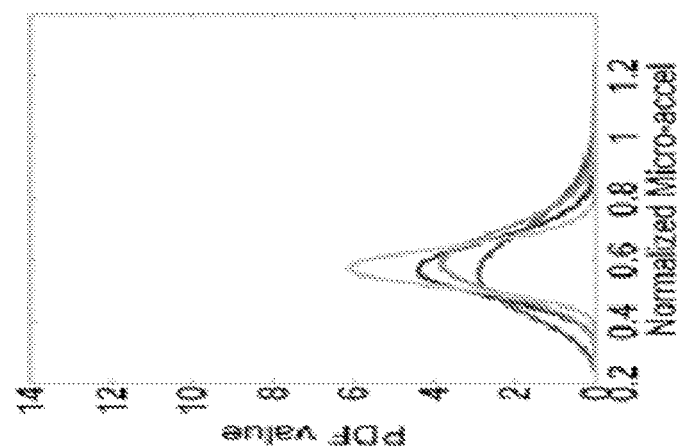
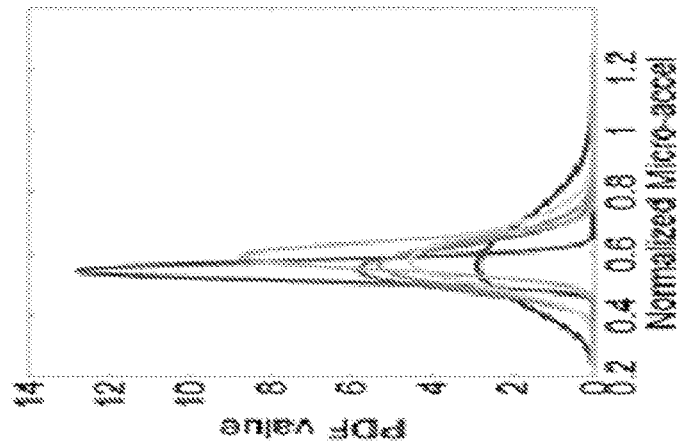
FIG. 8C
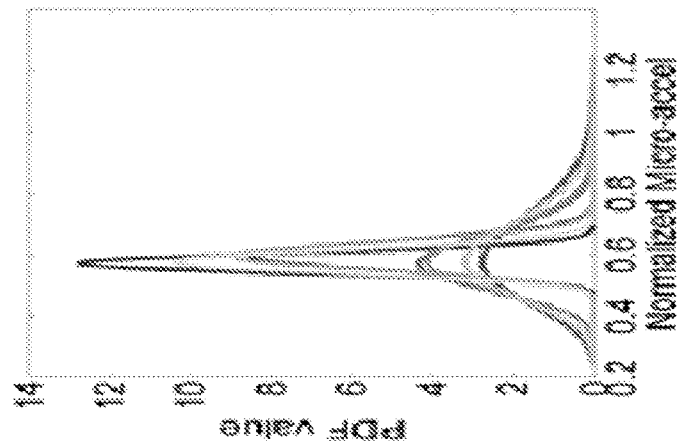

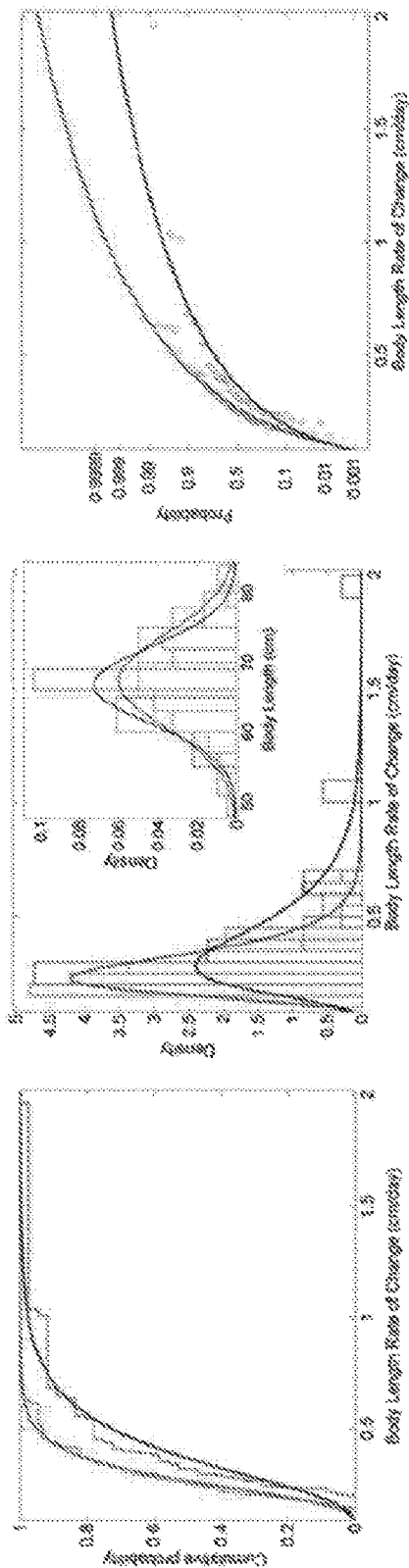
FIG. 13C
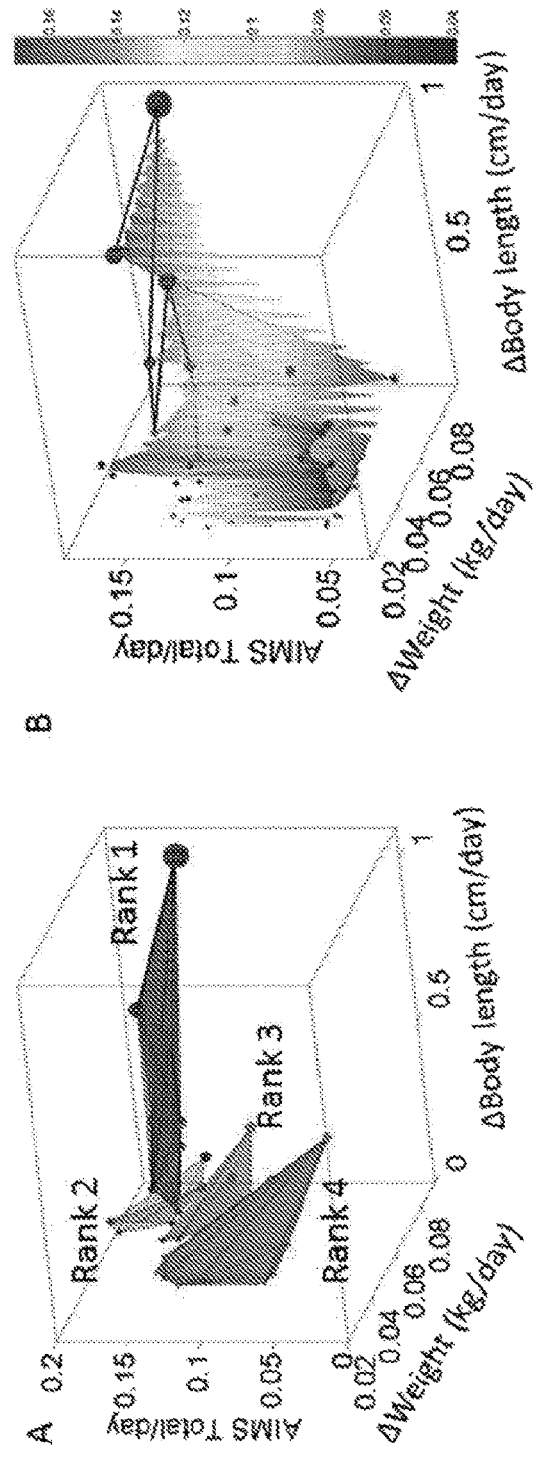
FIG. 14A
FIG. 14B

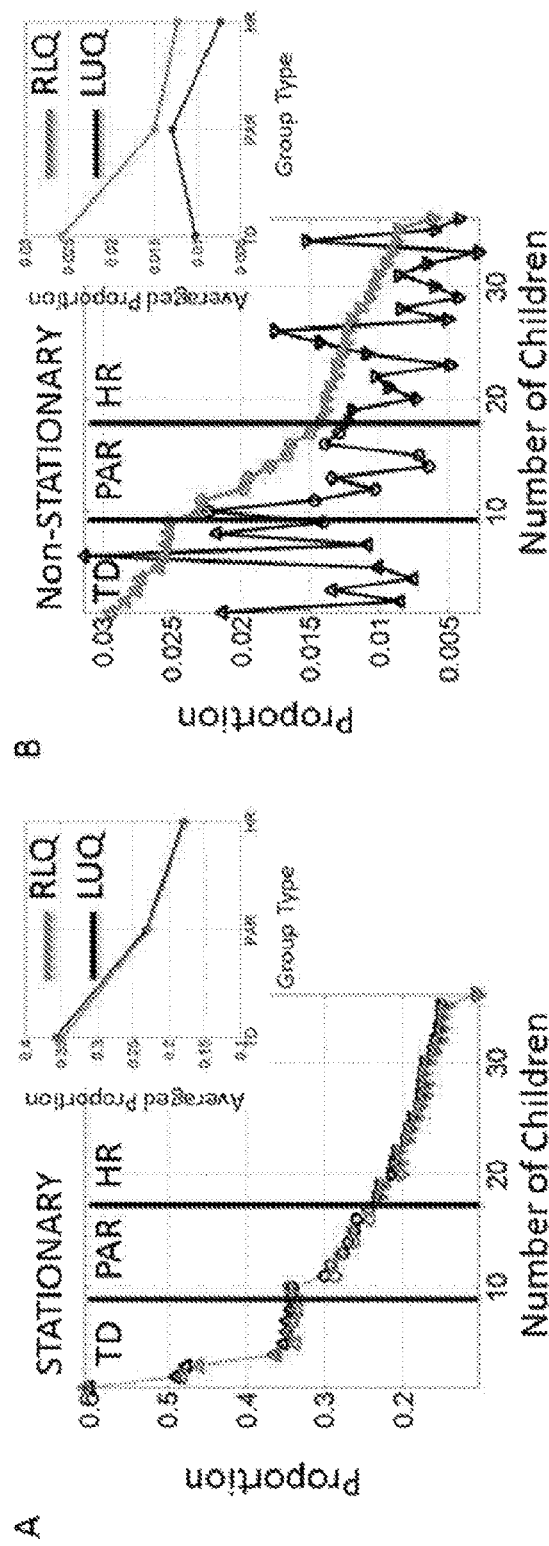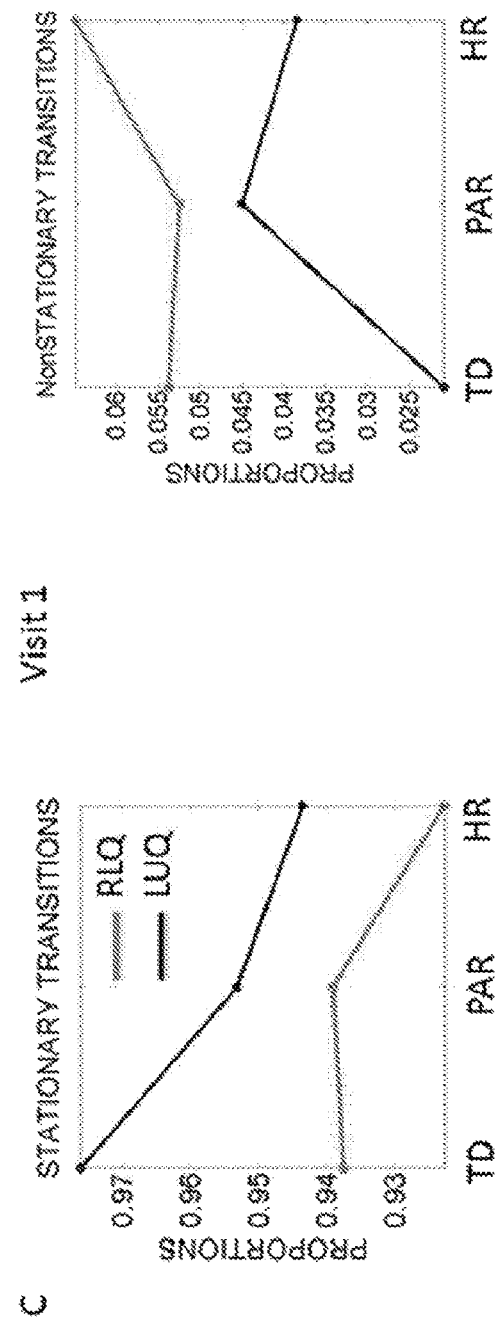
FIGs. 15A-15C

SYSTEMS AND METHODS FOR TRACKING NEURO-DEVELOPMENT DISORDERS

CROSS-REFERENCE TO RELATED APPLICATIONS

This patent document claims priority to PCT Application No. PCT/US17/56779, filed Oct. 16, 2017, which claims priority to U.S. Provisional Patent Application No. 62/408,542, filed Oct. 14, 2016 under 35 U.S.C. § 119. This Provisional U.S. Application is incorporated herein by reference in its entirety.

BACKGROUND

Neuro-development follows an extremely non-linear dynamic trajectory, with each infant experiencing a range of unique changes that may be driven by both the infant and their own environment. During the early stages of neuro-development, the infant's body and head grow at an accelerated rate and the nervous systems must rapidly develop in tandem to adapt to, and to compensate for, these changes. Due to the variable nature of biological systems, these day-to-day fluctuations in physical growth follow a non-uniform, non-linear process, with some babies changing slower than others at certain times. Likewise, the fast-changing nervous systems underlying the physical body must rapidly develop to create the foundation for purposeful controlled actions.

Traditionally the CDC and WHO growth charts reflect absolute size values informing only the size of the baby the day of the visit and the physician compares the value to a standardized table built from longitudinal data from breast-fed babies (over 26,000 babies with data openly available to researchers). Traditional methods used to build these charts impose a theoretical uniform distribution that disregards the true nature of the empirical variability in the physical growth data. As such, the standardized growth charts that pediatricians use to track the development of newborn babies tend to mask developmental abnormalities (e.g., extreme rapid growth or stunting). These abnormalities occur more infrequently and fall on the right or left tails of skewed distributions. The enforced symmetry of the distribution used to represent the percentiles of human neonatal growth imposes a type of uniformity that does not do justice to the true non-linear and non-uniform incremental nature of the rates of early physical growth. Technical problems associated with existing systems often lie in the assumption that stochastic signatures of movements of a subject are independent between each event over a time period.

There is a need to identify children at risk for neurodevelopmental disorders as early as possible to allow for early intervention with a type of therapy. This disclosure provides technical solutions in order to address the above issues and/or other issues.

SUMMARY

Systems and techniques are provided for tracking neuro-development in infants and identifying those at-risk for developmental issues.

Sensor data capturing a rhythm produced by a baby's nervous system can be collected over time. The rhythm may be produced from one or more of a movement, heartbeat, skin conductance, respiration, swallowing, and sucking. In addition to the sensor data, the incremental changes in the baby's physical characteristics of head circumference, weight, and body length can be collected for the same days as the sensor data.

A computing system—as a computing device or service platform—can receive the sensor data and the baby's incremental changes in physical characteristics to track neuro-development of the baby and identify whether the baby is at risk for a neuro-developmental issue. A process that can be carried out by the computing system may include estimating stochastic trajectories of the random fluctuations in amplitude of the rhythmic waveform (spike trains) read out from the sensor data. These spike trains represent a continuous random process studied under the general rubric of Poisson Random Process. In particular, the system may use a Gamma process to obtain a good fit of the continuous Gamma family of probability distributions. Using the empirically estimated signature of the probability distributions underlying this continuous random process, the system may determine the maximum shift amplitude of the stochastic trajectories for each day's collected sensor data. The system may determine the maximum shift amplitudes and a value indicating the corresponding day since the baby was born. The system may use the value indicating the corresponding day since the baby was born to normalize the value of the maximum shift amplitude and to register the maximum shift amplitude value with the physical characteristic data obtained from that same day. The system may similarly normalize the physical characteristics values using the corresponding number of days since the baby was born to provide increment (velocity) data providing a notion of change, rather than absolute values (size data) providing a static measurement the day of the visit. The system may also plot a change in maximum shift amplitude against a change in values of one of the physical characteristics for each time period and calculate a linear fit (coefficient of determination, $r^2$, of a linear regression) for the points. The system can use the results of the linear fit to identify whether a baby has a risk of neuro-development disorder.

In addition to determining the maximum shift amplitude, the system may determine percentages of stationary and non-stationary transitions from the stochastic trajectories of a day's collected sensor data. A single day's sensor data can be sufficient to generate a preliminary risk assessment based on the percentages of stationary and non-stationary transitions since typical development shows higher percentages of transitions than stunted or delayed development.

In some scenarios, a system for tracking neuro-development disorder under medical/age effect may include one or more wearable sensors attached to a first group of subjects belonging to an age group, and additional one or more wearable sensors attached to a second group of subjects. Each of the first and second group of subjects has a medication status, and the medication status of the first and second group of subjects are different, which allows the system to keep track the effect of medication intake. In some scenarios, the system may, for each of the first and second subject groups: capture a rhythm using the one or more wearable sensors attached to subjects; estimate trajectories of fluctuations of the first rhythm over the plurality of time periods; generate a Gamma parameter lag plane at each of the plurality of time periods; stack a plurality of Gamma parameter lag planes, each plane corresponding to a time period in sequence over the plurality of time periods; and output the stacked Gamma parameter lag planes on the display.

BRIEF DESCRIPTION OF THE DRAWINGS

FIGS. 8A-8C illustrate results of tracking of trajectories in an example.

FIGS. 13A-13C illustrate contrasting statistical differences found in physical growth data taken as absolute values vs. data taken as incremental (velocity) values representing rates of change differences since birth between the two CT and CAR groups of the example study.

FIGS. 14A-14C illustrate automatic clustering of all babies obtained from the median-ranking of the rate of change data drawn from physical growth and fluctuations in motor performance for an example case study.

FIGS. 15A-15C illustrate frequency of noise-to-signal transitions that distinguish babies at high risk from typically developing babies in an example case study.

DETAILED DESCRIPTION

Figure 1:
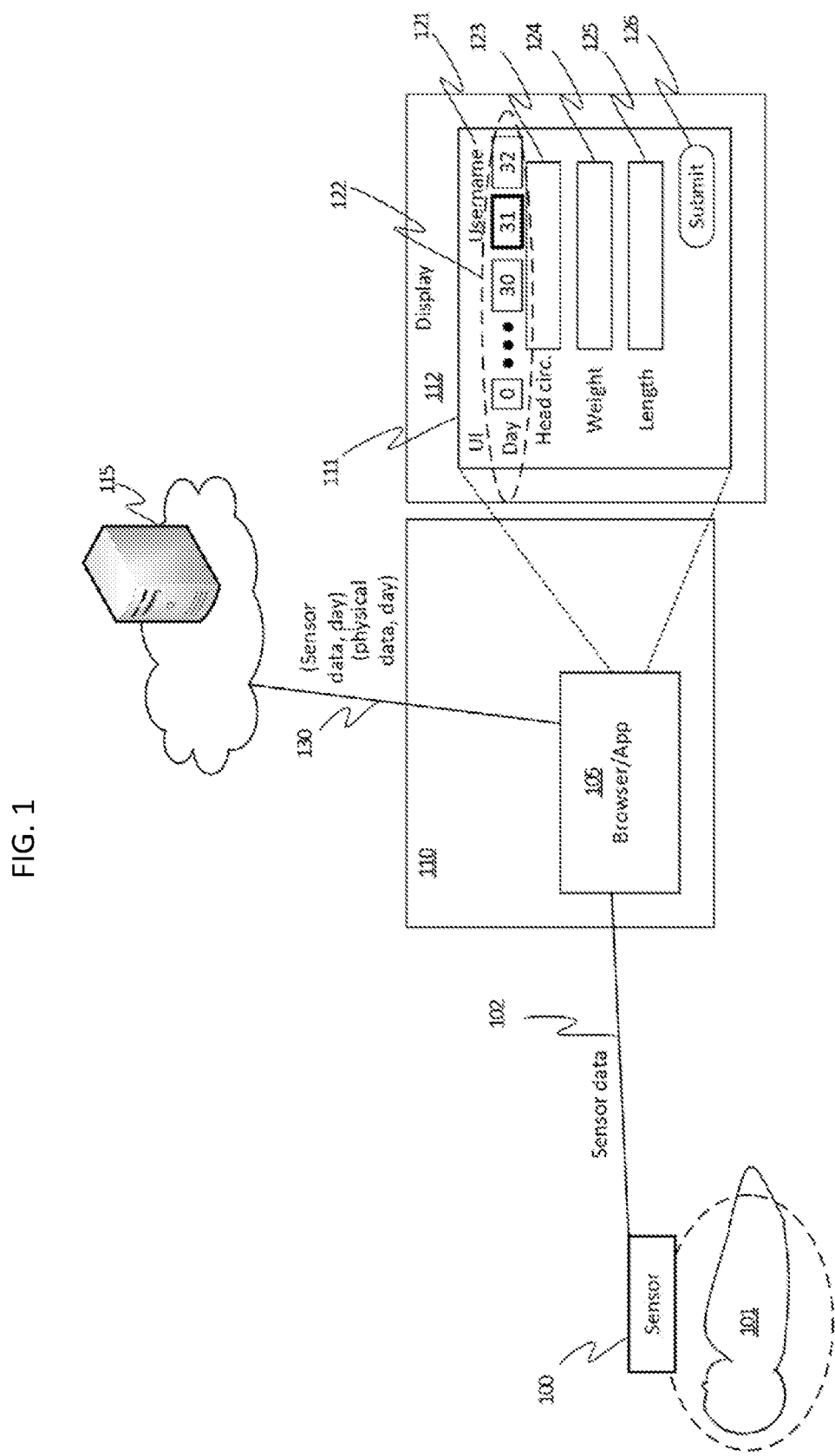
FIG. 1 illustrates an example of a system for tracking of neuro-development disorder in infants.

Systems and techniques are provided for tracking neurodevelopment in infants and identifying those at-risk for developmental issues. Certain implementations of the systems and techniques described herein can track neurodevelopment of a baby by using input provided by a user regarding a baby's physical characteristics taken on two or more specified days since birth and sensor input from a device capturing a rhythm produced by the baby's nervous system; perform a linear regression for a change, over a time period, in a parameter associated with the rhythm produced by the baby's nervous system and a change of one of the physical characteristic of the baby for that time period, over successive time periods; and based on a coefficient of determination for the linear regression, identify whether the baby is at risk for neuro-developmental issues or showing typical development.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout the specification may, but do not necessarily, refer to the same embodiment.

Furthermore, the described features, advantages and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to." Unless defined otherwise, all technical and scientific terms used in this document have the same meanings as commonly understood by one of ordinary skill in the art.

In FIG. 1, a computing system—as a computing device or service platform—may receive the sensor data and the baby's physical characteristics to track neuro-development of the baby and identify whether the baby is at risk for a neuro-developmental issue. An example system for tracking of neuro-development disorders in infants may include one or more wearable sensor devices 100 that can be attached to a baby 101 in order to collect sensor data representing a rhythm produced by the baby's nervous system. The wearable sensors may be attached to one or more parts of the body of the baby, such as the head, the core (torso, lumbar areas) and the limbs (e.g., wrists in the arms and ankles in the legs). The sensor data and physical characteristics of the baby 101 may be provided to an application 105 on a user's computing device 110, which can perform a process for tracking and identifying the baby's neuro-development or be used to communicate with an application (as a service) on a service platform 115 that tracks the baby's neuro-development and identifies whether the baby is at-risk for developmental issues according to, for example, process 200 such as described with respect to FIG. 2A. In some cases, the sensor device 100 and the computing device 110 are implemented as an integrated component. In various implementations, components of computing device 110 may be embodied as described with respect to computing device 400 (see description of FIG. 4); and components of service platform 115 may be embodied as described with respect to computing system 500 (see description of FIG. 5).

The sensor device 100 capturing the rhythm produced by the baby's nervous system may be existing fitness trackers or other wearable computing devices. The rhythm may include one or more waveforms produced by the one or more wearable sensors, where each rhythm is associated with the time period. Devices and sensors that may be used include, but are not limited to, an accelerometer, visible-light and/or infrared light emitting diodes and photodiodes (e.g., for pulse oximetry), magnetometer (e.g., a Hall-effect sensor), gyroscope, temperature sensor, pressure sensor, and various electrodes. Placement of one or more of such sensors and circuitry may be used to detect movement, heartbeat, heart rate, skin conductance, respiration, swallowing, or even sucking (e.g., by being incorporated into a pacifier). As with the physical characteristics of the baby, the captured sensor data is associated with the number of days since birth that the data was captured. The sensor data may be captured over a period of a full day or at least for a period of time sufficient to obtain an appropriate amount of data (to cover the rhythm activity of interest). In some cases, minutes may be sufficient. In other cases, one or more hours of data are captured. Certain implementations may utilize devices that can be worn or used by the infant continuously over days, weeks, and/or months.

Sensor device 100 (such as when in the form of a wearable computing device) may include various computing components that enable the device 100 to implement the features attributed to computing device 110. In either case, sensor data 102 from sensors at sensor device 100 may be communicated to computing device 110 for analysis (directly or indirectly by further communication of data to service platform) via wireless or wired communication. Both date and time information may be provided with the sensor data from the sensor device 100 or just the time information may be provided with the sensor data from the sensor device 100 and the date (or day) information applied by the application 105 at the computing device 110 (or possibly upon receipt at the service platform 115.

In the example illustrated in FIG. 1, the system may have one or more sensors configured to capture one or more physical characteristics values for a baby. The physical characteristics values may include, for example, head circumference measurement, weight, and body length. In some scenarios, a user may enter data for a baby (e.g., indicated by username 121) via the user interface 111 rendered on a display 112 that includes input fields for day of measurement 122 (indicated as number of days since birth), head circumference measurement 123, weight 124, and body length 125. The user can submit the data (e.g., via a submit command 126) so that the data is stored and/or sent for processing by application 105 at the computing device 110 and/or at the service platform 115. Accordingly, both the sensor data and the physical characteristic data (as well as date or day information) can be communicated (130) to service platform 115 from the computing device 110.

The application 105 may perform some a process for tracking and identifying the baby's neuro-development (such as process 200 described with respect to FIG. 2A) or the application 105 may be used to access the functionality of the service on the service platform 115 and provide a mode of communication between the user and the service. For example, application 105 may be a web browser application or a thin application and provide a portal to the service on service platform 115. When application 105 is a web browser or thin application, the service platform 115 provides the processing power to carry out the process for identifying whether the baby is at-risk. The baby's data may be stored at the service platform 115 and/or at the computing device 110 and/or at another location (e.g., cloud storage) accessible by the service platform 115 and/or the computing device 110. It should be understood that privacy and security rules for such data may be used.

Figure 2A:
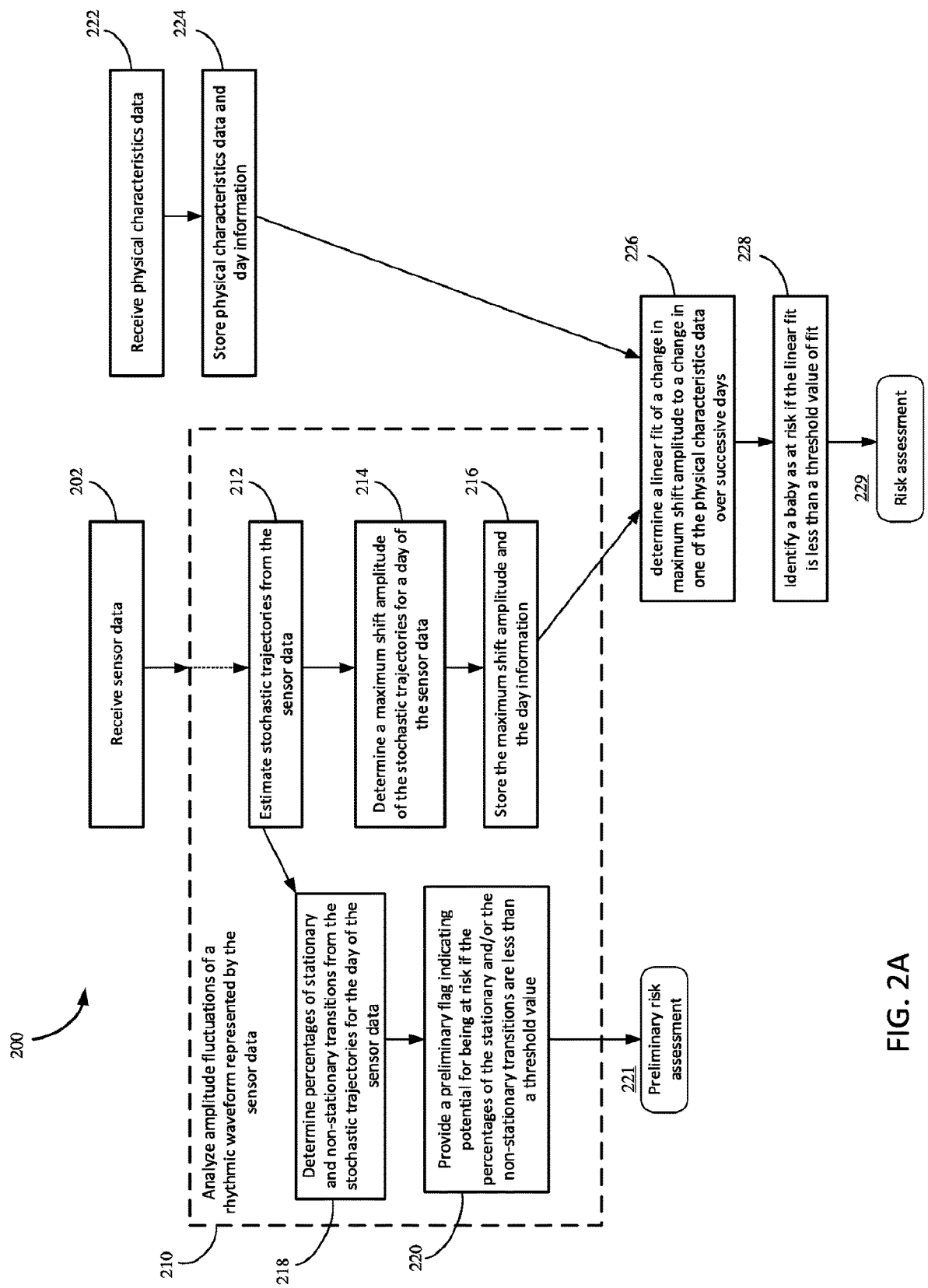
FIG. 2A illustrates an example of a process for tracking neuro-development disorder in infants.

The software application 105 or service (at platform 115) can, when executed by one or more hardware processors, identify whether the baby is at risk for neuro-developmental issues or showing typical development preliminarily through an analysis of a single day's sensor data, and start confirming and/or monitoring potential neuro-developmental issues using at least two day's sensor data and physical characteristics data. Outcomes can be communicated for display at a user's computing device (e.g., display 112 of computing device 110 or a display of another computing device). In practice, months of data may be collected and the results updated each day new data is entered and/or in response to a specific request to update the results, FIG. 2A illustrates an example of a process for implementing in the above illustrated system for tracking neuro-development disorders. In some scenarios, a process for tracking neuro-development disorders in an infant 200 may be performed by a computing device or system running an application (which can be stored as computer-readable instructions on a storage system associated with the computing device or system). The process 200 includes analyzing sensor data representing a rhythm produced by a baby's nervous system on a particular day and identifying whether a baby is at risk based on a fitting of a change in stochastic trajectories estimated from the sensor data to a change in a physical characteristic of the baby over time. In the particular example illustrated in FIG. 2A, the process 200 may include receipt of sensor data 202. The process may also include analyzing amplitude fluctuations of a rhythmic waveform represented by the sensor data 210. For example, a computing device or system running the application or service may analyze fluctuations of the amplitude of the rhythmic waveform captured by the device over time on the day of capture. The analysis may include estimating stochastic trajectories from the sensor data received for a particular day 212. Optionally, the process may perform certain pre-processing of data to, for example, obtain segments containing relevant signal (see example regarding sensor data representing neuro-motor development using an accelerometer and temperature sensor). In analyzing the fluctuations of amplitude 210, the process may estimate a probability density function (PDF) that characterizes the behavior indicated by the received data. In some scenarios, the process may use a Gamma function, in which there are two parameters of interest, the shape of distribution (e.g., Gaussian, exponential) and the dispersion. (sometimes referred to as the "scale" and which represents here the noise-to-signal ratio).

Figure 17A:
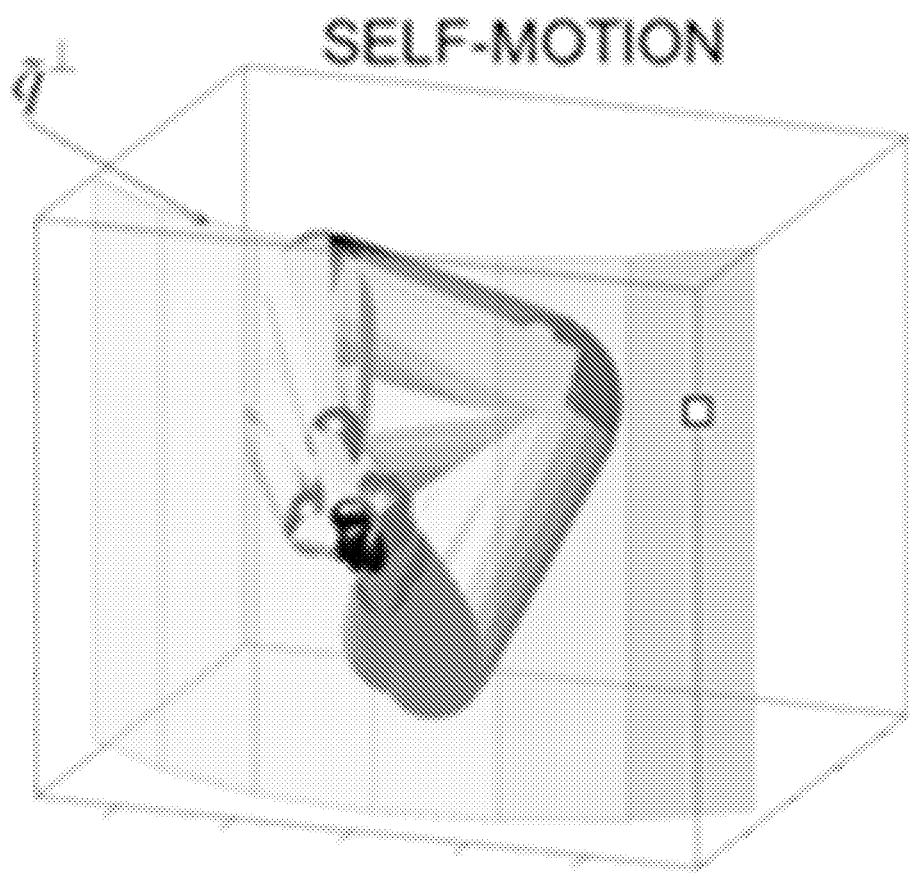
FIGS. 17A-17C illustrate an example of a Gamma plane showing the noise-to-signal transitions for self-motion and goal-directed motion of a subject.
Figure 17B:
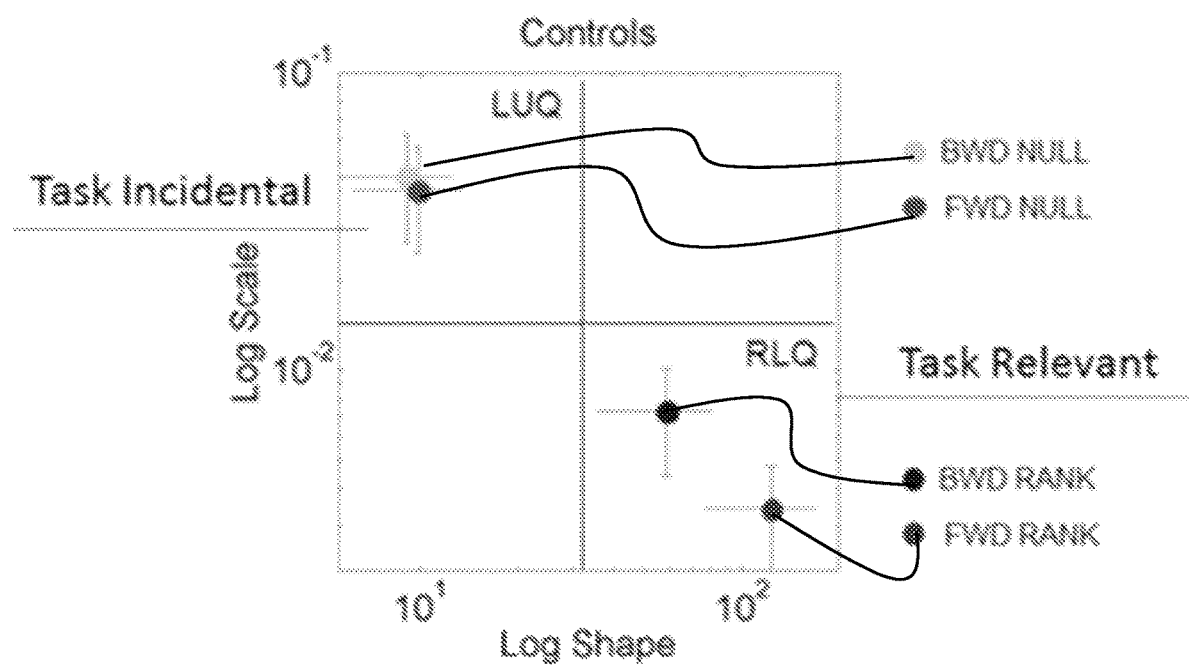
Figure 17C:
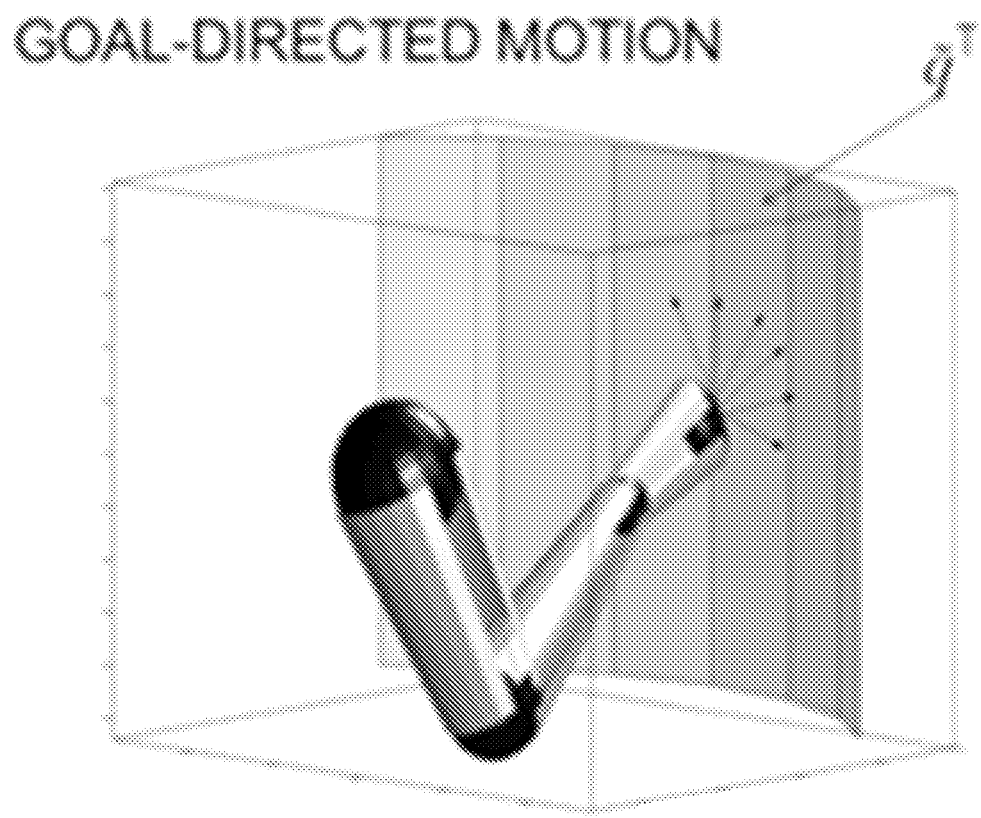

The device or system differentiates the data with high dispersion (high noise) from those with low dispersion (low noise, high signal). To perform the differentiation, the process may delineate two quadrants of interest of the Gamma parameter plane using a median scale value and a median shape value that can be calculated from the cumulatively estimated Gamma parameters obtained from one or more waveforms of the rhythm. These two quadrants of interest are the left-upper quadrant (LUQ) and the right-lower quadrant (RLQ), an example of which is shown in FIG. 17B. The lower quadrant data (particularly the RLQ) tend to be symmetric distribution (the higher the shape value, the more symmetric the distribution, and the lower the scale value, the lower the noise). The upper quadrant (particularly the LUQ) reflects higher noise and more skewed shapes.

For the data obtained over the course of the number of hours in a particular day, the system may track the magnitude and frequency of the transitions between the LUQ and RLQ. That is, the area of interest is in the change from noise to signal (i.e., from LUQ to RLQ) and in the change from signal to noise (i.e., from RLQ to LUQ).

Figure 3A:
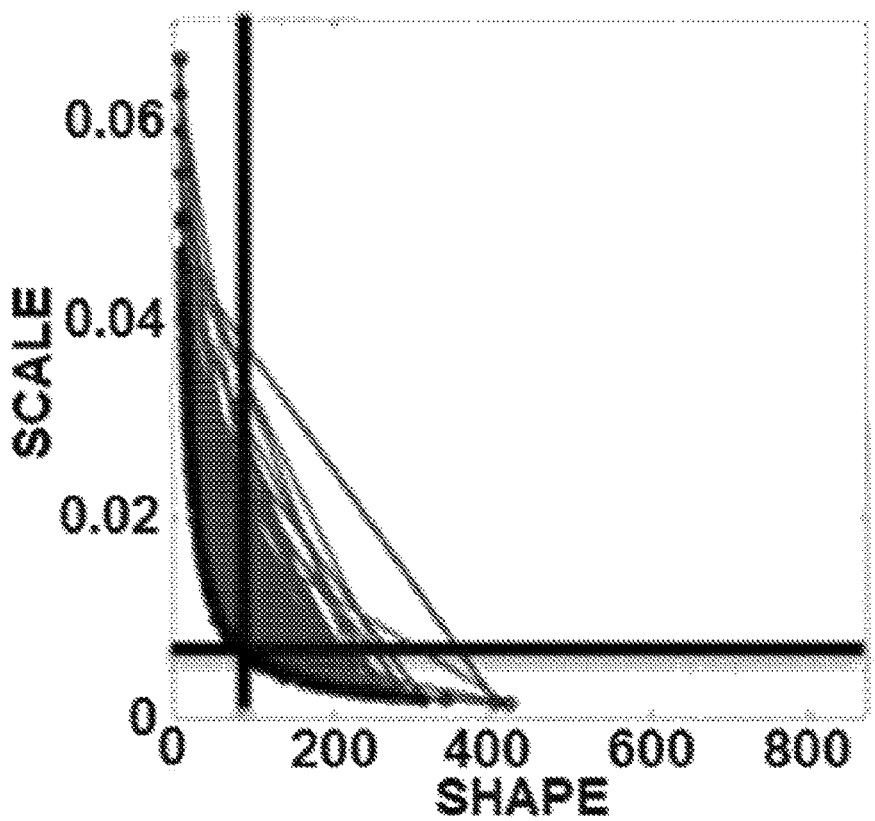
FIGS. 3A-3D illustrate example plots corresponding to an illustrative analysis of amplitude fluctuations of the stochastic signatures extracted from one or more waveforms of a rhythmic from sensor data.

FIG. 3A illustrates an example plot of stochastic trajectories. As can be seen, some segments of the trajectories (the segments representing the change in probability distribution) transition from LUQ to RLQ and vice-versa. When a segment does not transition to another quadrant (an inner-quadrant transition), it can be referred to as a stationary transition. There may be two or more transitions in a segment trajectory where a segment transitions between quadrants (inter-quadrant transitions). These segments can be referred to as non-stationary transitions. One parameter of interest here is the frequency of transitions. To calculate the frequency of transitions, the system may use median-ranked selection criteria to select points that belong to each quadrant (as described with respect to FIG. 3A). For example, the LUQ points are those above the median scale and below the median shape. The system forms one array that includes indexes to the LUQ points and another array that includes indexes to the RLQ points. The order of the indexes into these points provides information on the history in the frequency of change in the stochastic signatures. That is, the order shows whether there was a transition that remained within the same quadrant or a transition that jumped successively from one quadrant to the other. The system may numerically differentiate the two arrays containing such indexes (the "indexes arrays") for the LUQ and RLQ to count the number of instances when the change was consecutive within one quadrant (i.e. the difference from one shift to another is 1), which is explained in more detail below.

Figure 3B:
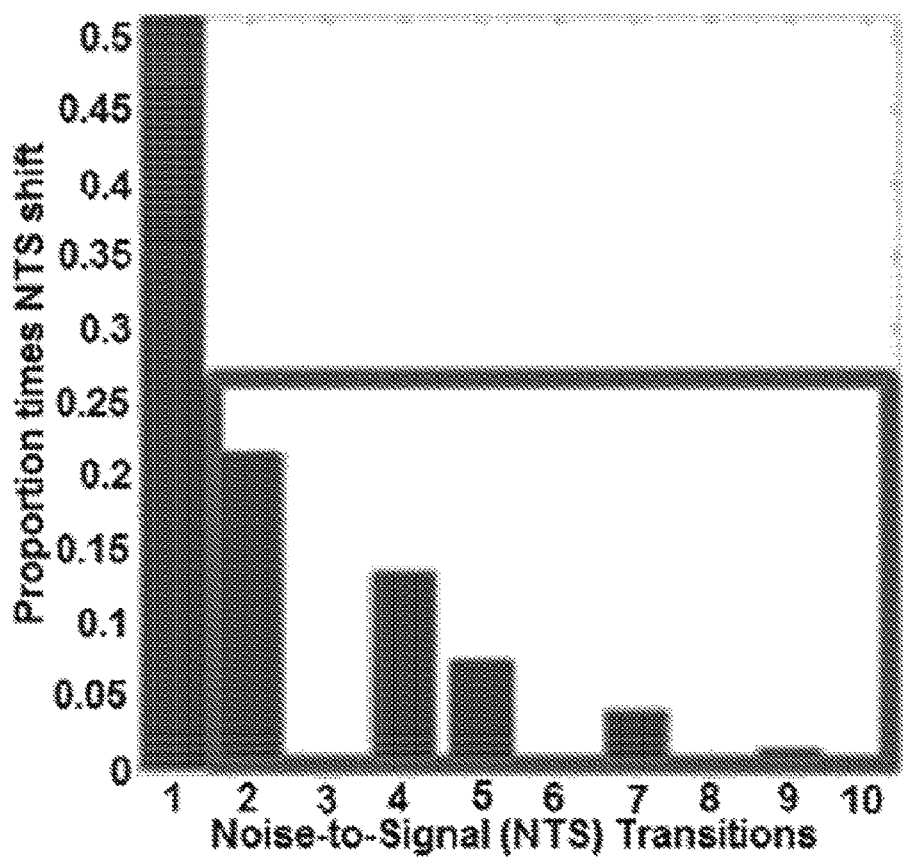

Differences from one shift to another that are greater than 1 denote instances when the shifting is from one quadrant to another. For example, if the indexes array for the points in the LUQ has values [1, 2, 3, 4, 6, 9, 10, 11], then the difference array will be [1, 1, 1, 2, 3, 1, 1]. This means that the process remained stationary in the LUQ for three consecutive times, then jumped to the RLQ, jumping 2 instances and then came back to the LUQ and returned to the RLQ where it jumped three instances before it came back to the LUQ two more consecutive times. FIG. 3B shows a histogram with 10 bins quantifying the proportions of the stationary transitions and those quantifying non-stationary transitions (highlighted with a rectangle) for the example implementation. For the histogram, each bin is normalized by the number of occurrences to obtain the distribution of noise-to-signal transitions and the proportion of times spent in each quadrant of high or low noise along with the proportion of shifts.

Figure 3C:
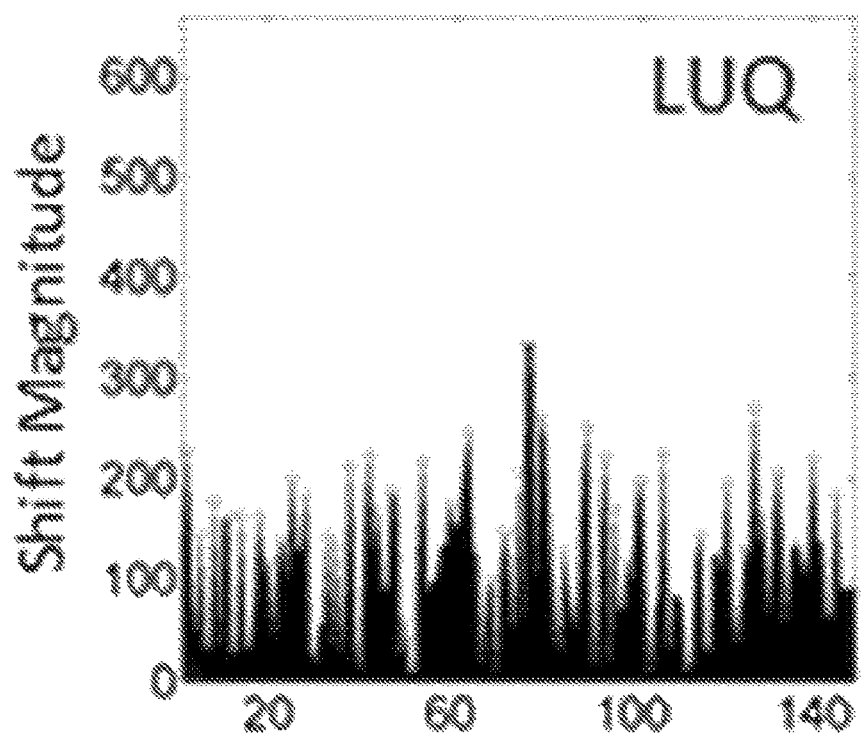
Figure 3D:
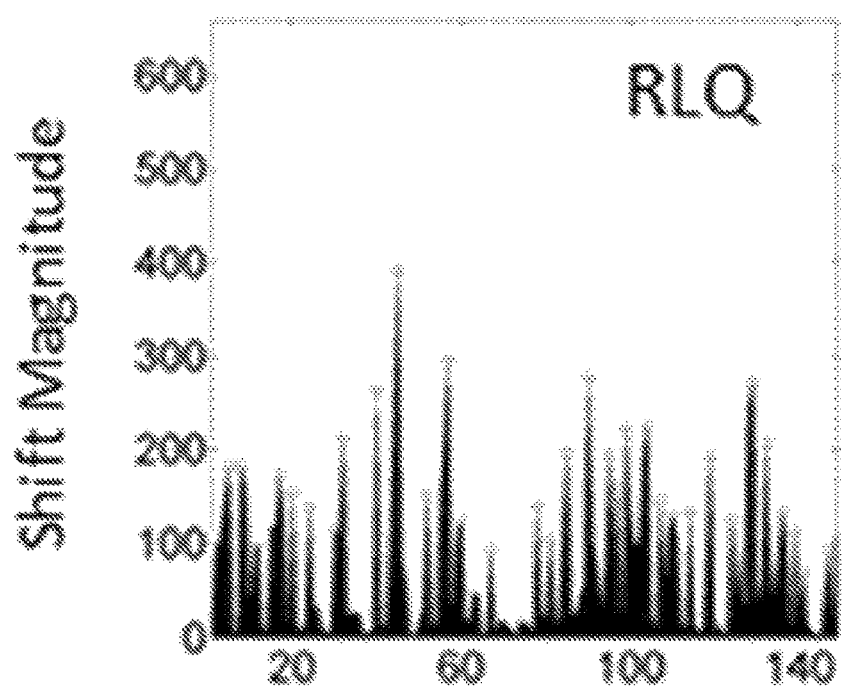

FIGS. 3C and 3D show area-plots of the shifts in the trajectories illustrated in the example of FIG. 3A corresponding to each quadrant of interest. FIG. 3C shows the area-plot of the shifts in the trajectories in the LUQ and FIG. 3D shows the area-plot of the shifts in the trajectories in the RLQ. Here, the system may calculate the magnitude of the vector connecting the points positioned on the Gamma parameter plane representing the estimated PDF. In determining the magnitude of the transitions between quadrants (the time series of shifts in Gamma parameters), the system may calculate the norm of the difference between the estimated (shape, scale) vector at time t+1 and that at time t. Then the system may obtain a temporal profile of these magnitude values for all the transitions (in the order in which they were obtained).

Returning to FIG. 2A, the system may determine a maximum shift amplitude over all shifts between quadrants for a time period of the sensor data 214 and store the maximum shift amplitude and the time information 216. For example, the system may determine the maximum shift amplitude over all shifts for a day of the sensor data and store the maximum shift amplitude with the day information. The system may also use the change of maximum shift amplitude along with the change in the baby's physical characteristics over multiple days to identify and monitor neuro-development of the baby. In determining the maximum shift amplitude for a day of sensor data the system may take the point in RLQ with the minimum scale value and the maximum shape value (the PDF with minimum noise-to-signal ratio and maximal symmetric shape) and subtract the value at that point from the point in LUQ with the maximum scale value and minimum shape value (the PDF with maximum noise-to-signal ratio and most skewed shape). The system may then determine the magnitude of the resulting vector on the Gamma parameter plane using a norm, such as Euclidean norm. For example, the maximum shift amplitude in the plot of FIG. 3D appears to be about 400.

The system may repeat the analysis—particularly the determination of a maximum shift amplitude 214—over the course of at least one other day during a period of time can provide additional input regarding the change of the assessment over time, and generate a linear response that can further be used to flag for neuro-developmental issues.

In particular, process 200 may also include retrieving physical characteristic data of the baby 222 and store the physical characteristic data with day information 224. Then the system may perform a fitting of a change in maximum shift amplitude to a change in one of the physical characteristic data over successive days 226. The tracking of neuro-development thus occurs over a period of time.

In some scenarios, the system may perform a fitting, such as a liner fitting, by taking the maximum shift amplitude calculated for a day of sensor data from a baby and dividing that value by the number of days since the baby's birth (to that day of sensor data) to generate a "normalized" value. The system may generate a digital representation, such as a plot, that represents the difference between that "normalized" value and a "normalized" value of a subsequent day of sensor data (the maximum shift amplitude calculated for that subsequent day of sensor data divided by the number of days since the baby's birth to that day of sensor data) against the change in one of the baby's physical characteristics that occurred between the two dates (the change value also being the difference of two "normalized" physical characteristic values that are "normalized by dividing the measurement by the number of days since the baby's birth). Then the system may fit these plotted points of these two rates of change to a line 228. The closer the fit is to a line (e.g., a coefficient of determination $r^2$ value of 1 for a linear regression), the more likely the baby is developing in a typical manner. Accordingly, the system may provide a risk assessment 229 by identifying whether the baby has normal neuro-development or has a risk of neuro-development disorder based on the linear fit 228.

Figure 16A:
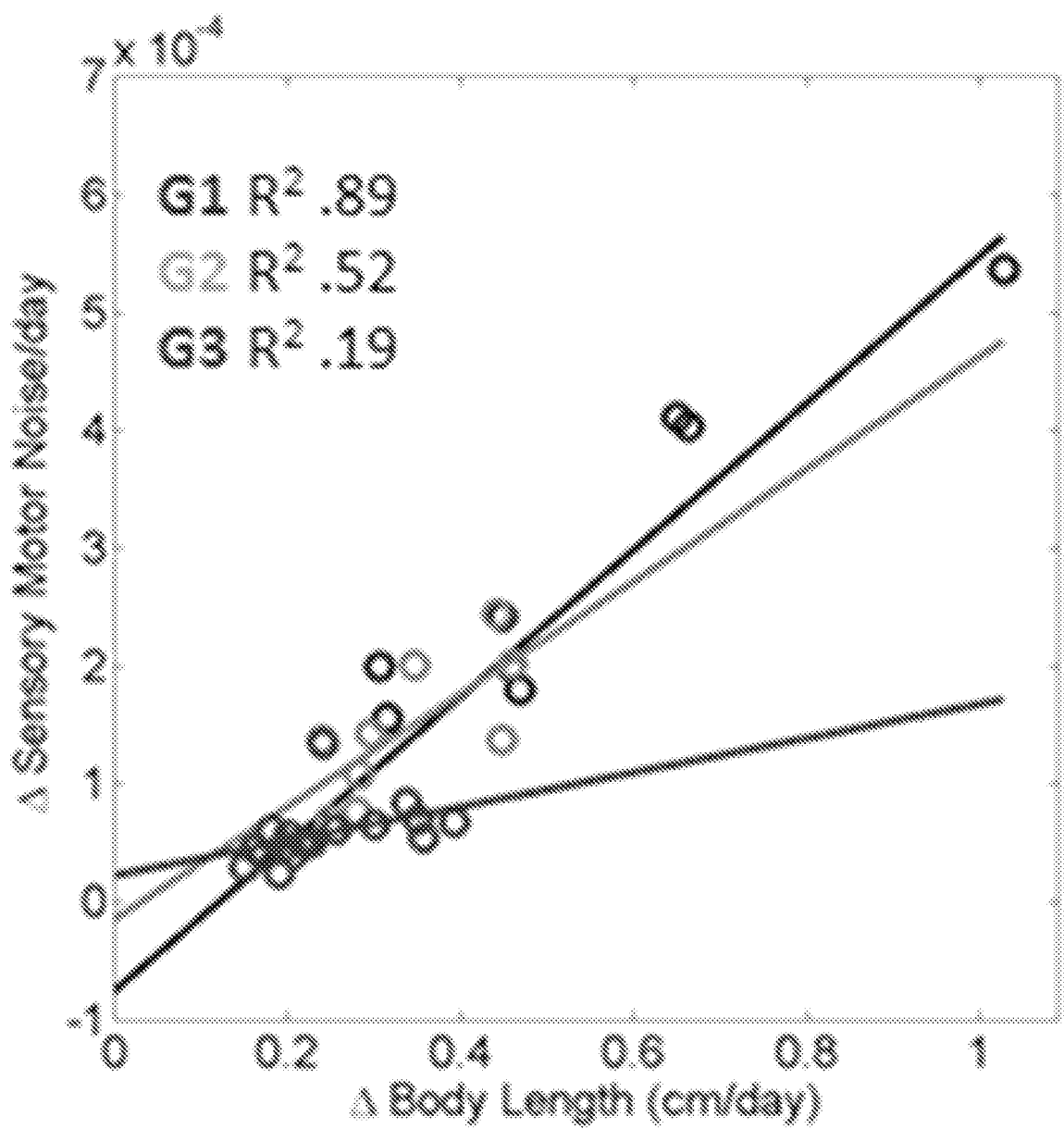
FIGS. 16A-16C illustrate an index of risk uncovered to automatically flag neurodevelopmental derail or stagnation very early on as identified in an example case study.
Figure 16B:
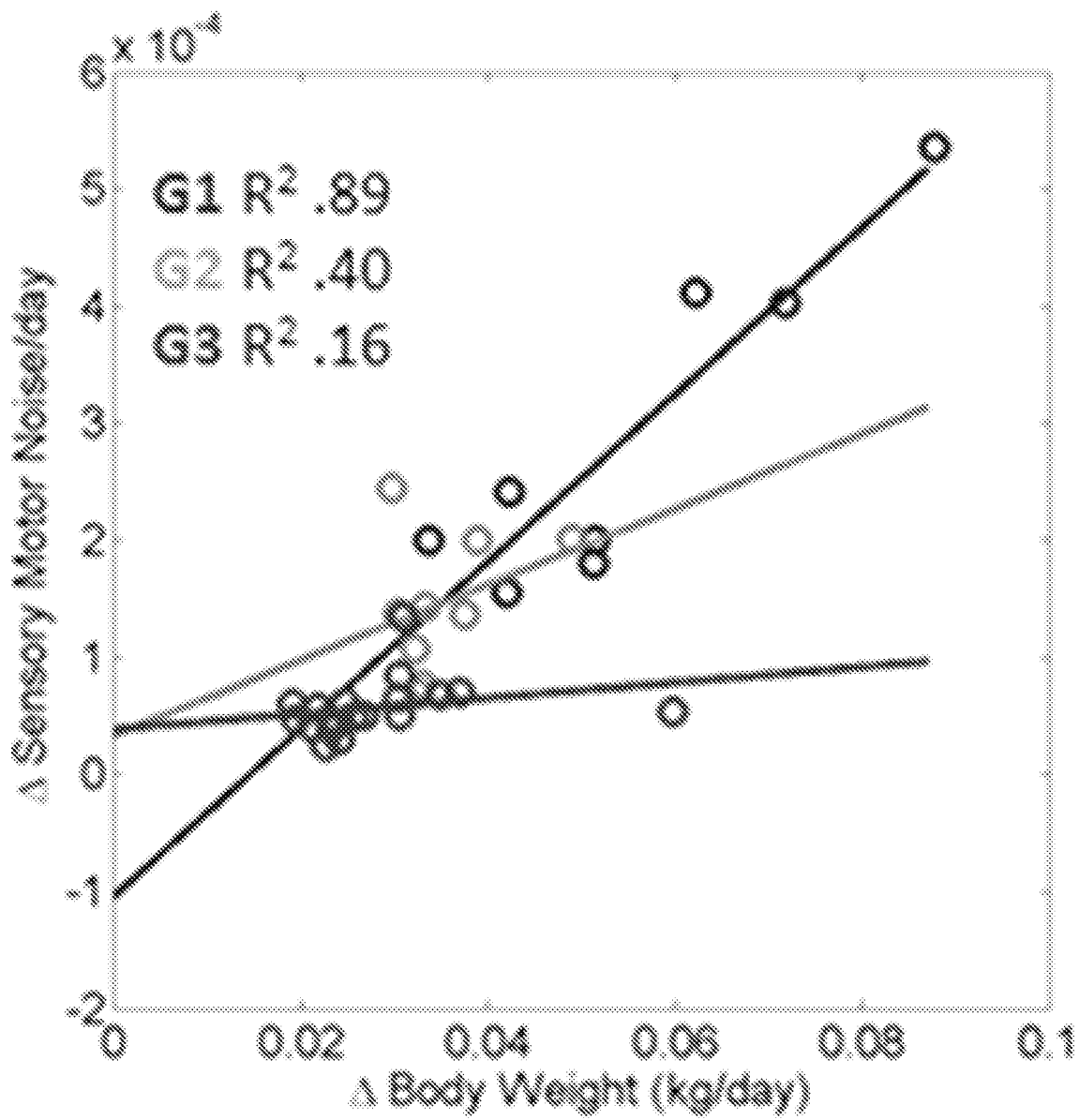
Figure 16C:
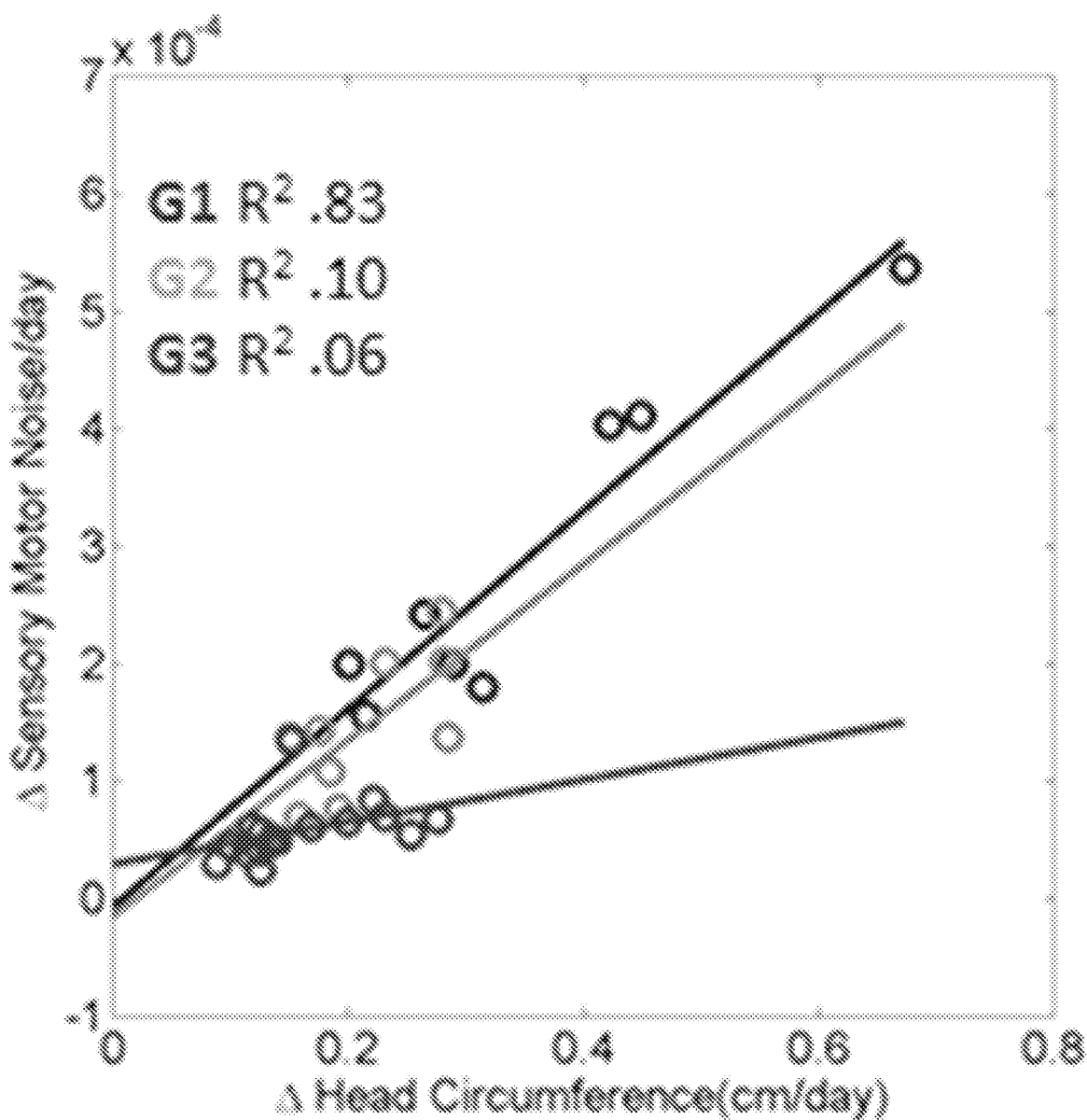

In determining whether the baby has neuro-development disorder, the system may identify the baby as being within typical development where the $r^2$ value is between 0.8 and 1. In some implementations, the system identifies the baby as being at risk for neurodevelopmental issues where the $r^2$ value is below 0.5. These and other threshold values may be optimized as more data is collected and neuro-developmental issues are correlated to certain values over time. In some scenarios, the system may determine the slope of the fitted curve, such as the fitted line, in order to determine whether the subject has a risk of neuro-development disorder, which may include stunted, delayed or advanced disorder. Referring to FIGS. 16A-16C, for example, the system may determine the slope of the fitted line and determine that the subject has normal neuro-development if the slope of the fitted line is close to 1 (e.g., G1), or in the range of 0.8-1.0, or in the range of 0.5-0.8. The system may determine that the subject has a neuro-development disorder if the slope of the fitted line is less than 0.5 (e.g., G3). The system may continuously update the calculation of linear fit as new sensor data and physical characteristics data are received for a particular day (and appropriate values calculated per the described processes).

With further reference to FIG. 2A, in addition to the maximum shift amplitude, from the stochastic trajectories, as an outcome measure for a baby, the system may determine the percentages of stationary and non-stationary transitions from the stochastic trajectories for the day of sensor data 218. In particular, the system may calculate the percent frequency of the shifts quantified within a given quadrant (e.g., stationary shifts in the LUQ) and between quadrants (e.g., non-stationary shifts from the LUQ to the RLQ) and use the outcome as a preliminary assessment (see also description provided with respect to FIG. 3B). This summary point can be averaged across multiple days of collected data. However, a single summary point (of percent transitions for stationary shifts in the LUQ or of percent transitions for non-stationary shifts from the LUQ to the RLQ) can be sufficient to identify a potential flag. In one implementation, the system may provide a preliminary flag indicating a potential for being at risk if the percentage of the stationary and/or the non-stationary transitions are less than a threshold value 220. For example, a threshold value for stationary summary points may be a value indicating less than 50% transitions and a threshold value for non-stationary summary points may be a value indicating less than 1% transitions. Accordingly, via a single summary measurement the system may provide a preliminary risk assessment 221 indicating that the baby is potentially at risk.

The preliminary risk assessment 221 may be a flag indicated in the baby's account or file with the service, a notification to the user (authorized medical professional, parent, or legal guardian), an alert sent to an electronic device associated with the medical professional, parent or legal guardian, or notification to an electronic device of a medical professional having authorization to receive medical information about the baby.

In some cases, the system can allow for a user to compare a baby's growth with another baby's development or with group data. It should be understood that in any cases where data of other babies are accessed, access to such data would be only that allowed by rules concerning privacy and security of health related data. For example, a parent may have an account to store the data collected for their first born and their second born child. That parent may use comparison features to track their second born child against their first born child.

Figure 2B:
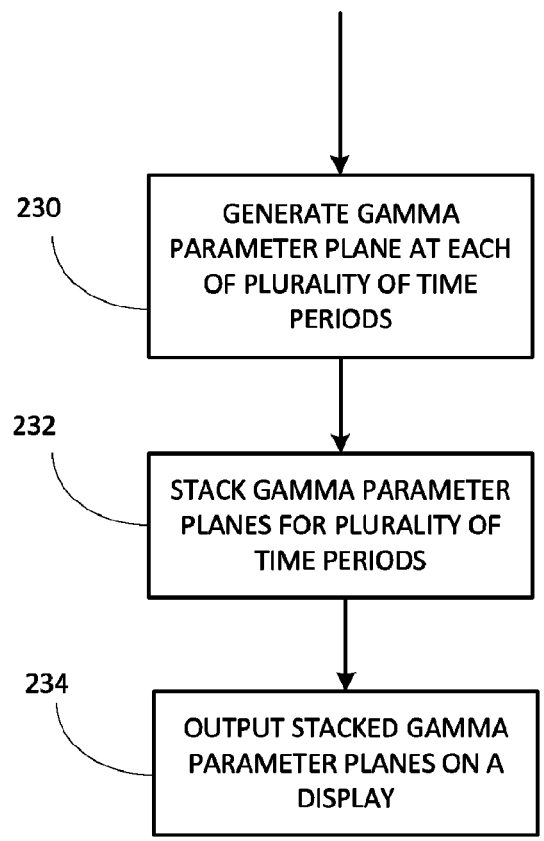
FIG. 2B illustrates an example of a process for determining a longitudinal assessment for a subject over a plurality of time lags.
Figure 18A:
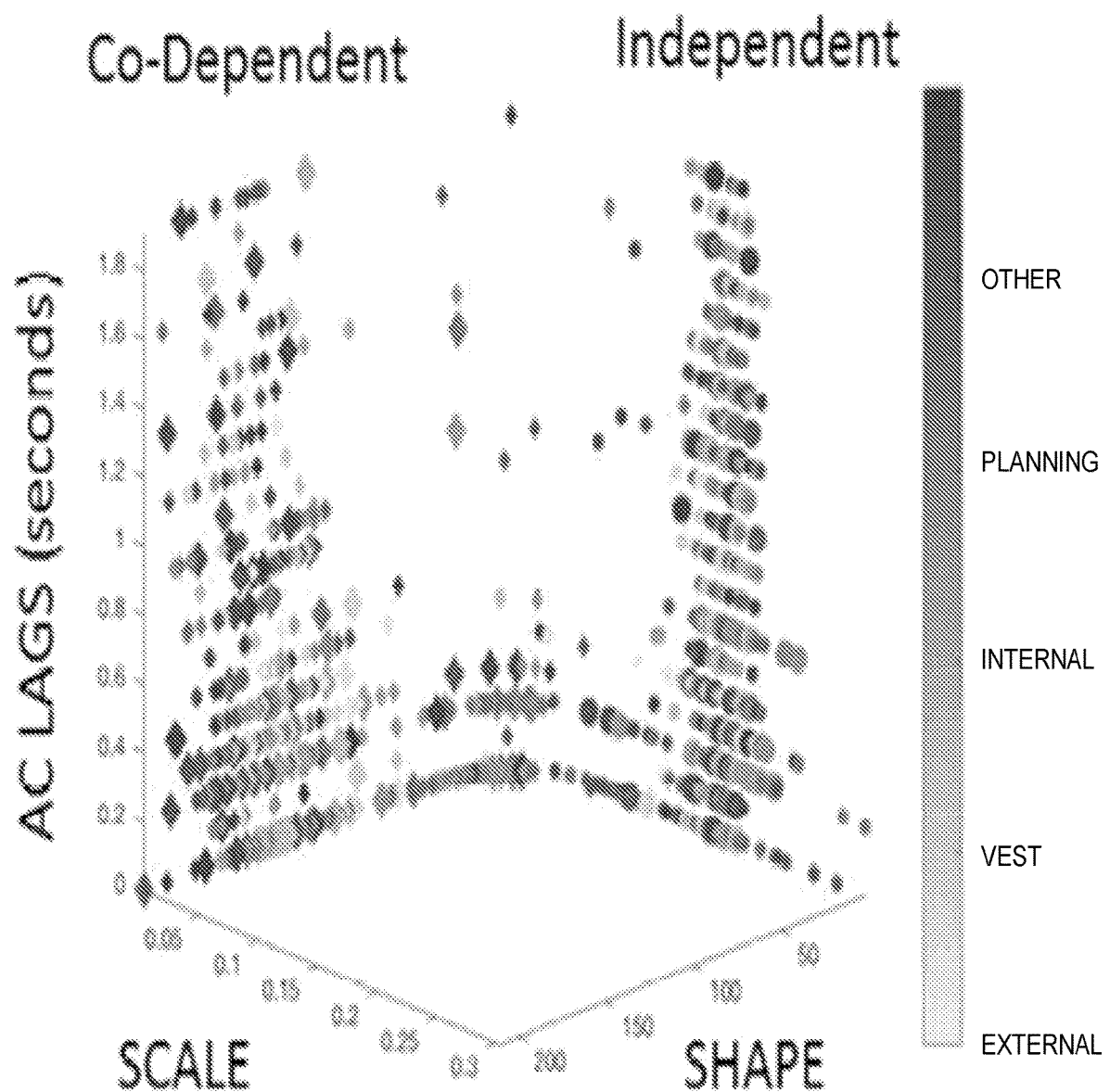
FIGS. 18A-18B illustrate examples of statistical spaces in Gamma planes stacked over time lags in a therapeutic setting for a child.
Figure 18B:
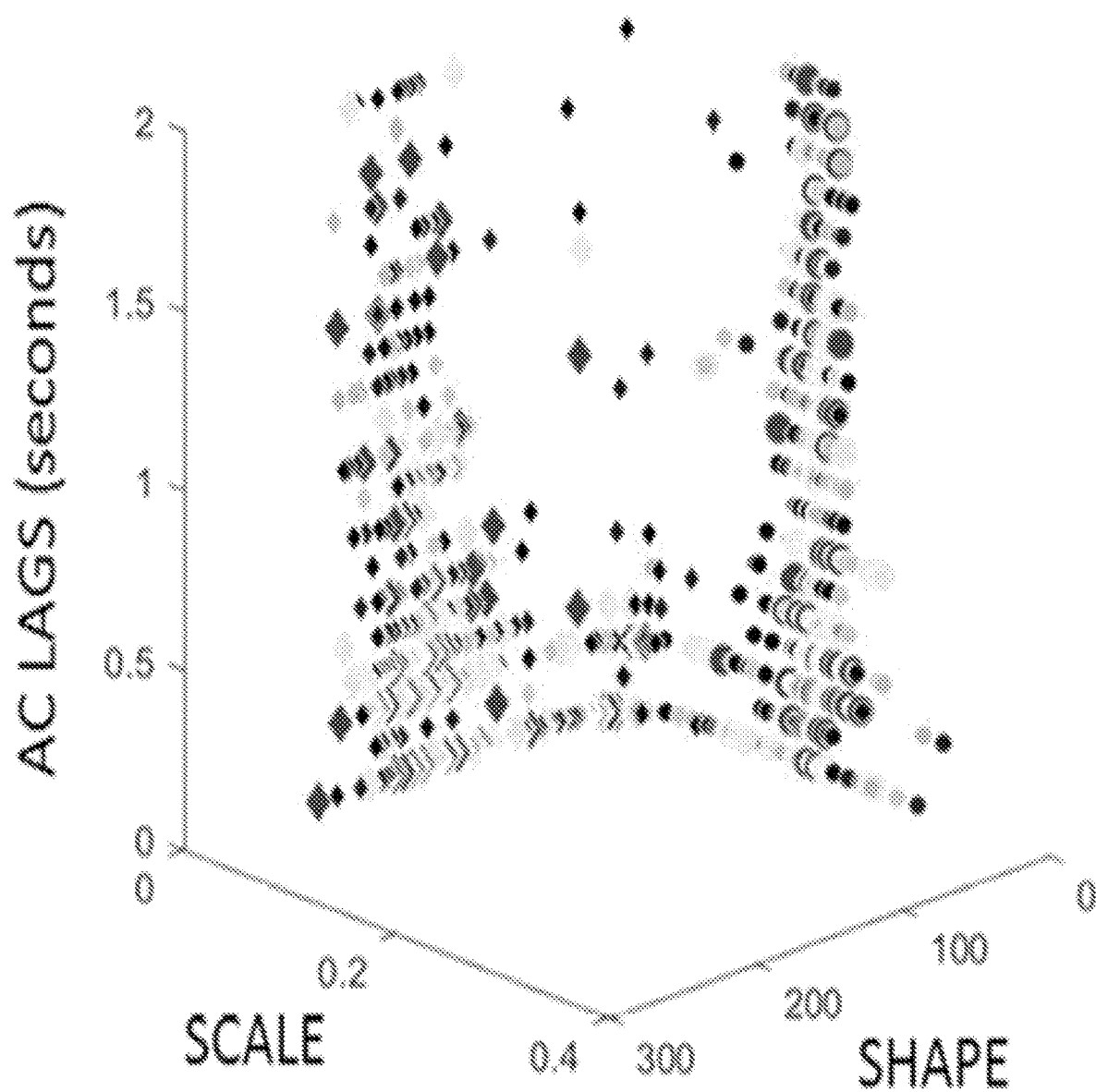

With reference to FIG. 2B, in some scenarios, the system may track longitudinal neuro-development of a subject over a period of time. The system may generate a Gamma parameter lag plane at each of the plurality of time periods 230, stack a plurality of Gamma parameter lag planes 232, and output the stacked Gamma parameter lag planes on a display 234. Each of the Gamma parameter plane in the stack corresponds to a time period in sequence over the plurality of time periods. Examples of stacked Gamma parameter lag planes are shown in FIGS. 18A-18B, in which each Gamma parameter lag plane includes a shape and a scale parameter of a continuous Gamma distribution family for the one or more waveforms of the rhythm associated with each time period for at least one of the wearable sensors. The wearable sensors may be attached to various parts of a subject's body, such as a taurus, a torso, a limb and a wrist. Further, each of the stacked Gamma parameter planes may also include an intersecting point (1901, 1902, 1903, 1904 in FIG. 19) so that the system may display a trajectory of the intersecting points over the plurality of time periods. The system may determine the intersecting point to be where a line representing a median of the scale and a line representing a median of the shape intersect (an example of which is shown in FIG. 3B).

With reference to FIGS. 18A-18B, in an application with therapeutic intervention using sensory driven therapies in a child. (i.e., before the intervention in FIG. 18A and after the intervention in FIG. 18B), sampling the two subspaces (Gamma parameter plane RLQ and LUQ) for each lag and over time shows how the therapy helps fill up the space of probabilities representing co-dependent and independent processes as a child learns to interact with an adult therapist within a therapeutic setting.

Figure 19:
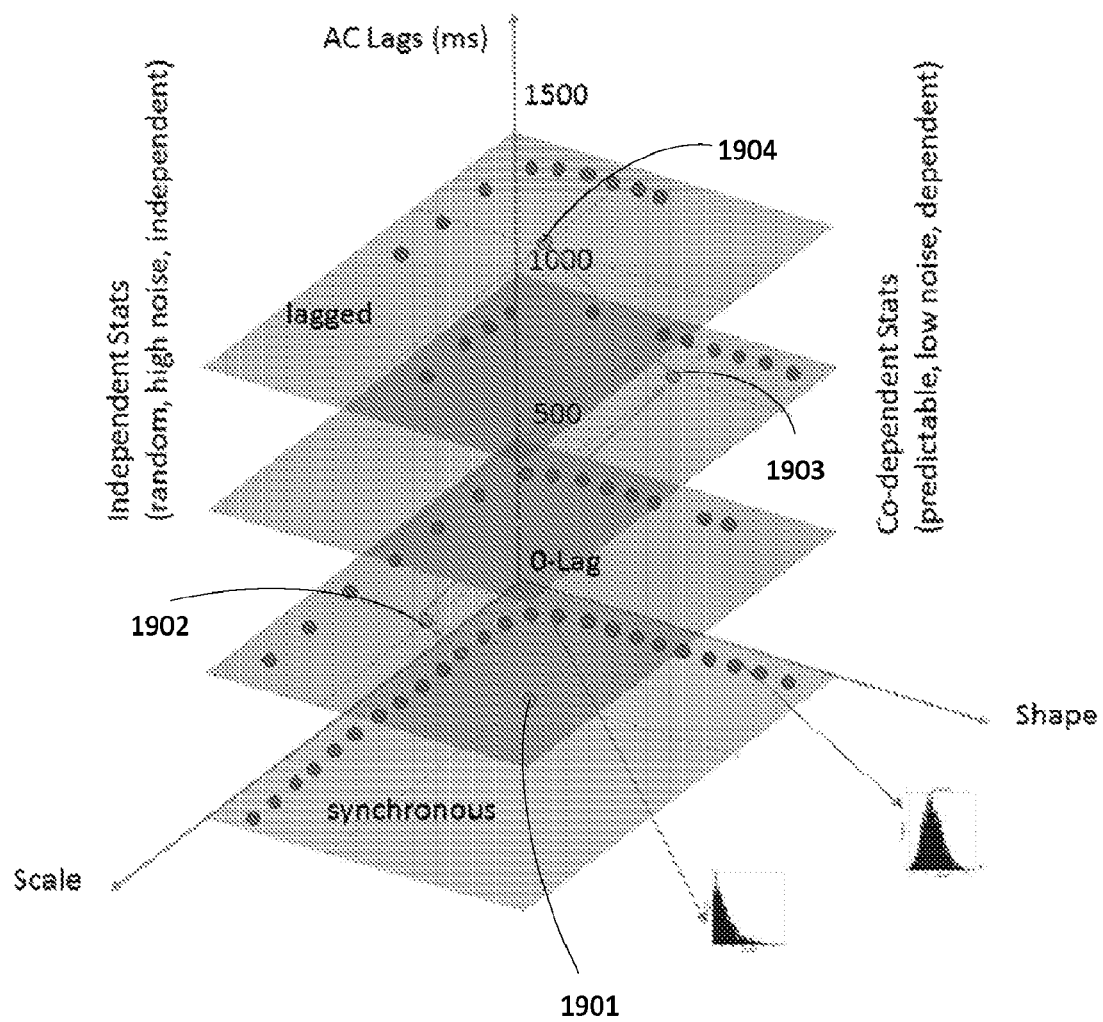
FIG. 19 illustrate an example of statistical features of the degree of freedom of a body over time lags.

FIG. 19 shows a new model to capture the statistical features of the degree of freedom (DoF) problem that the brain faces, namely that there are more DoF in the body that need to be internally controlled than dimensions in the space where the body moves. The question is how to distribute the DoF statistical variability to accomplish deliberate (intentional) actions. FIG. 19 shows that this problem can be resolved by using two orthogonal parameter spaces, one representing processes that are co-dependent in time, whereby events in the past predict the consequences of future events; and another with statistical independence, whereby events in the past do not contribute to the prediction of future events. See FIG. 10A-10D in the previous document to appreciate the Gamma plane partition into the RLQ (blue gradient) and LUQ (red gradient) sub-spaces as they longitudinally evolve when the baby develops. This new schematic as shown in FIG. 19 lifts the Gamma parameter plane for each lag and provides the general framework to test the system's evolution in time.

Accordingly, the system generates the Gamma parameter plane for each lag plane in the three dimensional space spanned by the Gamma parameter plane and the lags to build a visualization tool that informs user about the degrees of freedom (DoF) across the grid of nodes in the body that synergistically coordinate predictive or anticipatory activity with intent, such that present events are statistically co-dependent on past events (maximal autocorrelation with different lags). These lie on the RLQ (the right lower quadrant of each Gamma parameter plane for each lag). Likewise, the system may identify the DoF of the body that can independently vary whereby present events are minimally auto-correlated with past events (for various lags). These lie on the LUQ, the left upper quadrant of the Gamma parameter plane for each lag. Each plane at each lag spans a scatter of points across the Gamma parameter plane. The median of the estimated shape and scale parameters provide a separating demarcation between the two types of co-dependent and independent processes the that the system may capture.

To that end, the system does not rely on the assumption that stochastic movements of a subject are independent between the present and past events. Rather, the system samples from blocks with an overlapping sliding window (i.e., not assuming independency) and the size of the window is taken from a Gamma random process whereby the system samples across distributions of variable shapes and dispersions (i.e., not assuming identically distributed events). The system may obtain for each sensor, the autocorrelation function across various lags (e.g., from 0 lag to 2000 ms lag) to determine the degree to which the present events maximally depend on past events (maximal autocorrelation) and the degree to which the present events are independent of the past events (minimal autocorrelation).

Introducing the lags is important to characterize synergistic synchronous activities across the grid of nodes as the DoF are recruited and released to accomplish any task in any context. Some DoF will be recruited in the task-dependent manifold where processes are co-dependent in time and have low variability and high predictability. Others will be recruited in the complement space (orthogonal to the task relevant one) where the DoF are incidental to those solving the task. These are independently varying and are more random and noisier. This type of variability evolves as the baby's body learns to move in a controlled manner.

As shown in FIGS. 18A-18B and 19, the system tracks the learning in these two spaces as the stochastic trajectories visit each quadrant demarcated by the median lines (i.e., the RLQ and the LUQ corresponding to the co-dependent task-relevant and the independent task incidental DoF subspaces). The system measures the level of stationarity and non-stationarity of the stochastic trajectories, and measure the trajectory of the median points on each lag plane to examine the departure from fully synchronous processes at 0-lag. In doing this, the system may longitudinally track over time the rate of change in stochastic trajectories as correlated with the rates of incremental growth from the baby's visit to visit. A balance between co-dependent and independent random processes regarding synergistic DoF coordination can then be captured through various indexes in the frequency and time domains.

Figure 20:
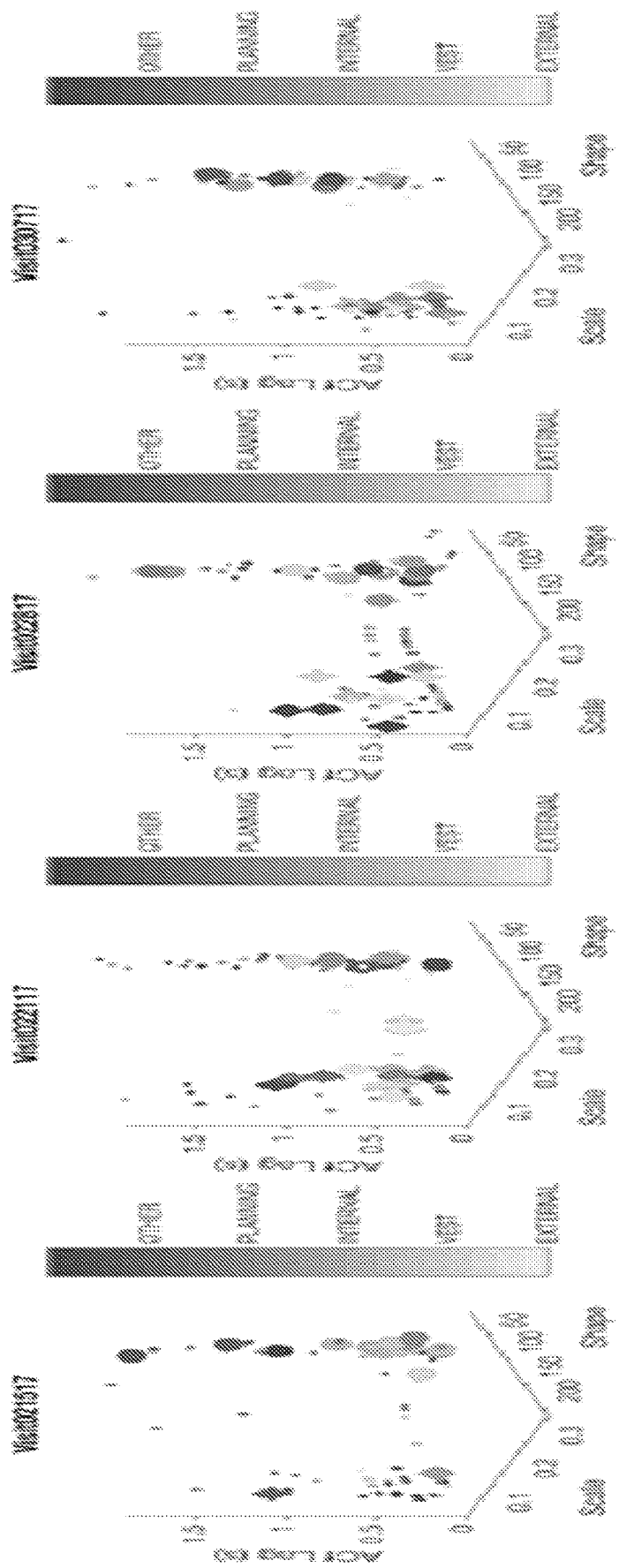
FIG. 20 illustrates an example of a longitudinal evolution of therapy outcomes as expressed by the statistical spaces in FIG. 18B.
Figure 20:
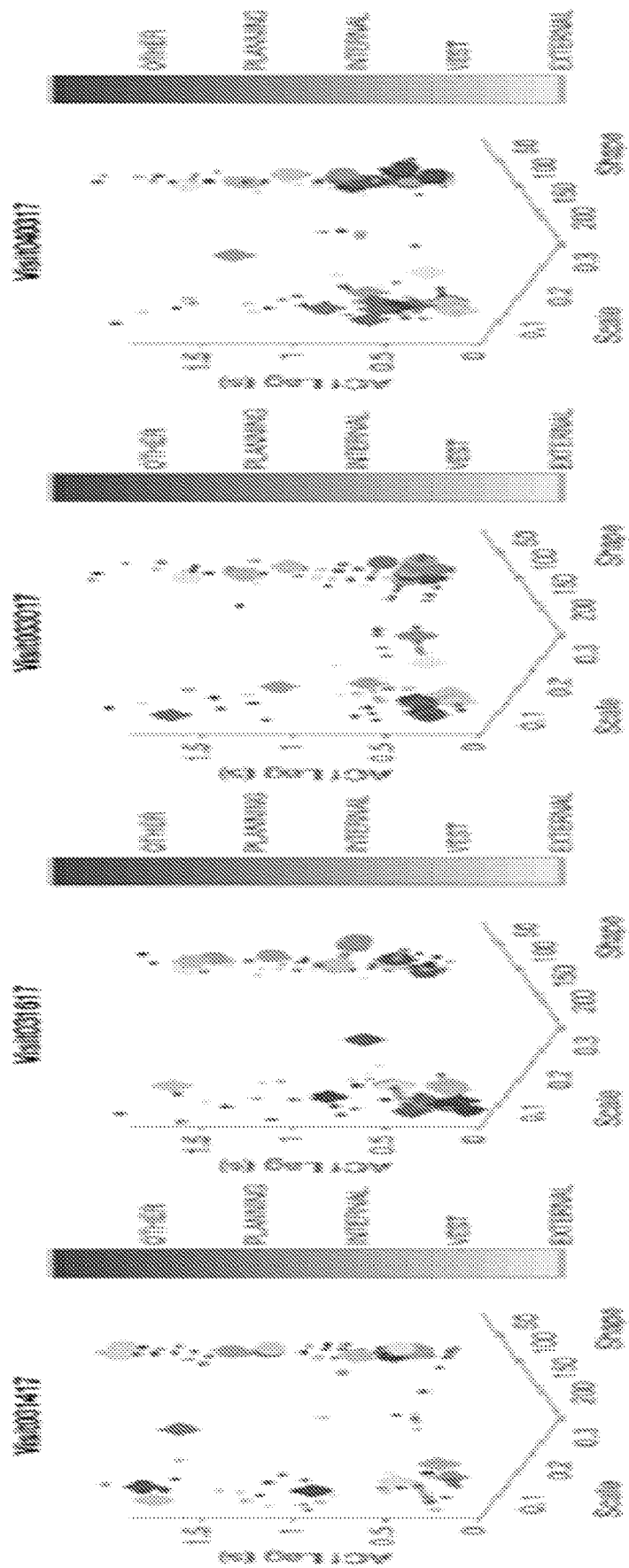
Figure 20:
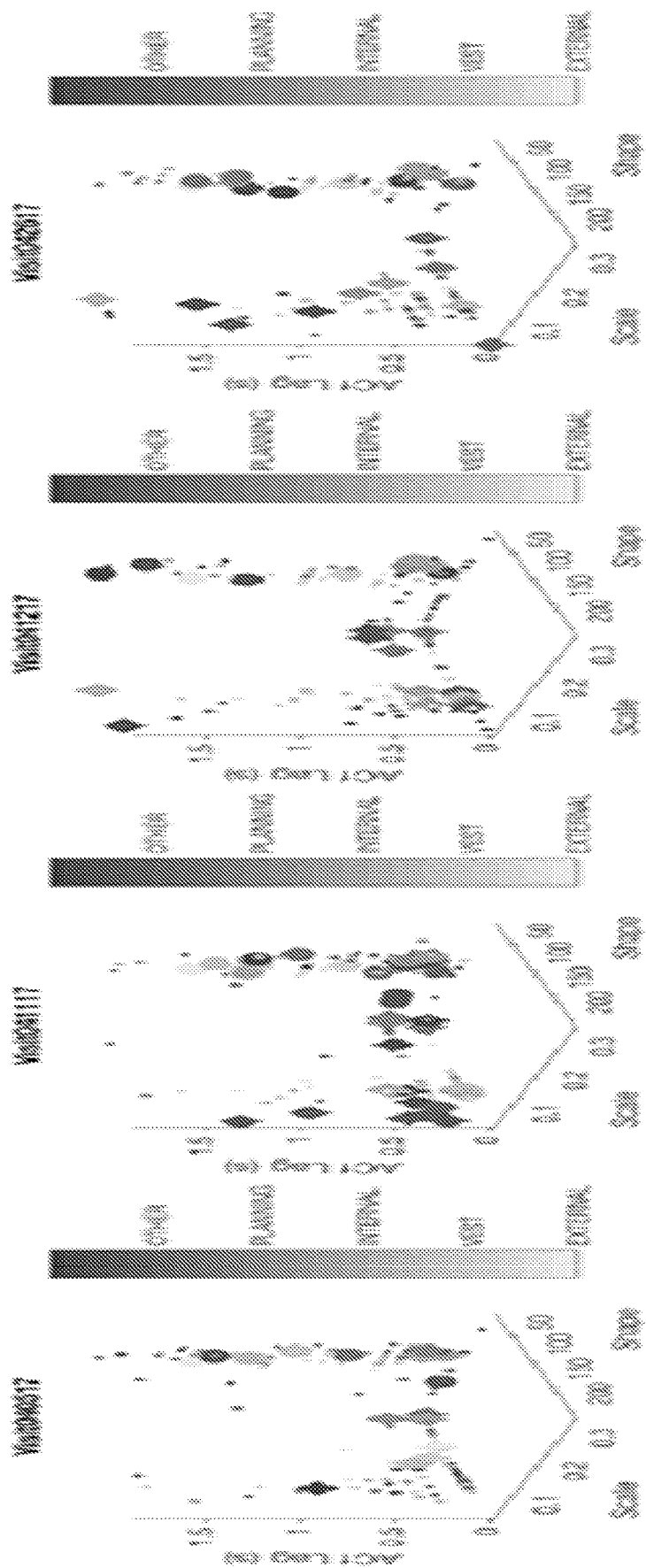

FIG. 20 shows a longitudinal evolution of therapy outcomes as expressed by the statistical spaces described in FIGS. 18A-18B. Note the Gamma parameter plane at 0-lag is initially disjointed (where synchronous DoF interact in the LUQ (independent) and RLQ (co-dependent) sub-spaces; but over time in the month of April (days 5, 11, 12 and 26) the child and therapist are interacting more. Different colors along the gradient express input driving the motions from different sensory domains.

Figure 21:
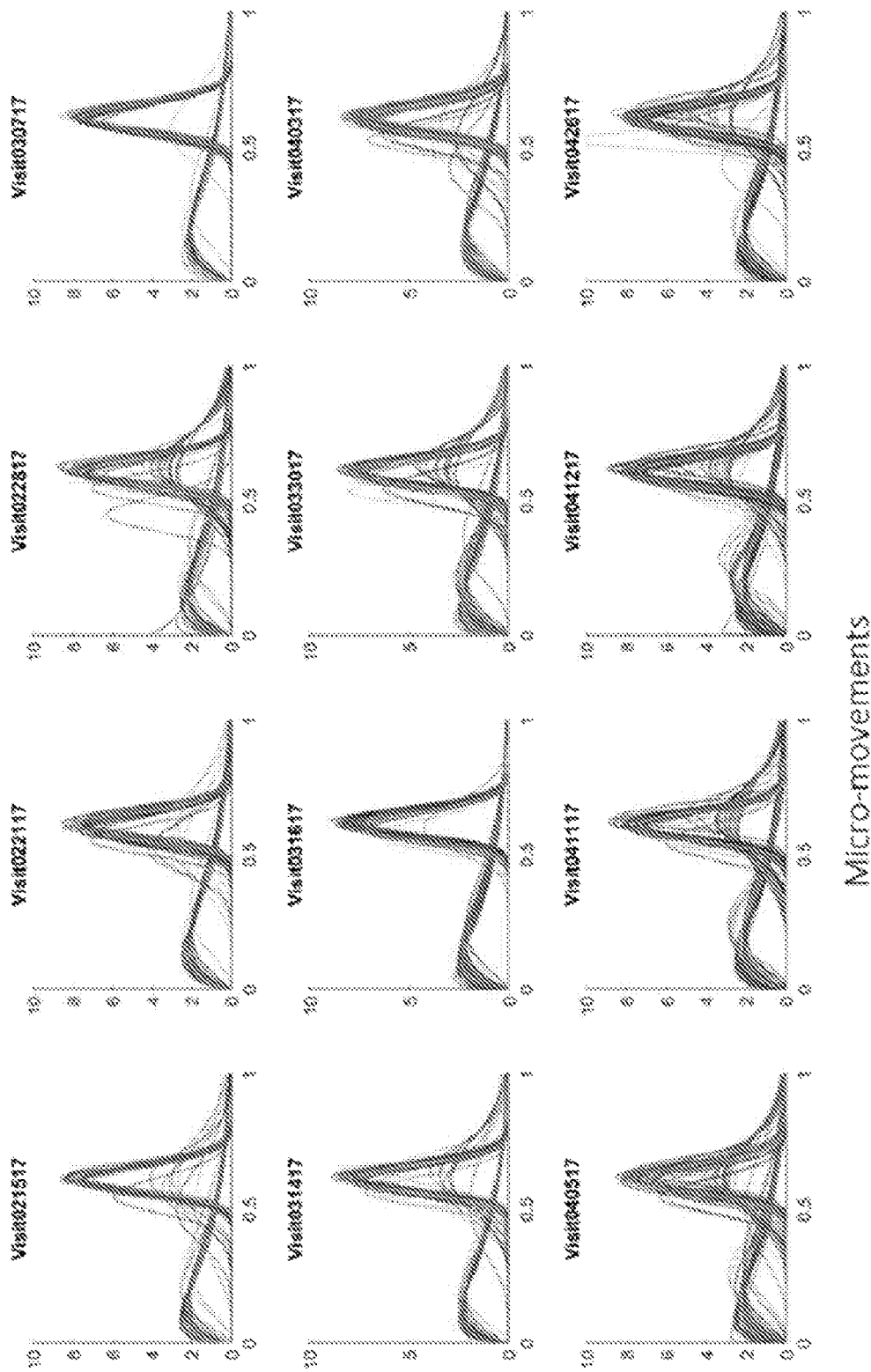
FIG. 21 illustrates an example of a longitudinal evolution of probability distribution families projected on the Gamma parameter planes for two complementary subspaces of degree of freedom statistical variability.

FIG. 21 shows samples of longitudinal evolution of probability distribution families projected on the Gamma parameter plane for the two complementary subspaces of DoF statistical variability. Distribution with lower dispersion and more symmetry are in the RLQ. In contrast, more skewed, noisier (flatter) distributions are in the LUQ of each Gamma parameter space at each lag plane.

Figures 22A, 22B, 22C, 22D:
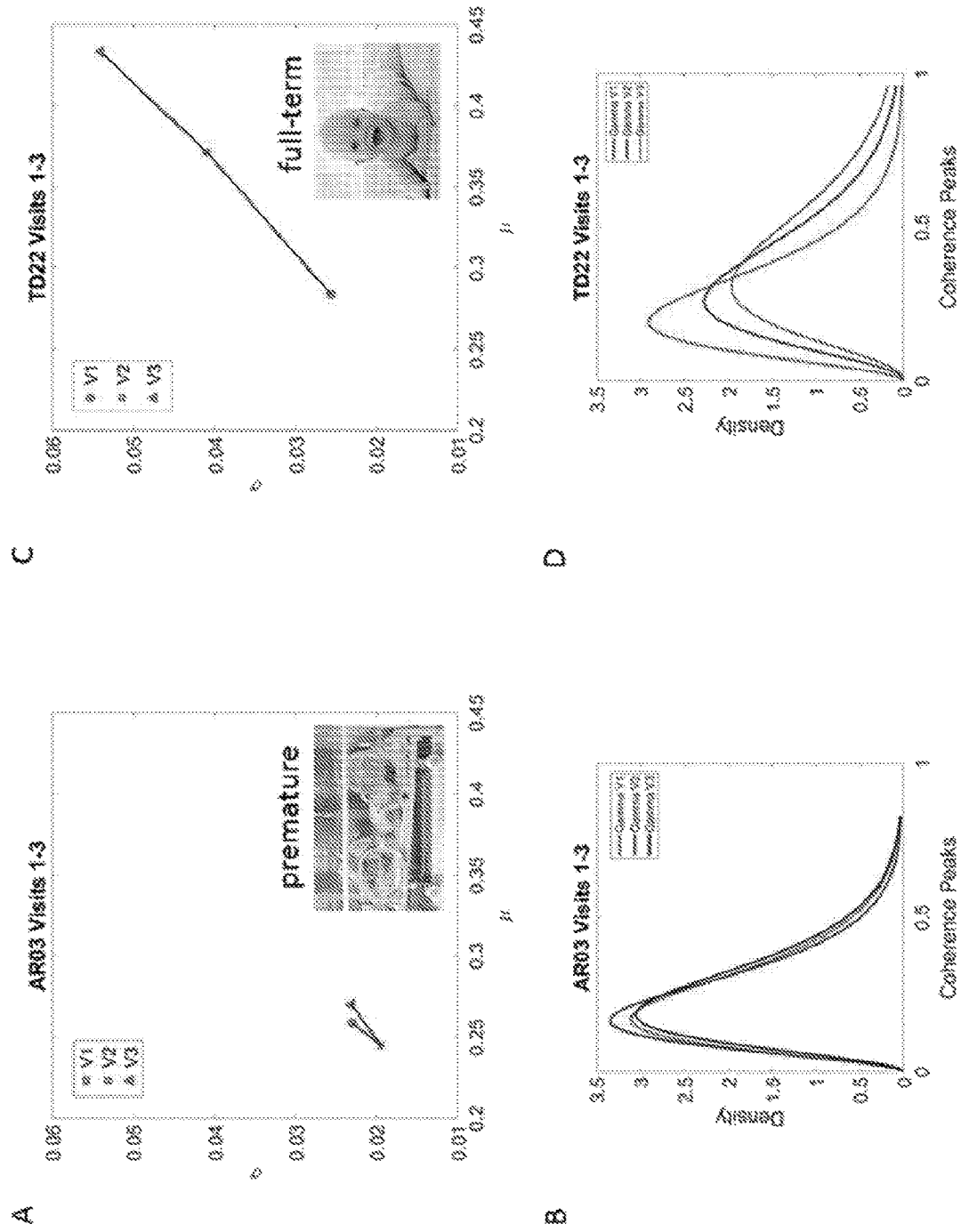
FIG. 22A through FIG. 22D illustrate examples of outcomes from representative babies in the premature and full-term samples.

FIG. 22 shows an example of an outcome from representative babies in the premature and full-term samples: (A) longitudinal tracking across 3 visits reveals stunting (very little change in coordination patterns between the two arms) for the premature baby born with complications; and (B) full term baby is clearly developing neuro-motor control. PDF family has a broader range of parameters. Here the metric is cross-coherence of the two arms' angular speed as they rhythmically entrain and fall out synchronous behavior. This is an index of coordination. This figure depicts the patterns obtained by examining the cross-coherence of the micro-movements extracted from the angular speed continuously recorded using the wearable sensors attached to the subject. The peaks of the cross-coherence are used to characterize a point process (as described above) as a Gamma process.

A greater understanding of the present invention and of its many advantages may be had from the following examples and case studies. The following examples are illustrative of the effectiveness of the described techniques to identify neurodevelopmental issues. They are not to be considered in any way limitative of the invention. Numerous changes and modifications can be made with respect to the invention.

Example: Personalized Index of Neurodevelopment at Risk in the Newborn

In the following, empirical evidence is provided that the degree of congruence between the rates of adaptation of noise-to-signal transitions in kinematics variables reflecting higher levels of control and those of physical growth is a good indicator of typical neurodevelopment in the newborn; and that the failure of this congruence to appear flags risk of neurodevelopmental derail.

Methods

Figures 6A, 6B, 6C:
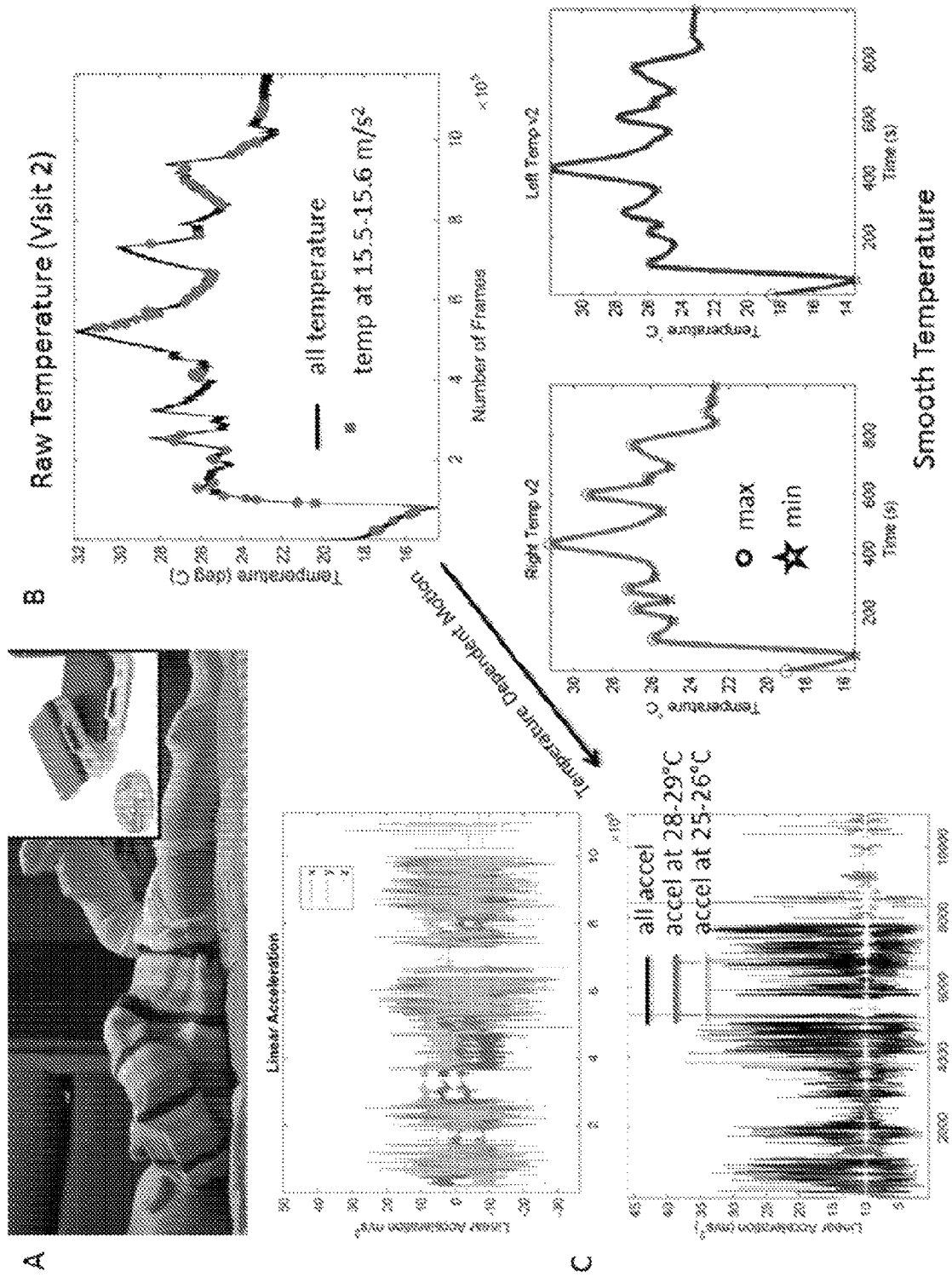
FIGS. 6A-6C illustrate data registration for an example case study.

A case study is shown in FIGS. 6A-6C and further explained below. FIG. 6A shows photographs of inertial measurement units (IMUs) that were used to register linear acceleration, orientation and temperature. FIG. 6B shows raw temperature traces for one of the visits (randomly chosen) with landmarks of occurrences of acceleration reaching between 15.5-15.6 m/s2 (number randomly chosen for explanation purposes only). Traces of the smooth temperature from the right and left sensors are shown with highlighted local minima and maxima. FIG. 6C shows linear acceleration traces from the x, y, z directional components and linear acceleration traces of the magnitude built using Euclidean norm. Traces are shown for acceleration ranges occurring for the 25-26° C.-interval and those occurring at 28-29° C.-interval (intervals randomly chosen within the temperature range to illustrate the notion of temperature-dependent motion).

Participants

Twelve infants with typical development (eight female, four male) control group (CT) and twenty-four infants (9 female, 15 male) pre-labeled clinically at risk (CAR) for developmental delay participated. Infants with typical development were from the Portland, Oreg. metropolitan area. Infants at risk for developmental delay were from the Los Angeles, Calif. metropolitan area and were identified as at risk according to the clinical definition of the state of California (California Department of Developmental Services. Retrieved Sep. 27, 2013, from https://www.dds.ca.gov/statutes/GOVSectionView.cfm?Section=95014.htm). This group includes, for example, infants born pre-term, with traumatic birth experiences, or with congenital heart defects. From this CAR group, it was anticipated that approximately half will have poor neuromotor outcomes (a diagnosis of developmental delay at 24 months) while half will have good neuromotor outcomes (no diagnosis of developmental delay at 24 months). The target developmental period was birth to walking onset (defined as onset of 3 independent steps).

Infants with typical development started the study between 1 and 8 months of chronological age while infants at risk started between 1 and 15 months' chronological age. All infants except for two were measured three times with approximately 2 months between visits, spanning nearly 4 months of their early development. Two infants were only measured twice as they started walking before the third scheduled measurement. The study was approved by the institutional Review Boards (IRB) of Oregon Health & Science University and the University of Southern California. Parents signed an informed consent form for their infants' participation. Rutgers University IRB approved data sharing agreements to properly examine the de-identified data.

Data Collection

At each visit the Alberta Infant Motor Scale (AIMS) was administered to the babies in order to quantify motor development status. Additionally, physical growth parameters were registered, including measurements of body length, body weight and head circumference. Inertial measurements units in wearable sensors (Opals, APDM, Inc., Portland, Oreg., USA) were placed in each leg using knee socks or custom leg warmers with pockets as shown in the photograph of FIG. 6A. Sensors were firmly attached with Velcro® to the bottom layer knee sock, proximal to each ankle joint and secured with a second knee sock. They synchronously collected triaxial acceleration, triaxial gyroscopic motions and temperature at 20 Hz continuously for 8-13 hours. Visits took place in the morning and the sensors remained in place during all typical activities of the day until bedtime. This was 8-13 hours after placement, when parents were instructed to remove them. Data were stored in the sensor's internal memory and downloaded later for analysis. Here, all hours of continuous motions were analyzed.

Statistical Analyes

A new data type was defined that integrates fluctuations in temperature readings with fluctuations in motor performance. This bundle of signals related to the autonomic and sensory-motor systems allows better exploration and identification of motion signatures that have the potential to be physiologically relevant to both the peripheral and central nervous systems (PNS and CNS).

The temperature and the motions (acceleration and gyroscopic) were simultaneously registered at the same sampling resolution, 128 Hz. The sensors output temperature readings related to several temperature types: skin surface temperature, ambient temperature, and temperature related to the battery's energy consumption indicative of the amount of actively generated motion output. The higher the amount of actively generated movements, the more battery energy is drawn, the higher the temperature is (on average). Yet, because there is also adaptation between the person's skin surface and the sensor's surface, the temperature readings fluctuate. Importantly temperature readings have been found to fluctuate differently if the person is actively vs. passively moving. Specifically, slow rate of change in temperature fluctuations correspond to passively generated motions (as when the person is moved and not generating large motions.) In contrast, actively self-generated motions, particularly those which are larger and more systematic, result in higher rates of change in temperature fluctuations.

These temperature fluctuations can be captured and analyzed to provide an indication of the amount of adaptive motion from self-generated movements that the individual wearing the sensors performs. Sample temperature fluctuations for one sensor are shown in FIG. 6B—these data were from continuously registered motions for over 8 hours. This figure illustrates the raw data along with the smoothed data, highlighting the maxima and minima of the waveform (smoothing shown in two plots of FIG. 6B achieved using standard MATLAB signal processing software, MATLAB Release 2014b, The MathWorks, Inc., Natick, Mass., US., which was executed on a computer).

Given a range of temperature, it is possible to isolate all the motion that takes place within that range because the signals from both instruments are synchronously registered at the same sampling resolution. For example, the dots in the Raw Temperature plot of FIG. 6B mark all the temperature registered for movements between 15.5-15.6 m/s². (These are arbitrarily selected for illustration purposes only.) FIG. 6C shows the acceleration computed from the triaxial traces, i.e., the magnitude of the acceleration vector giving the scalar quantity, $$acc = \sqrt{acc_x^2 + acc_y^2 + acc_z^2} \quad (1)$$

The terms in (Equation 1) are the components of the tri-dimensional acceleration vector.

Given the motion registered in some time period, it is also possible to determine movement segments occurring within a specific temperature range. For instance, the acceleration trace in FIG. 6C shows segments highlighted for specific temperature intervals between 28-29° C. and 25-26° C. (These are arbitrarily selected for illustration purposes only.)

Figures 7A, 7B, 7C:
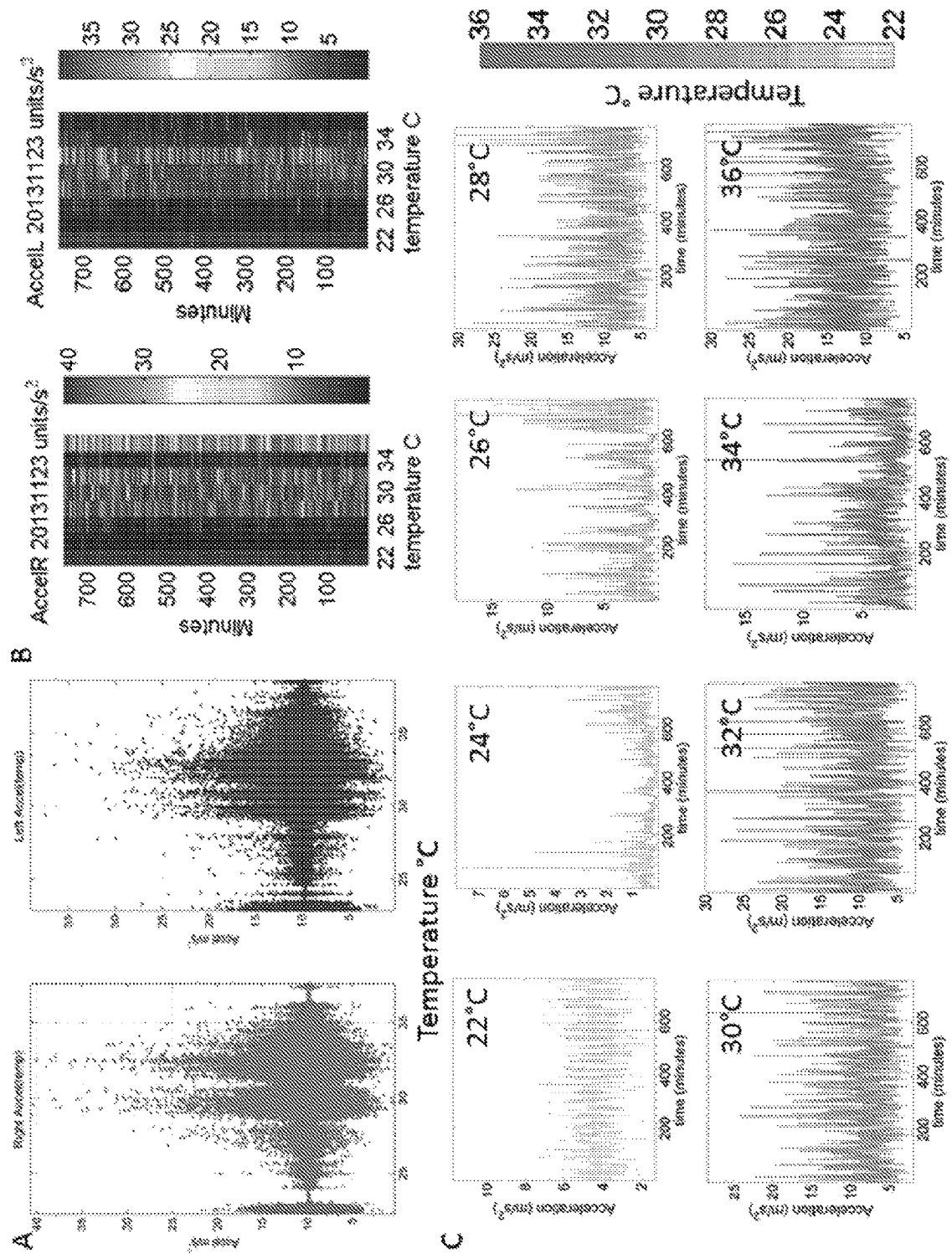
FIGS. 7A-7C illustrate examples of temperature-dependent motions captured from one or more sensors attached to a subject.

FIGS. 7A-7C illustrate methods to extract temperature-dependent motion for the example implementation for the number of minutes registered (e.g., 750 min, 12.5 hours). FIG. 7A shows the matrices for the two sensors gathering all the acceleration data as a function of temperature, allowing the selection of all the acceleration that takes place for each sensor for each temperature interval. In this example, the temperature interval is 2° C.-interval. FIG. 7B shows the color maps of these data in minute-by-minute matrices across 750 minutes demonstrating the maximal deviations from the mean acceleration in FIG. 7A for each of the sensors. The color bar highlights the range of m/s² values. Most data were at cooler temperatures. FIG. 7C breaks down the ranges of maximal deviation from the mean acceleration as time-series in the order in which they were registered for each 2° C.-interval (in ascending order of the color bar) for the right sensor. This panel also shows the range of temperatures in the color bar. For each of these acceleration regimes per temperature interval, the peaks were obtained to analyze the fluctuations in amplitude and timing. The stochastic analyses of fluctuations in amplitude forms the basis of aa new statistical platform for the personalized analyses of natural behaviors.

Statistical Platform for the Personalized Analyses of Natural Behaviors

The overall distribution of peaks across the data set can be obtained. The mean value empirically estimated and used as a reference to determine the maximal deviations from it. The time-series of these fluctuations in maximal deviations from the empirically estimated mean provides the waveform of interest for the analyses. Specifically, the system may determine the peaks of the waveform and derive spike trains representing random fluctuations in amplitude of the waveform. This is modeled as a continuous random process under the general rubric of Poisson Random Process. The spikes (coined micro-movements) are normalized to avoid possible allometry effects due to differences in the sizes of the limbs of the babies. These normalized fluctuations define the normalized micro-movements of the waveform.

To attain the normalization, for each segment between two minima, the normalized peak acceleration (NPeakAcc) is obtained:

$$NPeakACCC_{min\ to\ min} = \frac{PeakAcc_{min\ to\ min}}{PeakAcc_{min\ to\ min} + Avrg(Acc_{min\ to\ min})} \quad (2)$$

Larger values of this index indicate slower acceleration on average, since smaller averaged acceleration values in the denominator result in higher values of the index. These values across the same number of hours of recording, for each visit and each baby, were then gathered into a frequency histogram using any suitable method, such as an optimal binning algorithm by Freedman and Diaconis (1981) and Shimazaki and Shinomoto (2007).

For each minute of each hour (1,200 readings from 20 Hz×60) the time-series of normalized micro-movements serve as input to a Gamma process (a continuous random process represented by the continuous Gamma family of probability distributions.) To that end, maximum likelihood estimation (MLE) was used to estimate the parameters of the continuous Gamma family of probability distributions. Then, sweep was performed through the time series with a 1 minute block and a sliding window of variable size drawn from the continuous Gamma family of probability distributions to obtain a continuous stochastic trajectory while exploring present events within multiple scenarios of statistical co-dependency or independency from past events. The same number of hours were used for all babies (i.e., 8 hours).

Figure 8A:
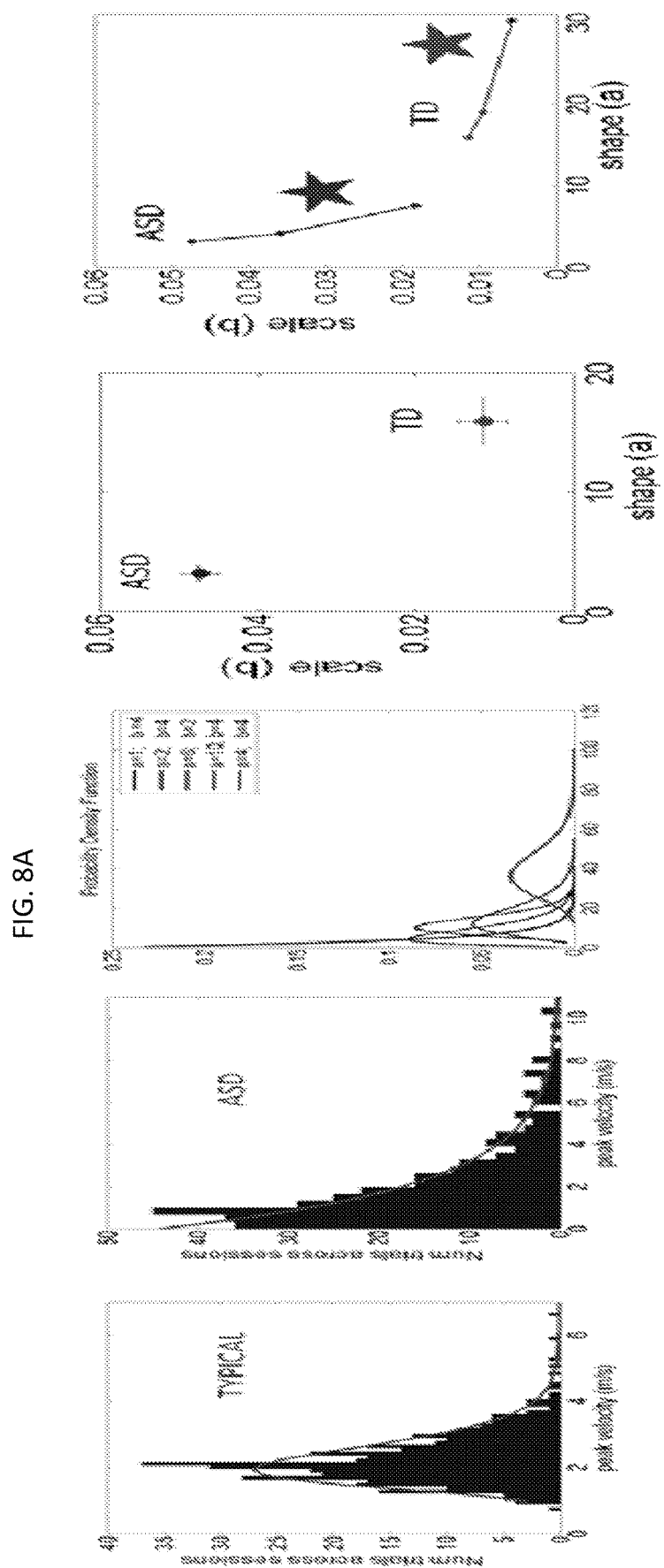
Figure 8B:
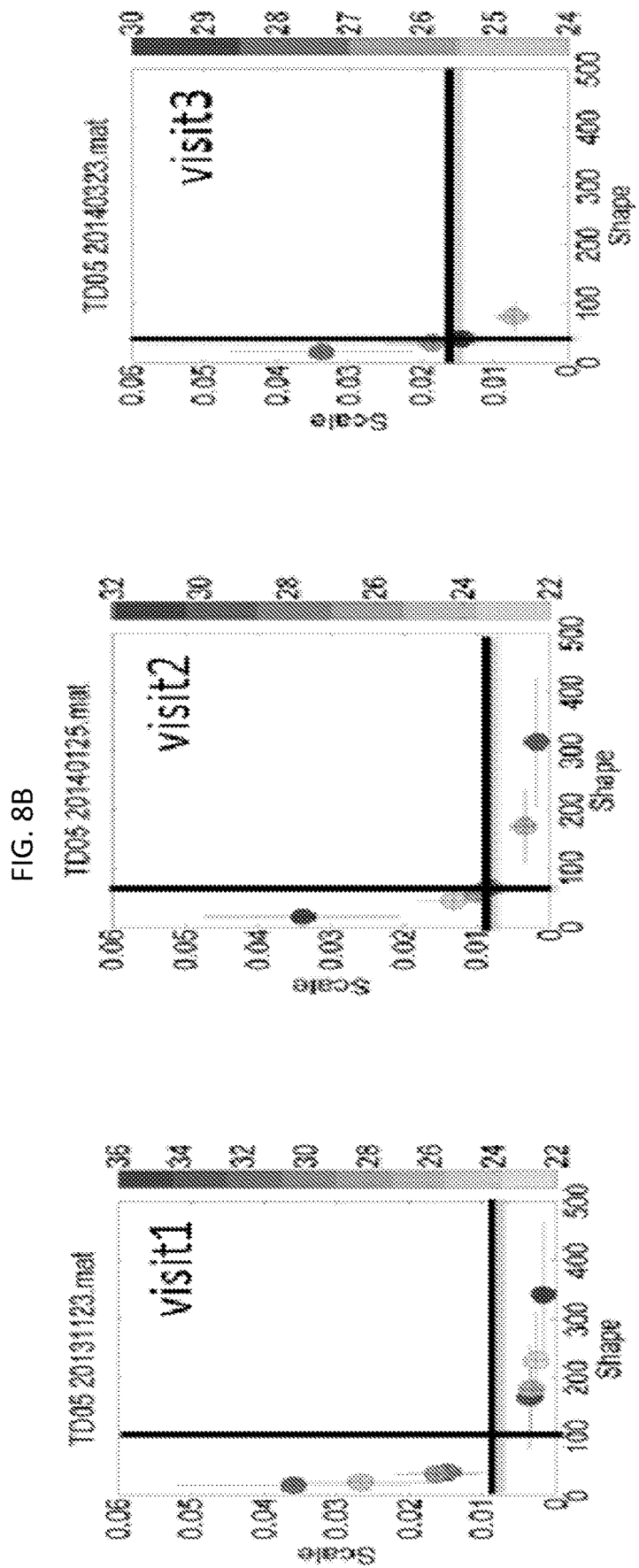

FIGS. 8A-8C illustrate methods of analyses for the example implementation. The points of the estimated trajectory were plotted on the Gamma parameter plane. Each point on this plane represents a probability distribution with estimated shape and scale parameter. These steps are illustrated in FIG. 8A. The first panel of this figure shows sample frequency histograms from typical (left) and atypical (right) data sets. The third panel shows sample estimated Gamma probability density functions (PDFs). The fourth panel represents the Gamma parameter plane with the two estimated points from the frequency histograms. The estimated shape and scale parameters were plotted with 95% confidence intervals for each estimated value. The last panel of FIG. 8A shows sample data points estimated in successive steps to illustrate their shifts over time, thus reflecting non-stationary feature of the data. The shifts occur at different rates. The stochastic trajectories these shifts give rise to are the center of the analyses as they track the changes in dispersion and shape of the distributions.

As shown in FIG. 8A, the first step is to measure the movements and extract the parameter of interest. In this case, they are the linear acceleration or the angular velocity continuously output by the sensors as a time series. The peaks are gathered into a frequency histogram and the maximal deviations from the empirically estimated mean are then normalized and gathered into a frequency histogram. The probability density function is then estimated using the maximum likelihood estimation (MLE) methods. In this case the continuous Gamma family of probability distributions is used to estimate the shape and scale parameters, plotted here on the Gamma parameter plane with 95% confidence intervals. The coordinates of the Gamma estimates on the Gamma parameter plane are tracked over time, as they shift along a stochastic trajectory across the 13 hours of recordings.

FIG. 8B shows examples from the three visits of one baby illustrating the steps in FIG. 8A. To track the evolution of the noise-to-signal transitions, the Gamma parameter plane is further divided into four quadrants using the medians of the family of estimated shape and scale parameters each day. The vertical line is the median across all estimated shape values. The horizontal line is the median across all estimated scale values. Each point is color coded (shown in grey-scale) according to the temperature value of the motion (color bar displays the full range for each visit). Each point on the Gamma plane is plotted with 95% confidence intervals for each of the temperature intervals depicted by the color bar. The median lines are obtained from the median shape and the median scale to divide the Gamma parameter plane into quadrants with the LUQ (high noise and more skewed distributions) vs. RLQ (low noise and less skewed distributions). As before, the color bar depicts the temperature regimes of the most relevant motion (maximal deviations from the mean).

FIG. 8C shows of the estimated PIMA corresponding to each temperature range in FIG. 8B. Further, since in the case of the Gamma distribution function, the scale value is also the noise-to-signal ratio (the Fano Factor), the fluctuations of this value are tracked over time:

$$FF = \frac{\hat{\sigma}_w^2}{\hat{\mu}_w} \quad (3)$$

In (Equation 3) the numerator denotes the estimated variance and the denominator denotes the estimate mean for the window of data in the time series. This noise-to-signal ratio is a measure of dispersion. The relation between the FF and the estimated scale Gamma parameter b is shown in equation (4):

$$b = \frac{\hat{\sigma}_w^2}{\hat{\mu}_w} = \frac{(a \cdot b^2)_w}{(a \cdot b)_w}. \qquad (4)$$

Tracking the Rates of Change of Adaptive Neuromotor Control: Noise-to-Signal Transitions on the Gamma Parameter Plane The Gamma parameters shift positions on the Gamma plane as they are re-estimated minute-by-minute. The non-stationary noise-to-signal ratio (FF) is tracked within a day over the course of 8 hours as the values transition between the left-upper quadrant (LUQ) and the Right Lower Quadrant (RLQ) of the Gamma parameter plane partitioned by the median values of the estimated shape and scale parameters. These noise-to-signal transitions are also tracked from visit to visit. Both the amplitude and the frequency of the transitions are tracked.

The RLQ contains the points with the lowest noise-to-signal ratio (lowest values of the estimated Gamma scale b-parameter). In contrast, the LUQ contains distributions with higher dispersion. Points in this LUQ have higher noise-to-signal ratio and are characterized by more skewed shapes tending towards the limiting case of the Gamma plane where the shape parameter has value 1. This is the case representing the "memoryless" Exponential distribution.

Figure 9:
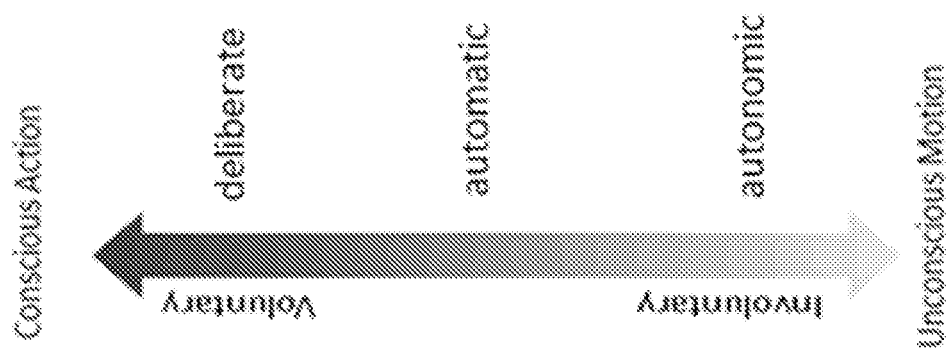
FIG. 9 shows an example of a taxonomy of neuro-motor control with phylogenetic order of developmental maturation.

The ΔN is defined as the maximal change in noise-to-signal ratio in one visit. This is the transition between quadrants with the largest amplitude. Using the temperature ranges within which the motion was registered, it is possible to further refine ΔN for each temperature interval. This ability to select motions within regimes of high-fluctuations in temperature provides additional information by more than one re-afferent source (acceleration and temperature) from different autonomic and sensory-motor systems (depicted in FIG. 9). FIG. 9 shows a proposed taxonomy of neuro-motor control. Referring to FIG. 9, different layers of control across the nervous systems appear in phylogenetic order from the bottom up. Information in each level can be registered non-invasively with modern instrumentation. The maturation of each layer of control transfers to the next layer as the baby develops. Their intertwined well-balance scaffolds the development of voluntary control of the bodily rhythms at will (volition). This is posited as a necessary ingredient to develop cognitive abilities.

Both types of fluctuations can be revealing of actively self-generated motions continuously feeding back to the baby's brain. Thus it is not just motion that is isolated by these methods. Rather, it is motion that has the potential to be physiologically relevant to the nervous system of the newborn. More precisely, the exchange of noise and signals associated with temperature fluctuations is monitored with an eye for higher regimes of temperature identified with actively self-generated motoric rhythms. Within those rhythms the frequency and the amplitude of the fluctuations tending to the RLQ and steadily converging to it are of interest in this work. They provide a sense of contrast between spontaneous random noise in the motions and actively generated signal.

Personalized Analyses:

Besides performing the type of ensemble analyses shown in FIGS. 8B and 8C, it is also possible to track the stochastic trajectories of each baby, i.e. in a personalized manner. In the previous method depicted in FIGS. 8B and 8C, given the temperature range (e.g. binned in 2° C. intervals) the corresponding motions were selectively assessed. As previously mentioned, it is also possible to track the motions and identify which temperature regimes the motion belongs to (as illustrated in FIG. 6C).

To this end, for each baby, the changes in noise-to-signal ratio were tracked in the motions using the above-mentioned 20 Hz×60 minute-by-minute block with the ½-minute sliding window. In addition, for each measurement, the corresponding temperature range within which this windowed motion was registered was obtained. An example of this method is shown in FIGS. 10A-10D for all three visits of one baby. In each case the median lines were plotted from the estimated Gamma parameters (as in FIG. 8B), obtained across the scatter of estimated values. The points in the scatter above or below the median values are color-coded by the temperature values for which that motion occurred.

Figure 10A:
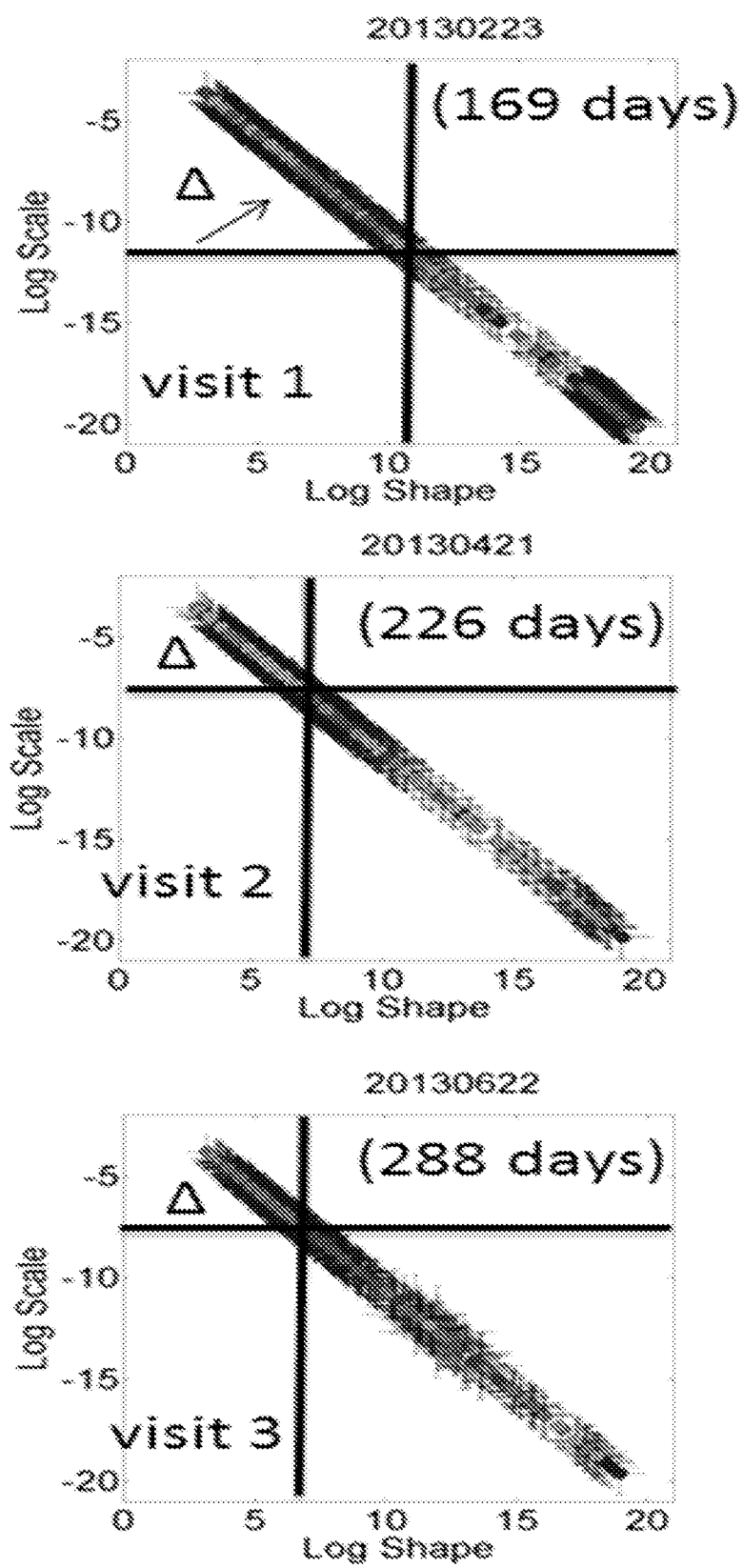
FIGS. 10A-10D illustrate the tracking of longitudinal shifts in noise levels in an example.
Figure 10B:
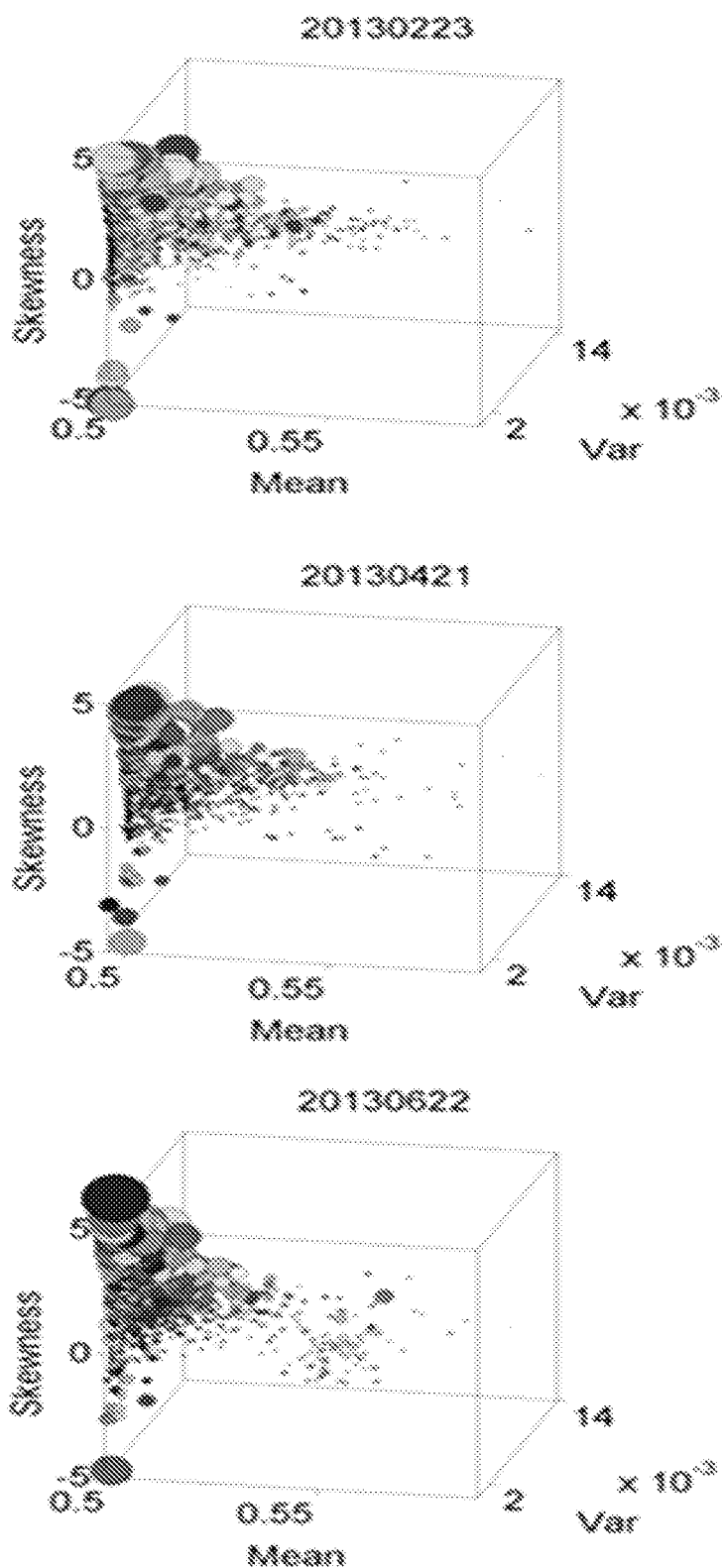
Figure 10C:
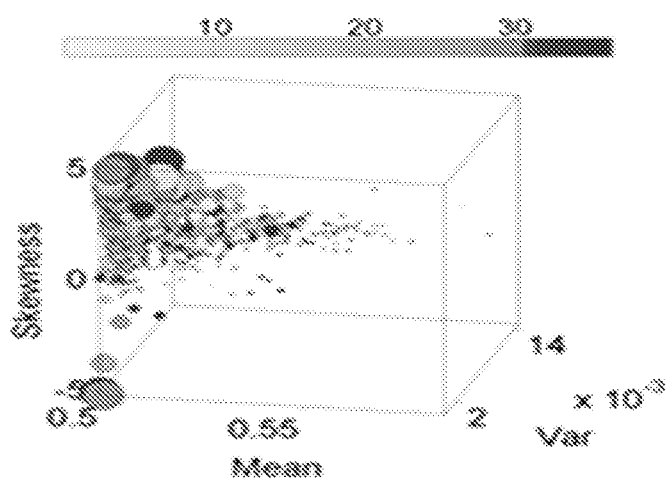
Figure 10C:
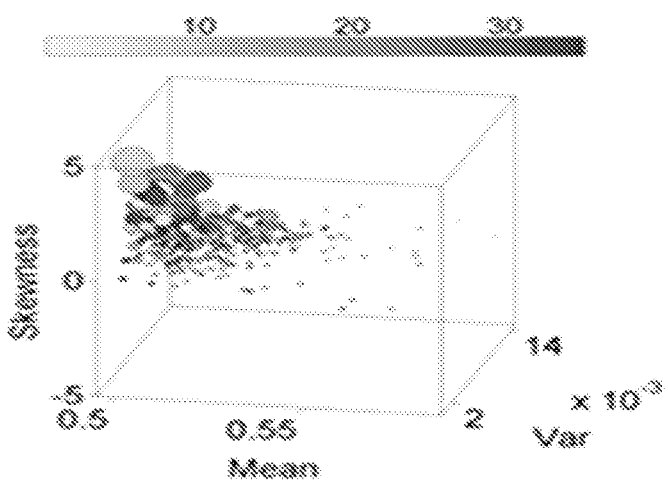
Figure 10C:
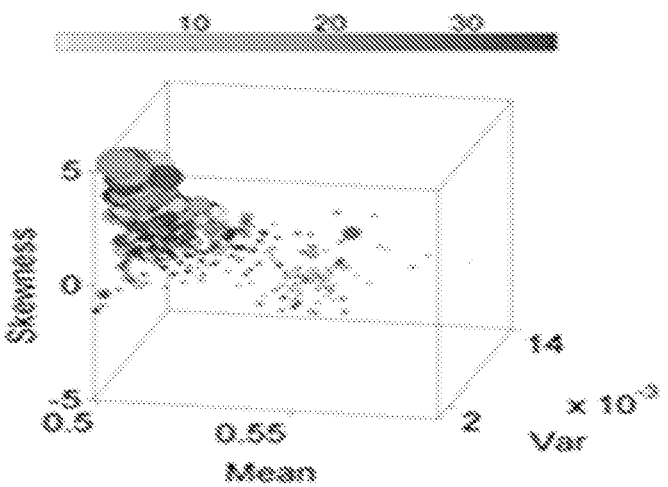
Figure 10D:
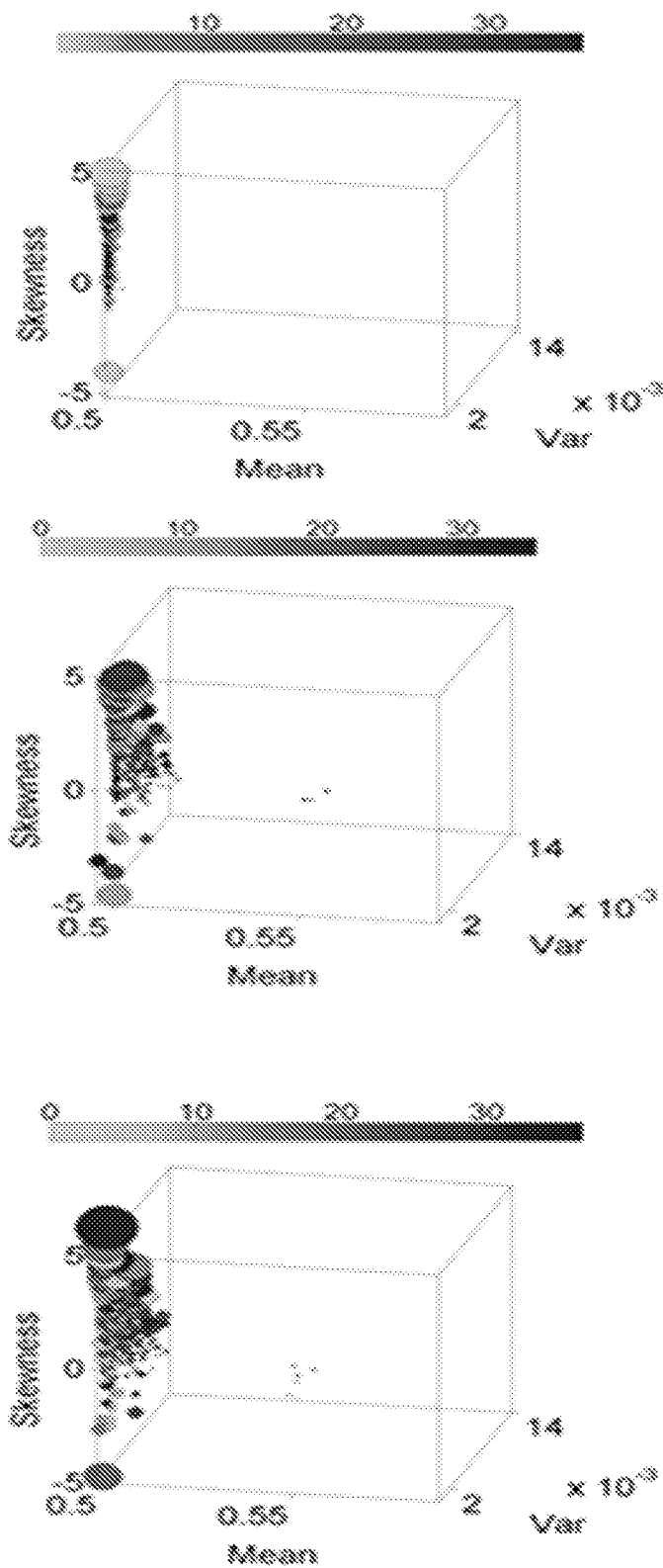

FIG. 10A shows sample stochastic maps that quantify the rates of change in noise evolution on the Gamma parameter plane for one (CT) baby across 3 visits spanning 4 months across infancy. Each plot is obtained from the motions registered in one visit with each point representing an estimation of 1,200 measurements (built with one-minute blocks, 20 Hz×60 values registered over the span of 8 hours.) Each colored circle represents the empirically estimated Gamma parameters obtained using MLE, plotted with 95% confidence intervals on the log-log Gamma parameter plane. The color represents the temperature range (see color bars on the three-dimensional plots) of the motion for which the noise range is tracked using the median of the values as a cutoff between higher and lower noise levels. Points above the median scale values (higher noise-to-signal values on the upper-left quadrant) are plotted in shades of one color, whereas those in the lower levels of noise (lower-right quadrant) are plotted in shades of another. FIG. 10B show five-dimensional scatter plots involving the estimated mean (x-axis), estimated variance (y-axis), the skewness (z-axis) and the kurtosis (the size of the marker) color-coded according to the median cutoff levels of noise (see text for details). FIGS. 10C and 10D show the separable evolution of the high and low noise levels across visits plotted along with their temperature ranges.

Panels across FIG. 10A show the log-log Gamma plane while those in the panel shown in FIG. 10B show the summary statistics in 4-dimensions (mean along the x-axis, variance along the y-axis, skewness along the z-axis and the size of the marker is the kurtosis). As in FIG. 8B the color map provides the range of temperatures for each noise level in the LUQ and RLQ points. In each case, the points from the RLQ below the median scale value and above the median shape value are plotted in shades of blue in the rightmost column D. The points corresponding to the LUQ are colored in shades of red in column C, according to the temperature values within which motions were registered. Panels in FIGS. 10C and 10D show them separately with the color bars depicting the corresponding temperature ranges for each scatter. They show the evolution from visit to visit of the noise-to-signal in each quadrant. Of interest here is how the RLQ is populated with darker shades indicating increasingly actively generated motions with high signal content (low noise to signal ratio) and a prevalence of symmetric distributions (skewness values around 3).

To compute the rate of change in noise for each visit, the estimated Gamma parameters are divided by the number of days since birth and up to that visit (shown on the LUQ of FIG. 10A). This provides a rate of change (incremental) measure of the stochastic signatures. Then the maximal amplitude change in noise-to-signal ratios ΔN is obtained for each visit by numerically differentiating and subtracting the minimum from the maximum across the LUQ and the RLQ. Likewise, the Δ(ΔN), which is the change in noise-to-signal transitions across the visit's stochastic trajectory, can be obtained This is the rate of change of adaptive neuromotor change of the infant in response to physical body growth from one visit to the next. In each of the computations represented in FIGS. 8A-8C and 10A-10D, the stochastic trajectories are obtained as the Gamma parameters move (non-stationary estimates) across the hours of the day.

Noise-to-Signal Transitions:

During the various hours of data registration the stochastic signatures of the motion-temperature signals may be at times non-stationary. As explained above, the noise-to-signal transitions between the LUQ and the RLQ are tracked. Specifically, the magnitude of the transition as well as the frequency of those transitions from one quadrant to the other are tracked.

Figures 11A, 11B, 11C:
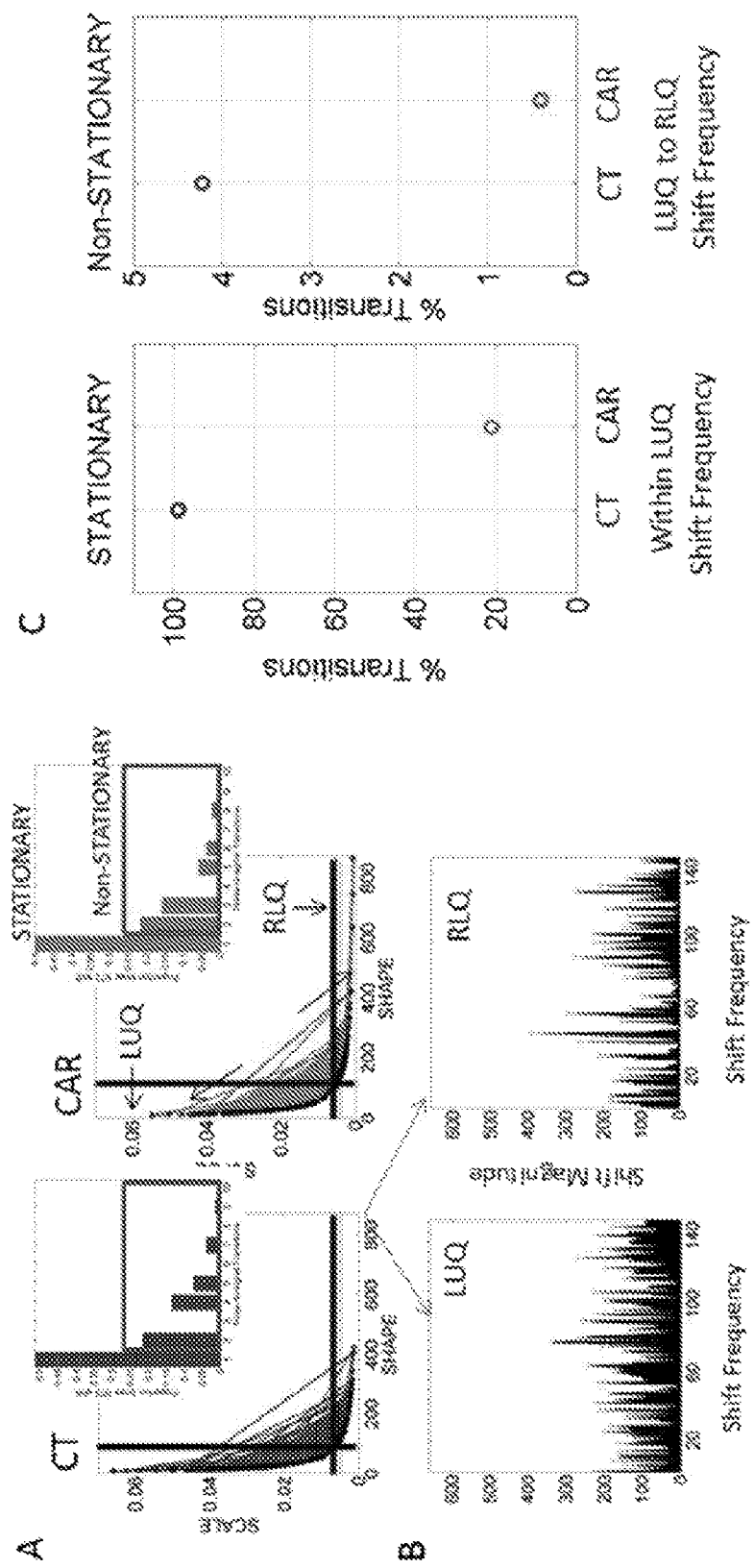
FIGS. 11A-11C illustrate the tracking of the rate of adaptive change through the noise-to-signal transitions on the Gamma plane in an example.

FIGS. 11A-11C illustrate the tracking of the rate of adaptive change through the noise-to-signal transitions on the Gamma plane of an example implementation. To determine the magnitude of the transition between quadrants, the norm of the difference between the estimated (shape, scale) vector at time t+1 and that at time t are computed. For all transitions, a temporal profile of these magnitude values is obtained (in the order in which they were obtained), Examples of these profiles are shown in FIG. 11B for a representative CT baby with stochastic trajectories (left plot of FIG. 11A). The stochastic trajectories for a representative CAR baby are shown in the right plot of FIG. 11A.

Maximum Magnitude of the Shift:

To obtain the time series of shifts in Gamma-parameters, the norm of the vector difference on the Gamma plane was computed (e.g. FIG. 11B shows those magnitudes for the CT baby trajectories). Then, the maximum shift amplitude can be obtained over all shifts between quadrants. To this end, the point in RLQ with the minimum scale value and the maximum shape value (i.e. the PDF with minimum noise-to-signal ratio and maximal symmetric shape) is subtracted from the point in LUQ with the maximum scale value and minimum shape value (i.e. the PDF with maximum noise-to-signal ratio and most skewed shape). The magnitude of the resulting vector on the Gamma parameter plane is then obtained using Euclidean norm.

Frequency of the Shifts:

To determine the frequency of transitions two types of transitions were examined. One is within a given quadrant (the LUQ or the RLQ). These inner-quadrant transitions are referred to as 'stationary'. The other is between the two quadrants. These inter-quadrant transitions are referred to as 'non-stationary'. To this end, the median-ranked selection criteria of the points that belong to each quadrant are used. For example, the LUQ points are those above the median scale and below the median shape. The order of the indexes into these points tells the history in the frequency of change in the stochastic signatures, i.e. as they remained within the same quadrant, or as they jumped successively from one quadrant to the other.

The two arrays containing such indexes for the LUQ and RLQ are numerically differentiated to count the number of instances when the change was consecutive within one quadrant (i.e. the difference from one shift to another is 1). In contrast, differences from one shift to another that are greater than 1 denote instances when the shifting is from one quadrant to another. For example, if the indexes array for the points in the LUQ has values [1, 2, 3, 4, 6, 9, 10, 11], then the difference array will be [1, 1, 1, 2, 3, 1, 1]. This means that the process remained stationary in the LUQ for three consecutive times, then jumped to the RLQ, jumping 2 instances and then came back to the LUQ and returned to the RLQ where it jumped three instances before it came back to the LUQ two more consecutive times.

These instances were gathered in a histogram and each bin was normalized by the number of occurrences to obtain the distribution of noise-to-signal transitions and the proportion of times spent in each quadrant of high or low noise along with the proportion of shifts. Then, the percentages of stationary and non-stationary transitions were computed for each baby. FIG. 11C shows the percent frequency of the shifts for each representative CAR and CT baby quantified within a given quadrant (the LUQ in this case) and between quadrants (from the LUQ to the RLQ in this case) denoting stationary and non-stationary shifts respectively. These quantities are the averaged percent values across the three visits. The insets in FIG. 11A show the histograms of the proportions of times in the stationary and non-stationary states with respect to the LUQ for each baby type. Notice that in this FIG. 11C example the CAR baby does not transition much in relation to the CT baby in either of the stationary and non-stationary states.

Summary or Roadmap of the Analyses

There were three types of analyses conducted. First, the ensemble behavior of each clinical group of the typical babies and the group at risk according to their clinical label (CAR) was computed. Since the two groups had disparate sizes (CT 12) and (CAR 24), 12/24 were randomly chosen with no replacement until the CAR group was exhausted. Using these clinically pre-labeled groups, the temperature fluctuations in each group and the physical growth parameters reported for each baby in each group were examined. In addition, the stochastic signatures and their shift or lack thereof were also examined for these cases.

The second set of analyses was performed on the whole ensemble without considering the clinical labels (CT and CAR). The motivation here was to unveil automatically self-emerging clusters based on the objective physical growth data in order to guide the classification of the underlying noise-to-signal data extracted from the motion sensors registering leg movement rhythms. For this second analyses, the physical parameters were first obtained for each individual baby (i.e. the body length, the body weight, the head circumference) as well as their individual rates of change computed by dividing the value of the parameter each visit by the number of days since birth until the day of the visit. Similarly, the rate of change of the AIMS total scores was examined. For each of the three dimensions of the rates of change in physical parameters the median was obtained and the data ranked. To this end, the three-dimensional median vector determined the cutoff of the first group of babies, those babies with the highest rate of change in each of the parameters of physical growth. This group had the highest median value for body length and weight and head circumference. The same operation was performed on the remaining group and a second subgroup obtained, ranked as well according to the median cutoff of that remaining group. This median-cutoff selection was done once more and at the end of the process 4 ranked groups were obtained. Secondly, a Delaunay triangulation was performed on the scatter of each group to draw the corresponding surfaces and examine the underlying changes in the amplitude and the frequency of noise to signal transitions. This individualized analyses also entailed examinations of the rates of change in total AIMS scores so as to gain insights into the motor readiness of each ranked group, as well as to help visualize the physical growth rate of change data.

The third set of analyses involved the use of the stochastic signatures of acceleration obtained within each temperature range. The averaged $\Delta N$ in a visit was expressed as a rate of change (by dividing the $\Delta N$ by the number of days since birth till the day of the visit of each baby). This quantity was expressed as a function of the averaged $\Delta$Physical growth parameter, taken as well as a rate of change across visits. The latter included averaged $\Delta$body-length across visits (cm/day); $\Delta$body-weight across visits (kg/day); averaged $\Delta$head-circumference across visits (cm/day). This analysis automatically yielded a group of babies statistically at high risk (denoted HR). The median statistic to rank that data was the only heuristic applied. This method was appropriate given the skewed nature of the families of probability distributions underlying both the rates of change in physical growth and the rates of change in the noise-to-signal transitions of the motor fluctuations data. Babies in the first ranked group were denoted typically developing (TD) based on the statistical ranking (rather than on the clinical criteria). Those in the second and third group merged into the partially at-risk group (PAR) and the remaining last ranked group HR. The PAR group was comprised by babies ranked 2 and 3 according to the median-ranking criterion for the rate of change in physical growth.

Results

Ensemble Data Shows Fundamental Differences in the Rates of Chance of Temperature-Dependent Fluctuations in Motor Performance of Clinically Pre-Labeled Baby Types The groups pre-labeled CT and CAR yielded significantly different distributions of fluctuations in temperature according to the Kolmogorov test for empirical distributions, right sensor data $p<1.5\times10^{-29}$, left sensor data $p<7.4\times10^{-29}$. This difference can be appreciated as well in the empirical cumulative distribution function (eCDF), the probability distribution function (PDF) and the probability plots of FIGS. 12A-12C respectively for the data of the sensors positioned on both legs. No differences between the signatures of the left and right legs were noted within each group ($p>0.9$ rank sum Wilcoxon test).

The ensemble data from the distributional analyses was also examined for the pre-labeled groups. Differences emerged in the ranges of temperatures within which the babies' motions were registered. Specifically, the CT infants had higher values in the centroid than the CAR babies (34° C. CT vs. 28° C. CAR) as can be appreciated in FIG. 12A,
center. The summary statistics from the estimated stochastic signature analyses also revealed differences between the two groups. Specifically, the skewness was the moment that maximally separated the two groups (mean comparison $\bar{p}<0.04$, based on a comparison of the third moment).

Figures 12A, 12B, 12C, 12D, 12E:
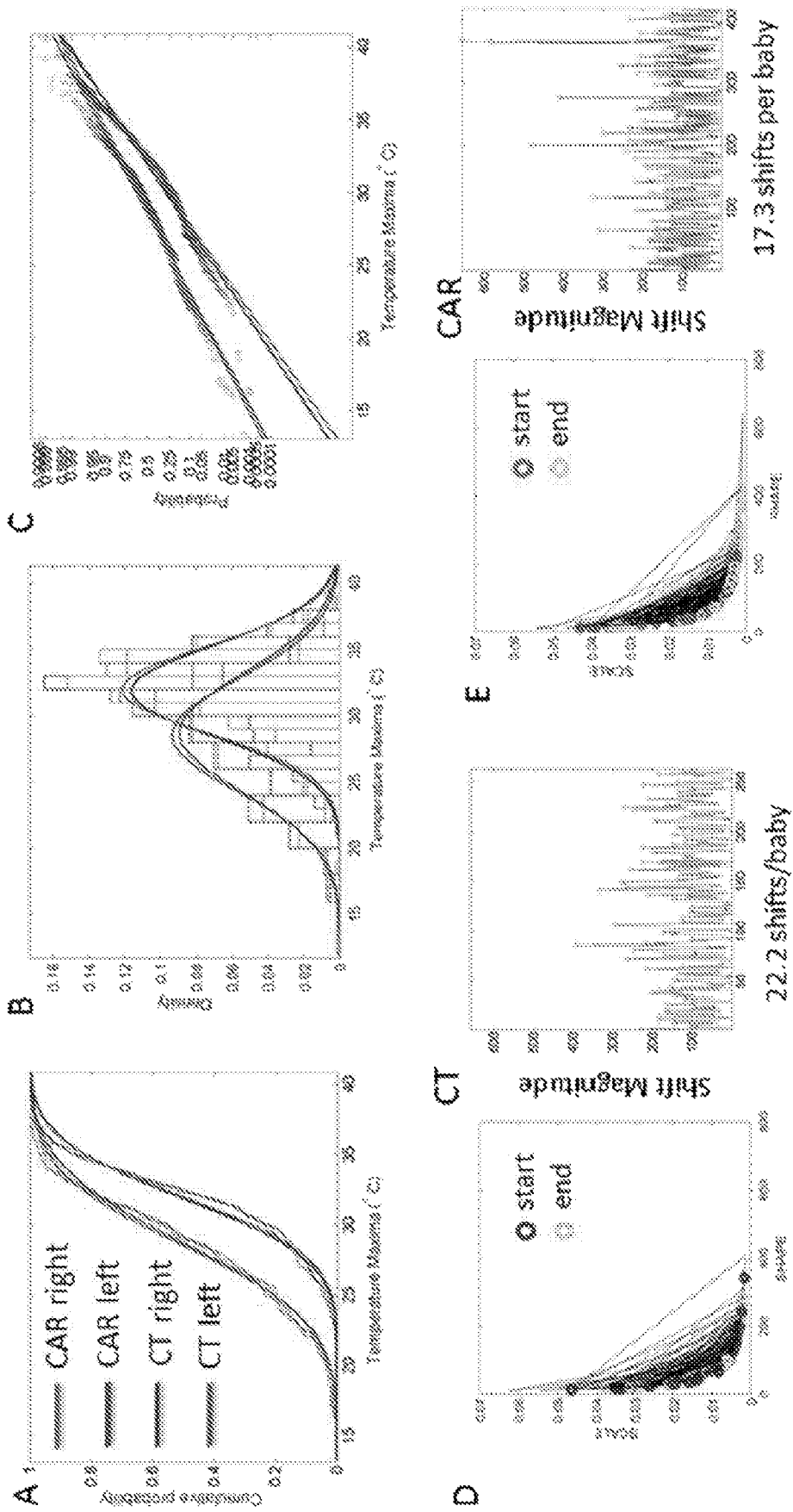
FIGS. 12A-12E illustrate differences between the groups based on birth status for an example of case study.

FIGS. 12D and 12E show the stochastic trajectories across babies of each pre-labeled group along with the frequency of shifts between the left upper quadrant (LUQ) and the right lower quadrant (RLQ) of the Gamma parameter plane, as determined by the median values of the estimated shape and scaled Gamma parameters. The CT group displayed higher frequency of shifts overall. This lower frequency of noise-to-signal transitions in the CAR group prompted further exploration regarding the inner-quadrant transitions (stationary) vs. the inter-quadrant transitions (non-stationary). To that end, in a subsequent section the babies were assessed individually and blindly, without a priori labels in search of self-emerging patterns.

Figure 13A:
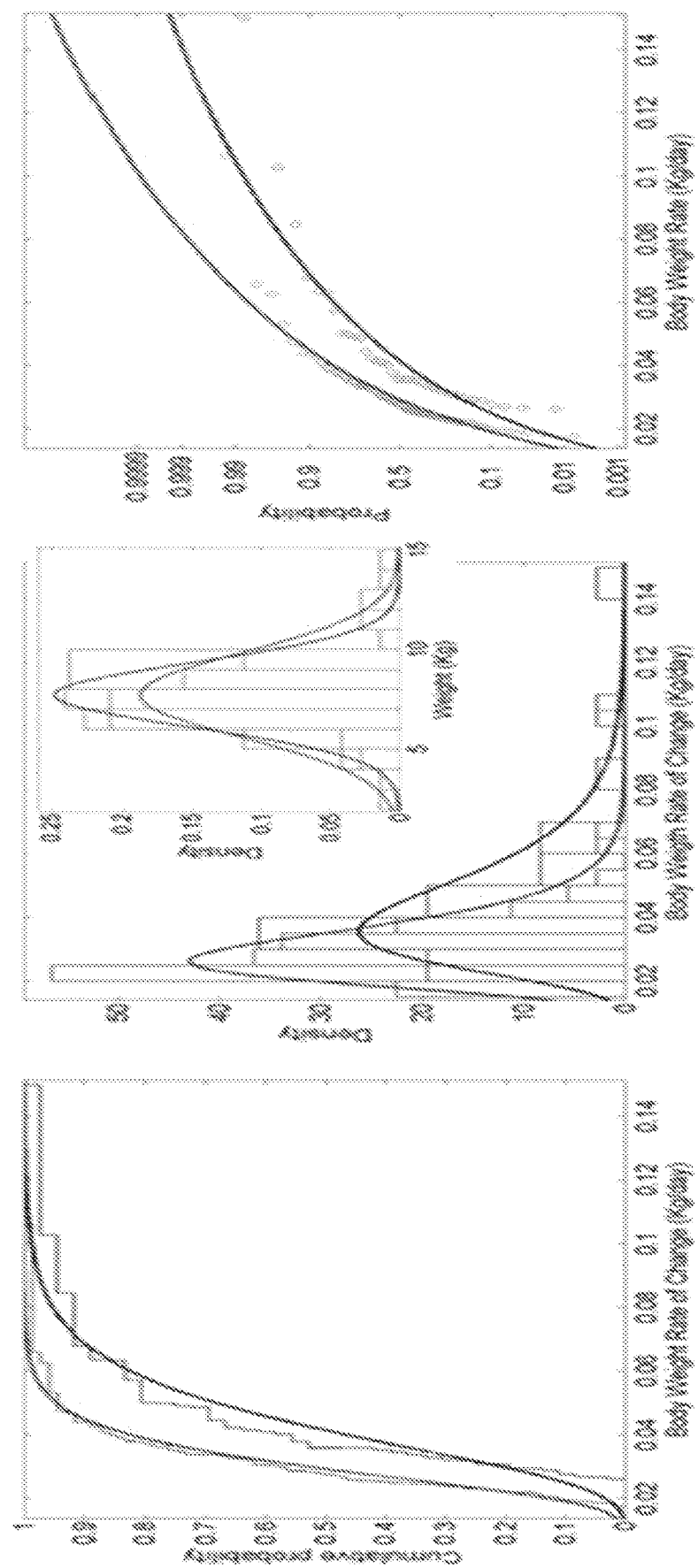
Figure 13B:
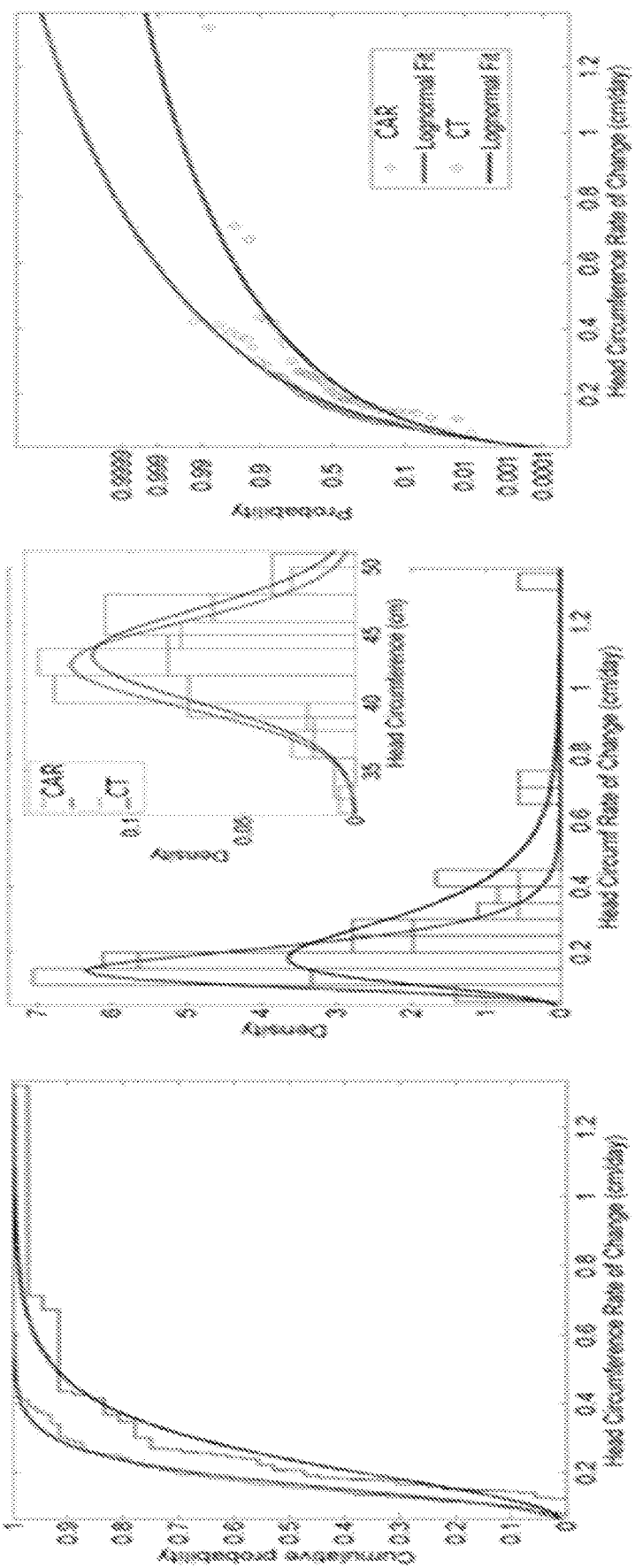

Incremental Rates of Physical Growth Rather than their Absolute Values Reveal Dramatic Differences Between Full-Term and Pre-Term Babies The absolute data reflecting the measurement of physical parameters in each visit was pooled across each group. This yielded frequency histograms that were well fit by the symmetric normal distribution. This can be appreciated in FIGS. 13A-13C (in the middle column insets) for each physical growth parameter. In FIGS. 13A-13C, the left-most panel shows the empirical cumulative distributions of body weight, head circumference and body length respectively. Data are taken incrementally as a rate of change from the day of birth until the visit day (all 3 visits data pooled across all CT, one curve and all data pooled across all CAR babies, another curve). Middle panels contain the same data in probability density format and right-most panels are in probability-plot format. In all, the incremental data is well fit by the theoretical lognormal distribution shown by the smooth curve. Central panel insets show the frequency histograms of the absolute values of physical parameters currently in use by many pediatricians and referenced to growth charts of absolute values from normative data based on the normal distribution (see Table 3 for further details on statistical comparisons). No significant differences were found for absolute values between the groups according to the rank sum Wilcoxon test on the medians. This is reported in Table 1 (below). In marked contrast to the absolute values recorded each visit, the incremental data across visits yielded frequency histograms that were well fit by the lognormal distribution. They were skewed with long tails to the right and high statistically significant differences were found according to the rank sum Wilcoxon test on the medians. This is reported in Table 1 (below) as well. The physical growth rate of change data is displayed in FIGS. 13A-13C using the eCDF, PDF and probability-plots formats.

TABLE 1

Results ensemble stats (temperature dependent motion data)

| | Source | SS | df | MS | Chi-sq | Prob > Chi-sq |
|---|---|---|---|---|---|---|
| CT | Columns | 400.22 | 2 | 200.111 | 6.37 | 0.04 |
| | Error | 1233.78 | 36 (3 visits) | 51.407 | | |
| | Total | 1634 | 34 | | | |
| CAR | Columns | 24.97 | 2 | 12.487 | 0.09 | 0.9556 |
| | Error | 15387.03 | 70 (22 × 3 visits and 2 × 2visits) | 284.945 | | |
| | Total | 15412 | 68 | | | |

Lastly, Table 2 (below) reports the AIMS scores and the statistical comparisons for absolute values and incremental data. The former had mixed results with some scores showing statistical differences and others not showing the differences between the two groups. In contrast, the incremental AIMS data were more revealing of the differences (as in the rate of growth for each group under examination). These differences were all highly significant when using the rates of change since birth, rather than the actual values registered in each of the visits.

the slowest rate of change. Delaunay triangulation on the scatter of each median ranked group was used to determine the surface best fitting each cluster. FIG. 14A shows the 4 clusters (referred to as Rank 1-4) arranged using the Delaunay surfaces with the x-axis to represent the rate of change in weight (kg/day), the y-axis to represent the rate of change in body length (cm/day) and the z-axis as the rate of change of the total AIMS scores per day. The figure also contains the information on the rate of change in the head circumference (cm/day) plotted as the size of the marker. CT babies and

TABLE 2

| Results ensemble stats (growth data) | | |
|---|---|---|
| Parameter (absolute value) | Mean and Variance (Normal PDF) [mean, var] | Comparison Wilcoxon rank sum test (p-value) |
| Weight (Kg) | CAR [7.71225, 4.57677] CT [7.71417, 2.60401] | 0.4231 |
| Head Circumference (cm) | CAR [42.8155, 9.9399] CT [43.5032, 12.234] | 0.2750 |
| Body length (cm) | CAR [67.3408, 44.2836] CT [66.7217, 30.1483] | 0.4681 |
| Parameter ($\Delta$ since birth) | Mean and Variance (Lognormal PDF) [mean var] | Comparison Wilcoxon rank sum test (p-value) |
| Weight (Kg/day) | CAR [0.0309341, 0.0001137] CT [0.0448418, 0.0003427] | 4.5270e−06 |
| Head Circumference (cm/day) | CAR [0.182559, 0.00595036] CT [0.274164, 0.0238794] | 7.1014e−04 |
| Body length (cm/day) | CAR [0.284353, 0.0130271] CT [0.418218, 0.0531367] | 0.0015 |
| AIMS scores (absolute values) | Mean and Variance (Normal PDF) [mean, var] | Comparison Wilcoxon rank sum test (p-value) |
| Total | CAR [23.2817, 214.09] CT [29.2778, 206.206] | 0.0288 |
| Prone | CAR [8.30986, 42.9883] CT [11.5556, 35.9111] | 0.0074 |
| Supine | CAR [6.38028, 5.66761] CT [7.38889, 4.24444] | 0.0341 |
| Sitting | CAR [5.42254, 15.1618] CT [6.61111, 18.073] | 0.1883 |
| Standing | CAR [3.16901, 8.9996] CT [3.72222, 9.40635] | 0.1187 |
| AIMS scores (rate of change/day since birth) | Mean and Variance (Lognormal PDF) [mean, var] | Comparison Wilcoxon rank sum test (p-value) |
| Total | CAR [0.082312, 0.00137389] CT [0.140831, 0.00089313] | 1.1916e−11 |
| Prone | CAR [0.0295296, 0.000435786] CT [0.0541267, 0.000169476] | 1.6701e−10 |
| Supine | CAR [0.0246442, 8.12808e−05] CT [0.0409908, 0.00020606] | 1.5132e−09 |
| Sitting | CAR [0.0183238, 0.000123955] CT [0.0318401, 0.000152011] | 4.1693e−05 |
| Standing | CAR [0.0110414, 4.0511e−05] CT [0.0174758, 8.00733e−05] | 9.8285e−06 |

These results on the rates of change of physical growth, motor readiness scores along with those from the previous section involving the differences in fluctuations in temperature and motor performance, prompted the examination of the cohort without a priori clinical labels in search for self-emerging rather than assumed groups.

Babies Automatically Group According to their Rates of Change in Physical Growth The iterative ranking of the median values across all rates of change in physical growth parameters (see Methods) yielded 4 groups sorted from highest to lowest rate of change. Babies in the first group were the most advanced in their rate of growth. Babies in the last group were those with CAR babies were identified on the plot. Interestingly, two CAR babies were included in Rank 1, a mix of CT and CAR were found in Rank 2 and Rank 3, and CAR babies make up the Rank 4. As can be seen from FIG. 14A, the surface representing the babies with the fastest rate of physical growth is oriented differently from the other surfaces. In this sense, the last cluster representing the lowest rate of change of physical growth across all parameters was composed of CAR babies and is oriented nearly orthogonal to the Rank 1 surface. This Rank 4 group is rendered by the ranking as the statistically at high risk (HR) babies. Partially at risk (PAR) babies are those in Rank 2 and Rank 3, whereas Rank 1 are denoted typically developing (TD). The compositions of each Group along with the ranges of the rates of change of physical growth for each group and the temperature ranges are reported in Table 3 below.

TABLE 3

Estimated parameter ranges

| Physical Growth Ranking | ΔPhysical growth, Δweight, Δbody-length, Δhead circumf, ΔAIMS | Ranges Estimated μ, σ², sk, kt from Norm MaxAcc | Mean Temperature/ visit |
|---|---|---|---|
| TD02 | 0.0336, 0.3067, 0.2011, 0.1204 | 0.4922 0.6029; 0.0000 0.0151; −5.8394 5.5892; 1.4933 37.1442 | 33 31 31 |
| TD05 | 0.0306, 0.3369, 0.2213, 0.0655 | 0.4979 0.5912; 0.0000 0.0170; −5.1801 6.0122; 1.5303; 38.3716 | 32 30 32 |
| TD09 | 0.0211, 0.2067, 0.1259, 0.0497 | 0.4920 0.58 2; 0.0000 0.0139; −5.2404 5.9818; 1.5586 38.1043 | 30 27 31 |
| TD10 | 0.0304, 0.3003, 0.1998, 0.0545 | 0.4806 0.6550; 0.0000 0.0203; −5.0611 5.9364; 1.5428 36.5140 | 32 28 30 |
| TD11 | 0.0306, 0.2268, 0.1369, 0.0449 | 0.4950 0.5706; 0.0000 0.0156 −5.3382 6.1202; 1.6040 38.6636 | 26 29 30 |
| TD12 | 0.0388, 0.3465, 0.2308, 0.1081 | 0.4805 0.6040; 0.0000 0.0241 −5.1968 5.8017; 1.3588 42.2956 | 24 29 27 |
| AR11 | 0.0249, 0.2426, 0.1545, 0.0899 | 0.4952 0.5879; 0.0000 0.0175 −5.1872 6.2760; 1.5233 42.5557 | 28 29 31 |
| AR26 | 0.0423, 0.4470, 0.2651, 0.1233 | 0.4937 0.6062; 0.0000 0.0166 −4.6174 5.4958; 1.3735 32.7174 | 27 28 29 |
| TD01 | 0.0513, 0.4684, 0.3146 0.1494 | 0.4966 0.6152; 0.0000 0.0214 −5.0672 5.7469; 1.5407 35.9470 | 31 32 32 |
| TD03 | 0.0420, 0.3145, 0.2146 0.1455 | 0.4914 0.5746; 0.0000 0.0129 −4.8887 5.8321; 1.3109 35.0186 | 31 31 31 |
| TD06 | 0.0232, 0.1730, 0.1133, 0.1256 | 0.4957 0.5925; 0.0000 0.0261 −5.2723 5.9838; 1.5056 37.2169 | 31 32 31 |
| TD08 | 0.0514, 0.4573, 0.2895 0.1305 | 0.4964 0.5814; 0.0000 0.0141; −5.6104 6.8170; 1.3318 51.2641 | 31 31 31 |
| TD04 | 0.0247, 0.2561, 0.1682, 0.0514 | 0.4875 0.5647; 0.0000 0.0082 −5.0714 5.9913; 1.3845 42.1141 | 26 25 29 |
| AR24 | 0.0349, 0.3925, 0.2757 0.0562 | 0.4960 0.5640; 0.0000 0.0084 −4.7638 5.9219; 1.5891 40.6918 | 30 33 33 |
| AR10 | 0.0370, 0.3510, 0.2318 0.0614 | 0.4960 0.5640; 0.0000 0.0084 −4.7638 5.9219; 1.5891 40.6918 | 30 33 33 |
| AR12 | 0.0227, 0.1899, 0.1250, 0.0490 | 0.4960 0.5640; 0.0000 0.0084 −4.7638 5.9219; 1.5891 40.6918 | 30 33 33 |
| AR20 | 0.0597, 0.3566, 0.2530, 0.0389 | 0.4960 0.5640; 0.0000 0.0084 −4.7638 5.9219; 1.5891 40.6918 | 30 33 33 |
| TD07 | 0.0330, 0.2791, 0.1923, 0.1672 | 0.4875 0.5647; 0.000 0.0082; −5.0714 5.9913; 1.3845 42.1141 | 26 25 29 |
| AR02 | 0.0878, 1.0269, 0.6729, 0.1512 | 0.4918 0.5887; 0.000 0.0133; −4.5870 5.9431; 1.4500 37.1913 | 29 29 0 |
| AR07 | 0.0326, 0.2483, 0.1579, 0.1622 | 0.4875 0.5647; 0.000 0.0082; −5.0714 5.9913; 1.3845 42.1141 | 26 25 29 |
| AR15 | 0.0305, 0.2402, 0.1509, 0.1306 | 0.4897 0.5865; 0.0000 0.0162 −5.7218 5.9192; 1.4135 37.1985 | 28 29 31 |
| AR22 | 0.0622, 0.6502, 0.4481, 0.1422 | 0.4944 0.5818; 0.0000 0.0151 −4.4427 5.4823; 1.5967 34.3096 | 30 31 31 |
| AR03 (2V) | 0.0375, 0.4480, 0.2854, 0.1021 | 0.4927 0.5816; 0.000 0.0142; −6.0128 8.0853; 1.3809 68.2065 | 29 31 32 |
| AR08 (2V) | 0.0310, 0.2408, 0.1518, 0.1197 | 0.4966 0.5772; 0.0000 0.0092 −5.2981 5.5263; 1.5935 31.7060 | 30 30 0 |
| AR04 | 0.0322, 0.2826, 0.1842, 0.1244 | 0.4944 0.5818; 0.000 0.0151 −5.8163 6.0338; 1.5967 38.4325 | 29 31 31 |
| AR05 | 0.0717, 0.6632, 0.4226, 0.1729 | 0.4951 0.6126, 0.000 0.0182; −5.1327 7.4416, 1.4944 62.6376 | 33 32 30 |
| AR06 | 0.0241 0.1503 0.0884 0.0573 | 0.4935 0.5884, 0.00 0.0127; −5.6375 5.9706; 1.0000 37.4963 | 31 31 33 |
| AR09 | 0.0238 0.1622 0.1001 0.1028 | 0.4914 0.5746; 0.00 0.0129; −4.8887 5.8321; 1.3109 35.0186 | 31 31 31 |
| AR13 | 0.0267 0.2162 0.1395 0.1237 | 0.4930 0.5808; 0.00 0.0114; −5.5550 7.9772; 1.5066 67.8095 | 33 31 31 |
| AR14 | 0.0218 0.2004 0.1266 0.1283 | 0.4887 0.5678; 0.00 0.0127; −5.4733 5.6923; 1.4947 40.4251 | 33 29 32 |
| AR16 | 0.0191 0.1817 0.1185 0.1111 | 0.4936 0.5793; 0.00 0.0107; −5.3564 6.4949; 1.4653 43.8045 | 30 33 30 |
| AR17 | 0.0196 0.1969 0.1325 0.0531 | 0.4961 0.5874; 0.00 0.0112; −6.8307 7.1600; 1.5137 54.6354 | 31 33 35 |
| AR18 | 0.0257 0.2216 0.1396 0.1258 | 0.4945 0.5593; 0.00 0.0072; −4.9323 6.1556; 1.5738 39.2848 | 30 30 31 |
| AR19 | 0.0297 0.4415 0.2795 0.0777 | 0.4964 0.5814; 0.00 0.0141 −5.6104 6.8170; 1.3318 51.2641 | 31 31 31 |
| AR21 | 0.0333 0.2957 0.1761 0.0711 | 0.4960 0.5640; 0.00 0.0084; −4.7638 5.9219; 1.5891 40.6918 | 30 33 33 |

TABLE 3-continued

Estimated parameter ranges

| Physical Growth Ranking | ΔPhysical growth, Δweight, Δbody-length, Δhead circumf, ΔAIMS | Ranges Estimated μ, σ², sk, kt from Norm MaxAcc | Mean Temperature/visit |
|---|---|---|---|
| A25 | 0.0249 0.2426 0.1545 0.0899 | 0.4896 0.6193; 0.00 0.0204; −5.2763 5.46781.5287 32.1816 | 26 30 24 |

Figure 14C:
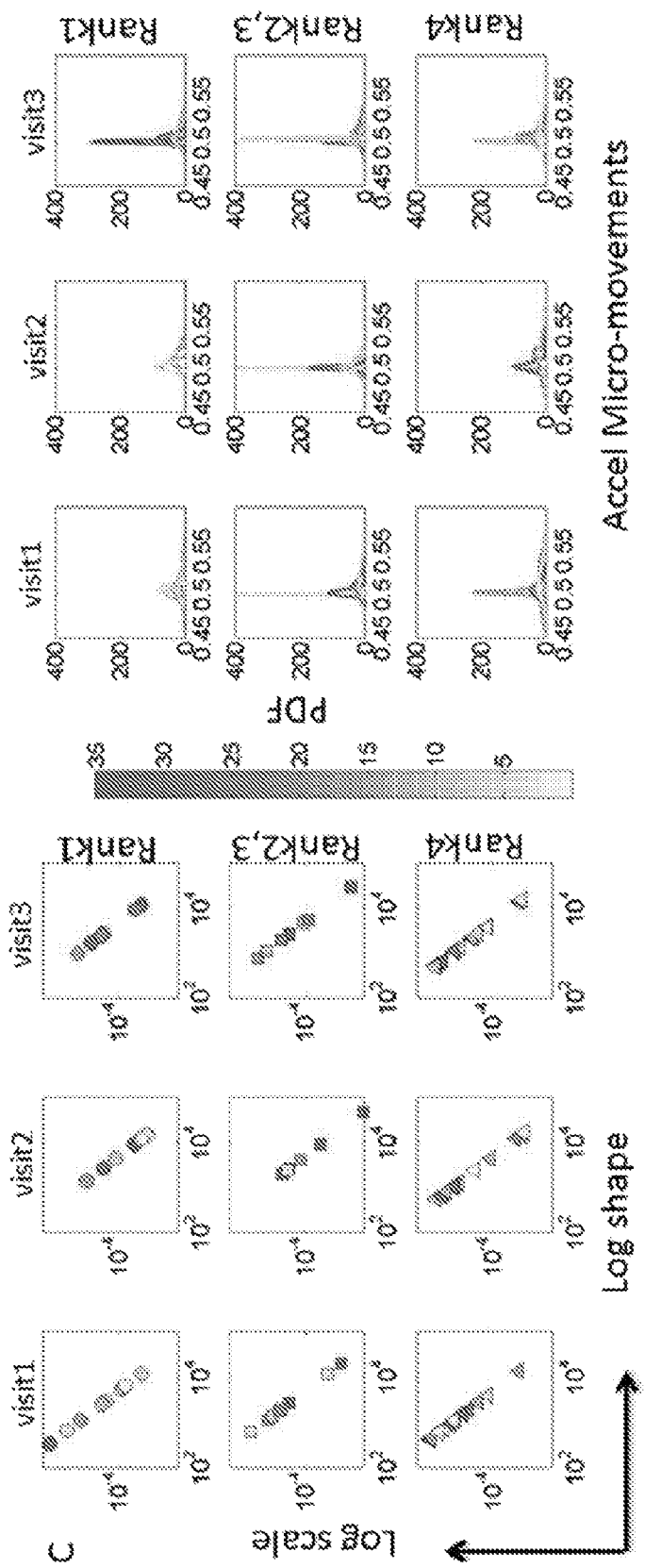

To help visualize the scatter data, a surface was fit across all points in the scatter and colored according to the height of the rate of change of the AIMS total score. This is shown in FIG. 14B with the line connecting the babies in Group 1 traced from left to right in the order of the rate of change of the AIMS total score. In this panel babies with the higher rate of growth in head circumference (represented by the size of the marker) lead the group. The two babies at the tail of this path are the two CAR babies that made the ranked median cutoff above the rest and into the Rank1-TD group. These two babies (twins) started out lagging behind following premature birth. However, they caught up and this could be appreciated at the rate of change level. In contrast, when examining instead the absolute value of the parameters they seemed similar to the other CAR babies. These results prompted an assessment of the fluctuations in motor performance and the noise-to-signal transitions underlying these rates of physical growth. FIG. 14C shows the results from these analyses as the signatures of neuromotor control were estimated by integrating output in motor and temperature fluctuations. The right panel of FIG. 14C shows the estimated Gamma parameters on the log-log Gamma plane. Each dot represents the median values of each baby across a large number of estimated parameters from 8 hours of continuous recordings.

Similar to FIGS. 8A-8C and 10A-10D, the median temperature associated to each set of motor fluctuations are identified by the heat map. Babies in the Rank 1 group raise the temperature values as time progresses indicating higher levels of actively self-generated motions (draining more battery energy than passive motions and therefore heating more the sensor). These active motions shifted signatures down and to the right on the Gamma parameter plane. From visit to visit these shifts in temperature values and Gamma parameter values were more pronounced in the Rank 1 than in the Rank 4 groups. Indeed, in the Rank 1 group, from visit 1 to visit 3, the drop in noise from higher to lower and the change in shape from skewed to symmetric was significant (ranksum Wilcoxon test p<0.01) but not so in Rank 4 babies (p<0.9). Right panel of the figure shows the estimated PDFs corresponding to the Gamma parameters in the right panel.

These signatures were next assessed as rates of change (dividing them by the number of days since birth) in order to uncover the frequency of noise-to-signal transitions that each baby underwent each visit, as well as those corresponding to the average transitions across visits for each statistically ranked Group.

High Inner-Quadrant and Inter-Quadrant Frequency of Noise to Signal Transitions Mark Typical Neurodevelopment For each of the individual members of each ranked group, the minute fluctuations in motor performance were examined using the methods described with respect to FIGS. 11A-11C and the stochastic signatures of these fluctuations were characterized as they transitioned from the LUQ to the RLQ of the Gamma parameter plane, i.e. the probability distribution functions transitioning to low noise-to-signal ratio and distribution shapes shifting towards symmetric distributions.

The signatures of fluctuations in motor performance of the babies in Rank 1 group transitioned far more frequently from higher to lower noise and from highly skewed to more symmetrically shaped PDFs than those of babies in the other groups. This is depicted in FIG. 15A for the stationary case where the transitions are either within the LUQ or within the RLQ. The children were ranked according to the proportion of times their signatures remained steady-state within one quadrant or the other. The insets of the FIG. 15A show the three groups from the median ranked parameters of physical growth in FIG. 15A. Specifically, babies in the first group, denoted typically developing (TD), have the highest proportion of remaining steady in the LUQ or the RLQ on average. The PAR group falls intermediate to TD and HR. The HR group has the lowest proportion of steady-state in LUQ or RLQ. FIG. ISA shows stationary (inner-quadrant) transitions sorted according to the proportion of times fluctuating within each quadrant before crossing to the other quadrant. Each dot represents a baby (up-triangles are TD, circles are PAR and down-triangles are HR). Inset is the median across each group. FIG. 15B shows non-stationary (inter-quadrants) transitions sorted according to the proportion of times crossing across quadrants from the RLQ to the LUQ. The same index used to plot the opposite direction of transitions shows higher variability when crossing from the LUQ the RLQ. The inset shows the median values per group. FIG. 15C shows median values of noise-to-signal transitions per group during the first visit already distinguish the groups in both the stationary and the non-stationary cases.

The non-stationary noise-to-signal inter-quadrant transitions shown in FIG. 15C right panel were characterized by multiple shifts between the LUQ and RLQ. Their proportions also showed—for each individual baby—patterns that distinguish the TD from the PAR and FIR babies. Here, the transitions to the RLQ were ranked by proportion (individualized rates for each baby obtained from the overall total frequency of transitions of each baby). They systematically decreased according to the group type. In contrast those of the LUQ were highly variable across the three groups. The inset shows the differences in average proportion taken across all members of each group. Here, the frequency in dynamically transitioning across the quadrants clearly separates those TD babies from the PAR and the HR babies.

FIG. 15C shows the median values of the stationary and non-stationary transitions for the first visit. This result shows that differences in neurodevelopmental trajectories associated with the rates of change of physical growth can be detected within the first months of infancy.

Steady Rate of Growth in Physical Changes Corresponding to Steady Rate of Change in Transitions from Noise-to-Signal Mark Typical Neurodevelopment In addition to the frequency in noise-to-signal transitions, the magnitude of the maximal shift between the LUQ and the RLQ was significantly higher in CT babies (p<0.01 ranksum Wilcoxon test). To further quantify this, a relationship between the maximal noise-to-signal transitions/day and the change in physical-growth parameter/day was assessed across the above mentioned three groups. The scalar denoting the average across the visits for each of the neuro-motor control and physical growth domains was plotted for each baby on a parameter plane and a line through the scatter corresponding to each group was fit.

FIGS. 16A-16C show the results of this fitting for each of three groups (TD, PAR and HR). The TD (Group Rank 1) showed for each parameter a linear relation with positive slope ($R^2$ 0.89, 0.89, 0.83) for body-length (FIG. 16A), weight (FIG. 16B), and head circumference (FIG. 16C), respectively. This group was followed by a weaker relation ($R^2$ 0.52, 0.40, 0.10) in the PAR group 2. The babies in the HR group 3, the one ranked with the slowest rates of change in growth, had a flat slope ($R^2$ 0.19, 0.16, 0.06) indicating stagnation in the rate of change of noise-to-signal transitions towards motions under volitional control. These HR babies, classified as such with respect to the rate of change of physical growth, are also at risk of neurodevelopmental derail because noise-to-signal transitions were absent or did not evolve within each of the three visits. When examined longitudinally, their rates of change were stagnated in both frequency and amplitude. They did not evolve these metrics of neuro-motor control from visit to visit.

The normalized waveform of the time series of fluctuations in maximal deviations above the empirically estimated mean acceleration within each temperature regime was used. In doing so, it was possible to capture the individual rates at which these signatures transitioned from spontaneous random noise in the LUQ to well-structured, systematic noise, in the RLQ of the Gamma parameter plane, as determined by the median of the estimated Gamma parameters each day. Specifically, the magnitude and the frequency of the shifts were tracked. In this sense, for each visit, it was shown that there was convergence towards a consistently reliable statistical signal, one with predictive power.

It is noted that when allowing the non-normal and non-linear nature of the data reflecting the rates of change of physical growth and those in neuromotor control, a linear relationship characterizing these parameters in the TD group was identified. This group showed a positive slope and an adjusted $R^2$ closer to 1 than the HR group. The latter showed instead a flat slope denoting stagnation in the rates of change of neuromotor control with an $R^2$ closer to 0. The PAR group fell in between these two, showing a systematic self-emerging relation across all babies.

In the HR group with stagnant neuromotor control, it can be seen that as the baby's body physically grew, the brain control over self-generated bodily motions lacked the signatures of voluntary control: The shift into high signal content and statistical regularities conducive of predictable and controllable codes was absent from the fluctuations in motor performance of these HR babies. This absence was detected as early as the first visit in the study and persisted 4 months later.

Movement as a Form of Reafferent Sensory Input

Physical movement measurements from the body are rarely considered in developmental pediatrics. When they are considered in developmental research, the analyses of kinematics parameters are generally subject to a "one-size-fits-all" approach, whereby the assumptions of normality and linearity are imposed to the data. Often an averaged kinematic parameter is assumed from a handful of trials with assumed (additive) variability symmetrically defined around the (theoretically) assumed mean. The methodology presented herein can be used to continuously estimate the shifts in the inherent variability of the movements of the infant, not just as motor output variability, but also variability as a form of sensory input that re-enters the nervous system that produced those motions in the first place.

In this sense, the principle of reafference between the central nervous system and the peripheral organs proposed by von Holst and Mittlestaedt in 1950 states that "Voluntary movements show themselves to be dependent on the returning stream of afference which they themselves cause". The longitudinal assessment of these newborn infants showed the individual evolution of the noise-to-signal transitions in their bodily rhythms, denoting as well the shifts from spontaneous random variations to well organized variations. The latter is suggestive of the gradual acquisition of voluntary control in some infants but also of their lacking in other infants that showed stagnation in this evolution.

The presented methods recognize that fluctuations in motor performance flow as output from the brain to the peripheral limbs, but also suggest them as a source of kinesthetic reafference flowing from the peripheral limbs back to the brain as an important source of sensory feedback.

Disruption in the evolution and maturation of motor output as a form of kinesthetic reafference in the newborn should raise a flag for risk of neurodevelopmental derail. This in turn can alert practitioners of potentially negative future consequences impeding the emergence of intentional cognition. Here, this lack of neurodevelopmental maturation is characterized in terms of noise-to-signal transitions and this characterization can be used as criteria to flag a clear element of risk in early neurodevelopment.

Proposed Outcome Measure of Neurodevelopment at Risk: Misalignment of Physical and Mental Growth The illustrated index can be used as an objective biomarker to track neurodevelopment and be used at the earliest stages of development of the newborn infant to flag risk and rapidly target intervention as well as measure outcomes of the intervention.

When physical growth is not examined in isolation but rather viewed in tandem with the development of neuromotor control, one can easily and rapidly detect a lack of progress. Indeed, results illustrate that during typical development both processes are interwoven in the early days, undergoing an accelerated rate of change together. At the individual level, the data shows that it was possible to continuously track these rates each visit and uncover a longitudinal pattern. At the cohort level, a general rule was able to be established.

Objective and Personalized Biometrics for Precision Medicine in Pediatrics

The personalized statistical platform presented here along with the proposed taxonomy of control levels in FIG. 9 to longitudinally track inter-relations across these levels provide an objective outcome measure of neurodevelopment in newborn infants. The precision of these new biometrics needs to be validated in a larger number of infants with data from higher frequency of visits.

The waveforms output by temperature and motion sensors were used because they were accessible in non-intrusive ways. However, other sensors and combinations could be used to capture other rhythms of the newborn's nervous systems. For example, the same statistical platform that was described in the examples could have been applied to time series of waveforms from respiratory or feeding (sucking) rhythms easy to harness in the NICU or in typically newborn infant wards. Feeding and non-feeding sucking patterns require precise motor control from orofacial structures. As such they are a precursor of voluntary control that the nervous systems of the newborn may come to self-discover and transfer to the control of bodily rhythms at large.

Figures 23A, 23B:
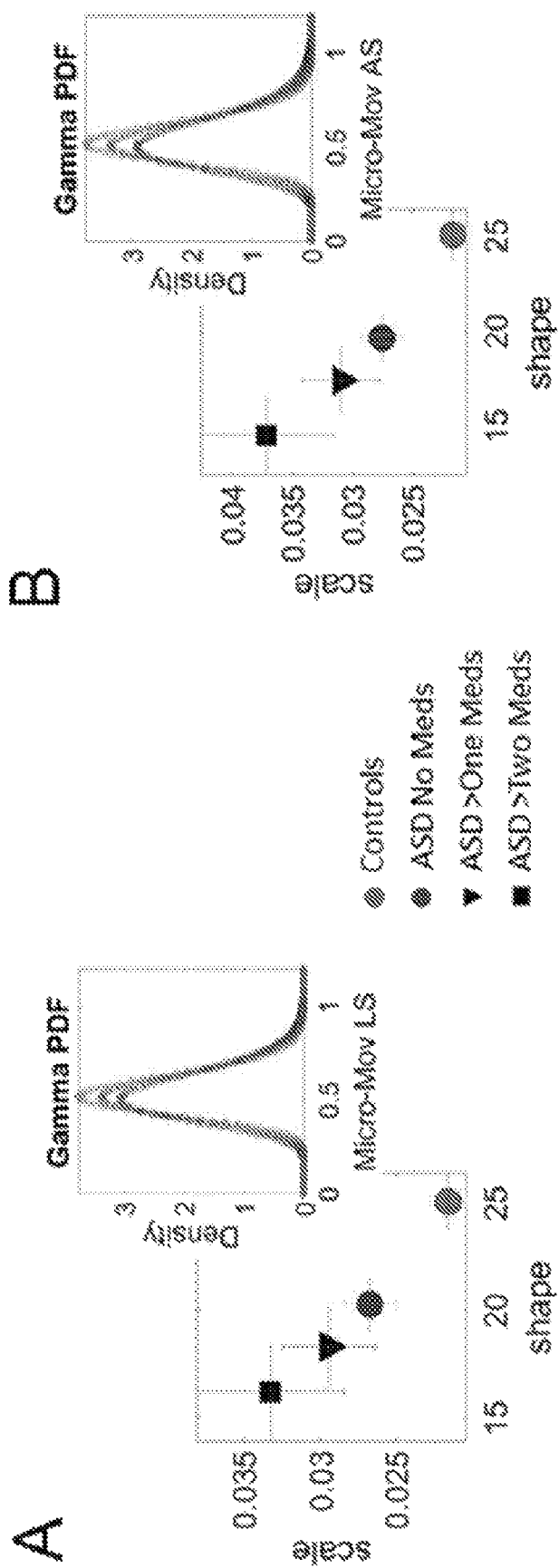
FIG. 23A and FIG. 23B illustrate examples of the effects of stochastic signatures of motions due to medication intake.

There can be variations in the above illustrated embodiments as appreciated by one ordinarily skilled in the art. For example, the tracking of neuro-development disorders may not be limited to infants, but can also be applied to adults. Further, the above illustrated embodiments may be applied to assess the medication intake or age effect of the subject. For example, FIGS. 23A-23B capture the amount of involuntary motions polluting the person's nervous systems and impeding the volitional control of the brain over the body. In particular, FIG. 23A shows estimated Gamma shape and scale parameters with corresponding PDFs for the linear speed peaks in groups of TDs, medication naïve ASD participants and participants with ASD taking two or more medications. FIG. 23B shows similar trends for the angular speed peaks. As shown, medication intake alters the stochastic signatures of involuntary head motions in negative ways, as reflected in a systematic increase of dispersion and skewness with psychotropic medication intake.

In some scenarios, the above illustrated system may further be configured to, after using the fitted curve to identify whether the subject has a normal neuro-development or has a risk of neuro-development disorder, re-track neuro-development disorder in the subject, after a therapy intervention is completed. In re-tracking the neuro-development disorder in the subject, the system may receive a second rhythm produced by the nervous system of the subject at each of a plurality of time periods after the therapy intervention, the second rhythm comprising one or more waveforms produced by the one or more wearable sensors, the second rhythm is associated with the time period. The system may also receive one or more physical characteristics values of the subject, the one or more physical characteristics values are each associated with the time period after the therapy intervention, on which measurements of the one or more physical characteristics values were taken.

The system may further be configured to: estimate trajectories of fluctuations of the second rhythm over the plurality of time periods for the second rhythm; generate a digital representation that represents the estimated trajectories against a change in one of the physical characteristics values between each two successive time periods over the plurality of time periods for the second rhythm; perform a fitting for the digital representation to determine a fitted curve; use the fitted curve to identify whether the subject has a normal neuro-development or has a risk of neuro-development disorder; compare an outcome of tracking the neuro-development disorder before and after the therapy intervention is complete to generate a comparison result; and output the comparison result. In outputting the comparison result, the system may display plots of the statistical signatures before and after the intervention on the display. Alternatively, and/or additionally, the system may save the comparison result in a memory that can be accessed by one or more users. Alternatively, and/or additionally, the system may also print out the comparison result on a physical document for a user to review.

In some scenarios, the system may also be configured to, after using the fitted curve to identify whether the subject has a normal neuro-development or has a risk of neuro-development disorder, re-track neuro-development disorder in the subject, after a medication intake. The system may receive a second rhythm produced by the nervous system of the subject at each of a plurality of time periods after the medication intake, the second rhythm comprising one or more waveforms produced by the one or more wearable sensors, the second rhythm is associated with the time period. The system may receive one or more physical characteristics values of the subject, the one or more physical characteristics values are each associated with the time period after the medication intake, on which measurements of the one or more physical characteristics values were taken.

The system may further be configured to: estimate trajectories of fluctuations of the second rhythm over the plurality of time periods for the second rhythm; generate a digital representation that represents the estimated trajectories against a change in one of the physical characteristics values between each two successive time periods over the plurality of time periods for the second rhythm; perform a fitting for the digital representation to determine a fitted curve; use the fitted curve to identify whether the subject has a normal neuro-development or has a risk of neuro-development disorder; compare an outcome of tracking the neuro-development disorder before and after the medication intake; and output the comparison.

Figure 26:
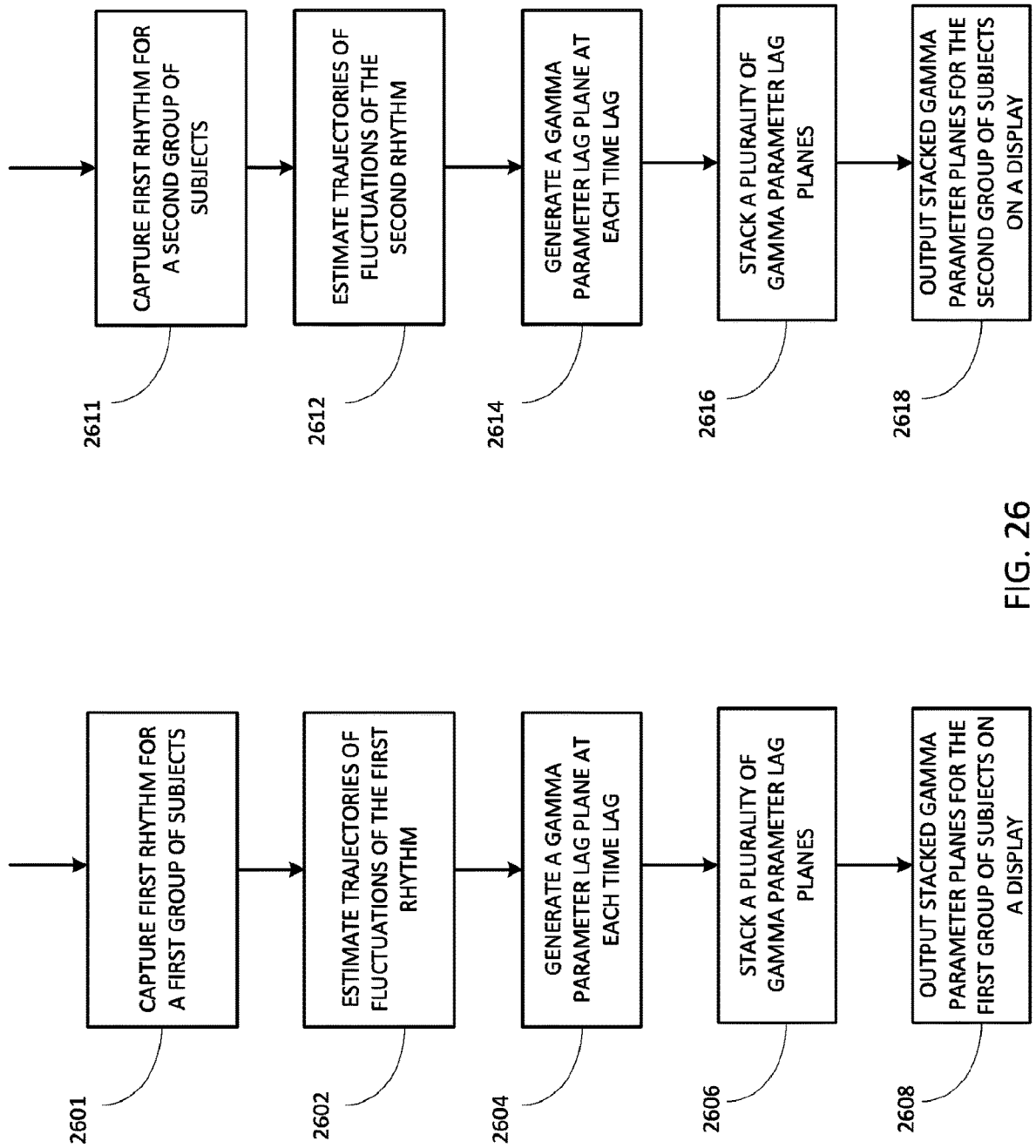
FIG. 26 illustrates an example of a process for tracking medication/age effect.

In some embodiments, a process that can be implemented in the above described system for tracking neuro-development disorder may be used for a first group of subjects belonging to an age group. The system may include a processor, a display, and one or more wearable sensors attached to each of the first group of subjects. As shown in FIG. 26, a process for tracking the effect of medication intake may include using the wearable sensors to capture, at each of a plurality of time periods, a rhythm produced by a nervous system of each of the first group of subjects 2601. The rhythm may include one or more waveforms produced by the one or more wearable sensors, where each rhythm is associated with the time period. The process may include: estimating trajectories of fluctuations of the rhythm over the plurality of time periods 2602; generating a Gamma parameter lag plane at each of the plurality of time periods 2604; stacking a plurality of Gamma parameter lag planes 2606, each plane corresponding to a time period in sequence over the plurality of time periods; and outputting the stacked Gamma parameter lag planes on the display 2608.

Each of the stacked Gamma parameter lag planes may include a shape and a scale parameter of a continuous Gamma distribution family for the waveforms of the rhythm associated with each time period for at least one of the one or more wearable sensors attached to at least one of the first group of subjects. Each Gamma parameter lag plane may also include an intersecting point at which a median scale line and a median shape line intersects. In outputting the stacked Gamma parameter lag planes on the display, the process may display a trajectory of the intersection point at each Gamma parameter lag plane over the plurality of time periods.

In tracking the medication and age effect, the process may use one or more additional wearable sensors attached to each of a second group of subjects belonging to the age group. Each of the first and second group of subjects may have a medication status, such as ASD no medication, controls, antidepressants, atyp-ADHD, stimulants, atyp-antipsych etc. The medication status of the first and second group of subjects are different, which allows the system to track the effect of medication intake.

With further reference to FIG. 26, the process may include using the additional wearable sensors to capture, at each of the plurality of time periods, a second rhythm produced by a nervous system of each of the second group of subjects 2611. The second rhythm may include one or more waveforms produced by the one or more additional wearable sensors, and the second rhythm is associated with the time period. The process may also include: estimating trajectories of fluctuations of the second rhythm over the plurality of time periods 2612; generating a Gamma parameter lag plane at each of the plurality of time periods for the second rhythm 2614; stacking a plurality of Gamma parameter lag planes for the second rhythm 2616, where each plane corresponds to a time period in sequence over the plurality of time periods; and outputting the stacked Gamma parameter lag planes for the second rhythm on the display 2618. Accordingly, the system may track the stochastic signatures before and after medication intake for different age groups.

Figure 24:
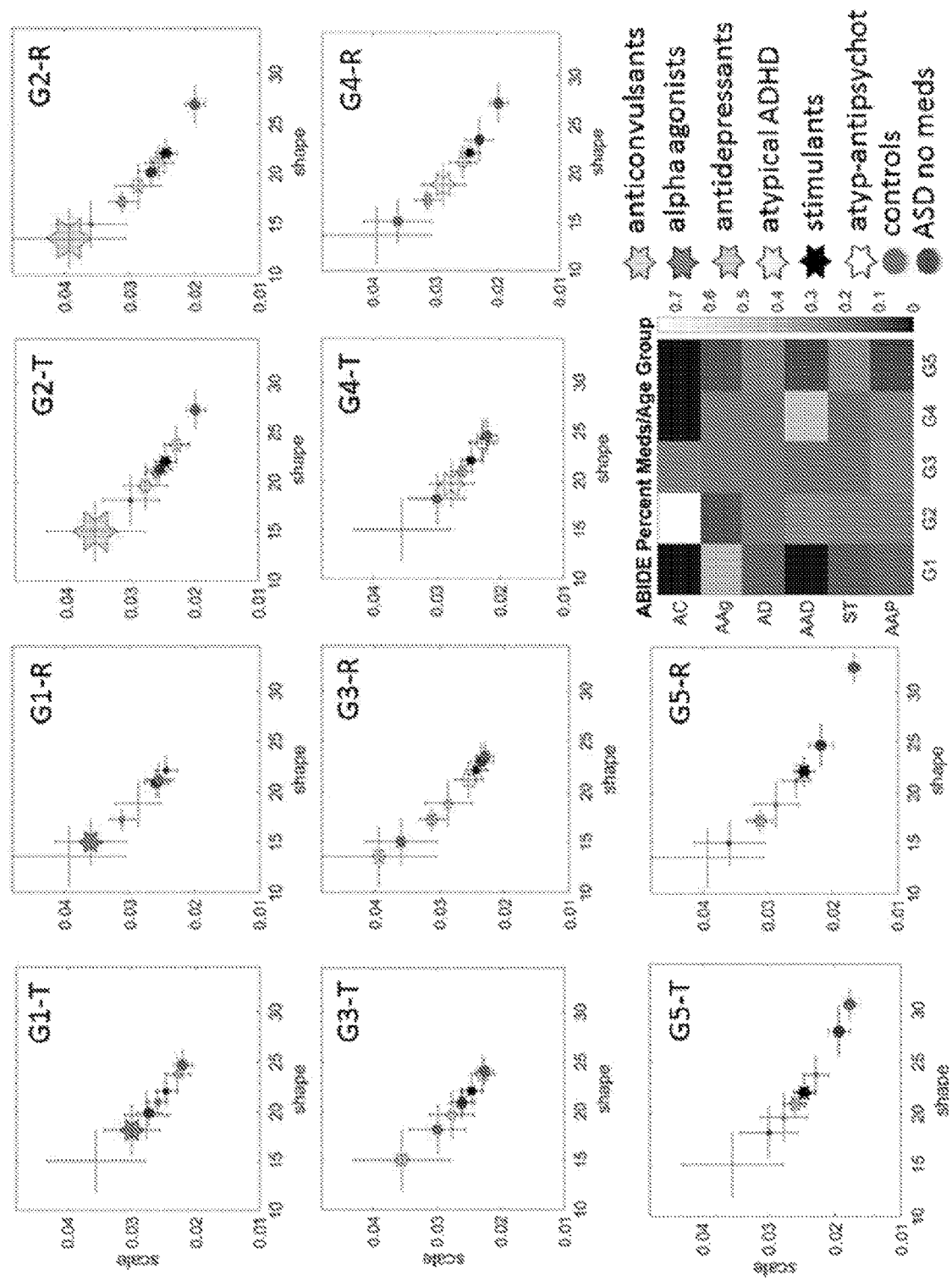
FIG. 24 illustrates an example of speed-dependent stochastic signatures of movements as a function of medication status and age.

In a non-limiting example, FIG. 24 shows speed-dependent stochastic signatures of head micro-movements as a function of medication status and age, for medication classes when taken as part of a combination-treatment. Each age group number and letter (e.g. G1-T and G1-R) corresponds to the linear/translational (T) and angular/rotational (R) speed-dependent signatures across medication classes shown with 95% Confidence Intervals (CIs). Groups by age are G1 (6-10.99), G2 (11-12.99), G3 (13-14.99), G3 (15-16.99), G5 (above 17) years old. The empirically estimated Gamma parameters are obtained from the pooled group data comprising ASD individuals 'on' medication and each point is cast against the members of age-matched reference groups (medication naïve ASD: blue and CT: red). Note that controls have the lowest NSR and the highest shape (most symmetric) value across all age groups. The size of the marker on the Gamma parameter plane represents the percentage of that medication type within the group based on the reported information in the ABIDE. The color-coded matrix presents these proportions for each age group (columns) and medication class (rows). The most commonly prescribed medication class for each age group is as follows: G1: alpha agonist, G2: anticonvulsant, G3: anticonvulsant, G4: atypical ADHD and G5: stimulant. No marker means that the medication intake is not reported in the group (darkest blue entry in the matrix).

Figure 25:
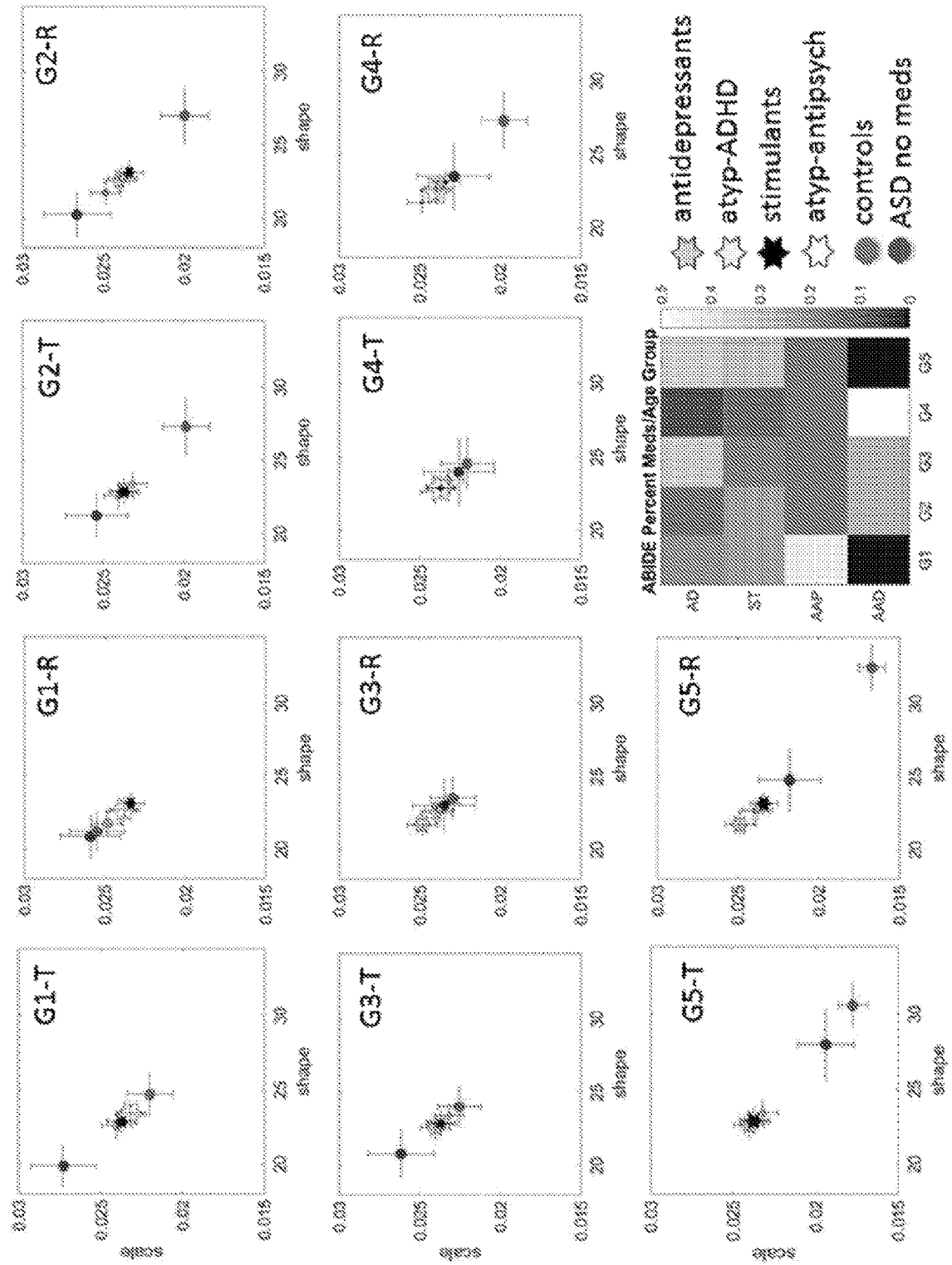
FIG. 25 illustrates an example of speed-dependent stochastic signatures of movements as a function of medication status and age.

FIG. 25 shows speed-dependent stochastic signatures of head micro-motions variability for medication classes when taken in isolation. The highest percentages across age groups are: G1 atypical antipsychotic, G2 atypical ADHD, G3 antidepressant, G4 atypical ADHD, G5 antidepressant. Notice that when taken in isolation, the same medication class has a different effect for each age group than when taken as part of a medication combination.

Figure 4:
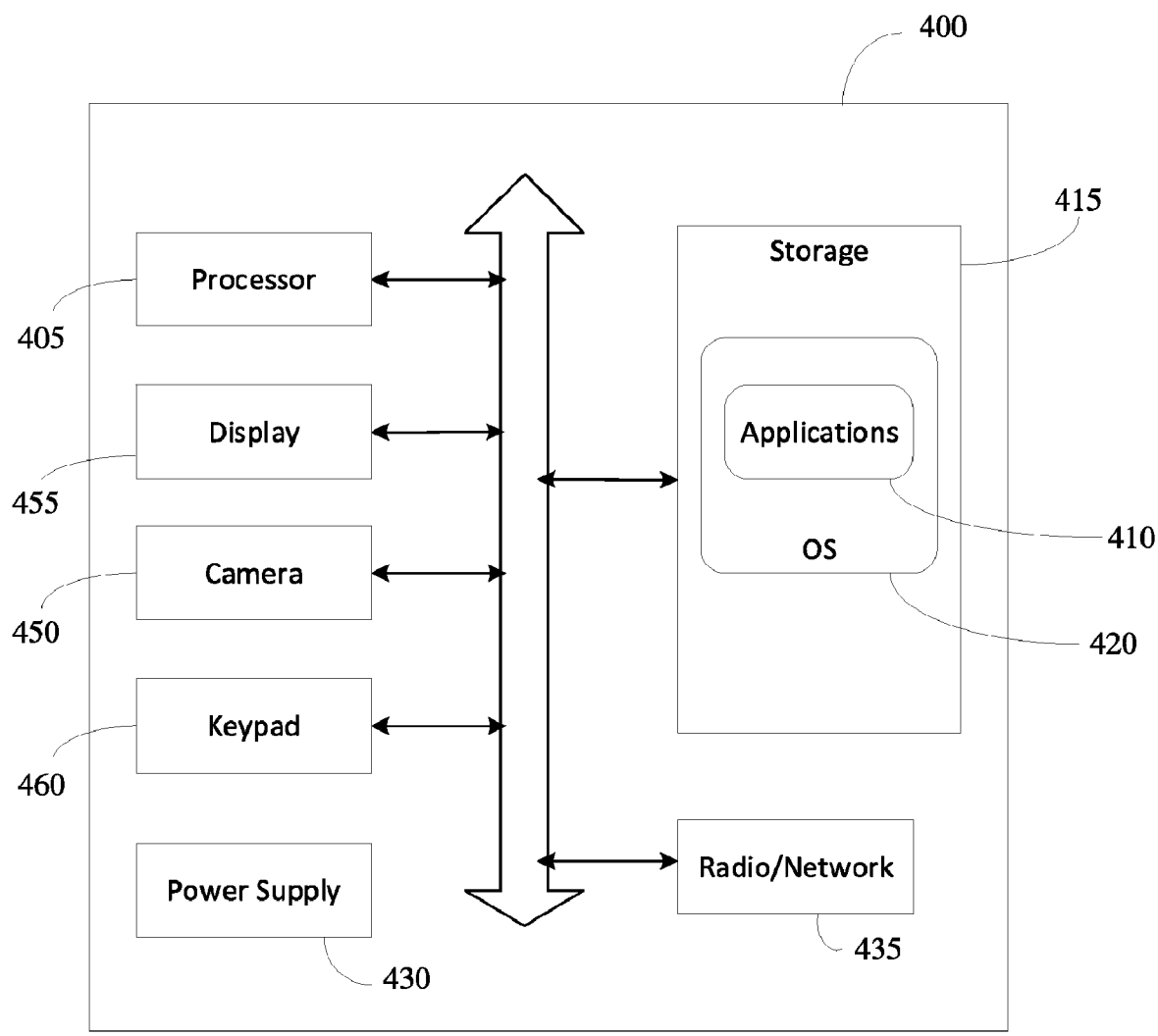
FIG. 4 shows a block diagram illustrating components of a computing device used in some embodiments.

FIG. 4 shows a block diagram illustrating components of a computing device used in some or all of the above illustrated embodiments. For example, computing device 400 can be used in implementing a desktop or notebook computer or a tablet or smartphone. In some cases, computing device 400 can be a wearable device.

Computing device 400 includes at least one hardware processor 405 that processes data according to instructions of one or more application programs 410 stored on a storage system 415. The one or more application programs 410 can include a web browser application 412 and/or tracking application 414. The one or more application programs 410 may be loaded into a part of the storage system 415 and run on or in association with the operating system 420. Other applications may be loaded into storage system 415 and run on the device, including various client and server applications.

Storage system 415 can include any computer readable storage media readable by the at least one hardware processor 405 and capable of storing software including the one or more application programs 410 and operating system 420. Storage system 415 may include volatile and nonvolatile, removable and non-removable media implemented in any method or technology for storage of information. Examples of storage media include random access memory, read-only memory, magnetic disks, optical disks, CDs, DVDs, flash memory, magnetic cassettes, magnetic tape, magnetic disk storage or other magnetic storage devices, or any other suitable storage media. In some cases, storage system 415 can include virtual memory hosted on a hardware system.

Computing device 400 can include a power supply 430, which may be implemented as one or more batteries and/or an energy harvester (ambient-radiation, photovoltaic, piezoelectric, thermoelectric, electrostatic, and the like). Power supply 430 might further include an external power source, such as an AC adapter or a powered docking cradle that supplements or recharges the batteries.

Computing device 400 may also include a radio/network interface 435 that performs the function of transmitting and receiving radio frequency communications. The radio/network interface 435 facilitates wireless connectivity between computing device 400 and the "outside world," via a communications carrier or service provider. Transmissions to and from the radio/network interface 435 are conducted under control of the operating system 420, which disseminates communications received by the radio/network interface 435 to application programs 410 and vice versa.

Figure 5:
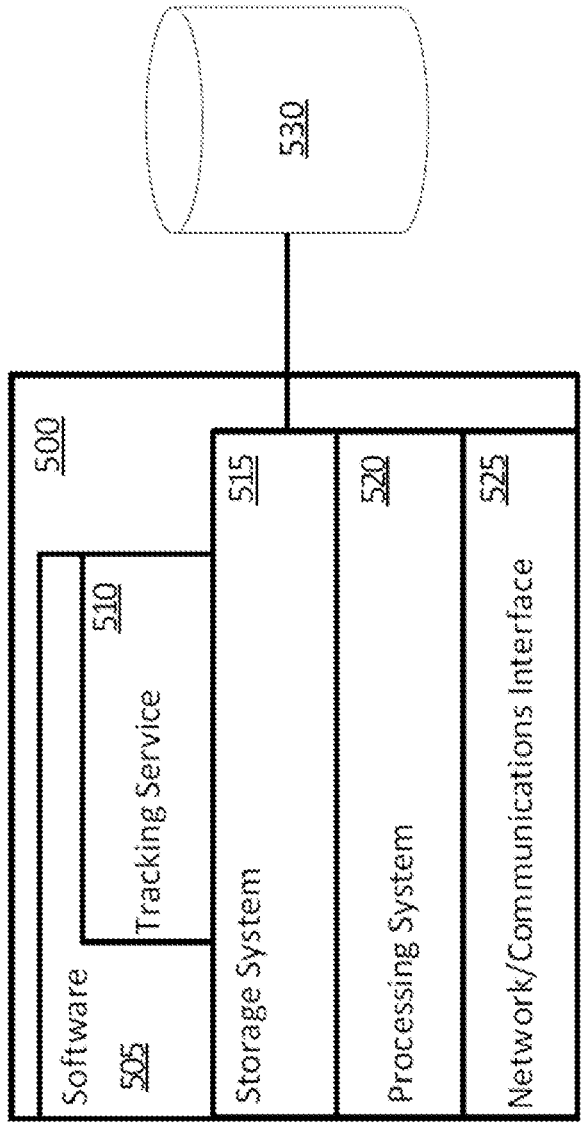
FIG. 5 illustrates a block diagram of a computing system that may perform various processes described in this disclosure.

The radio/network interface 435 allows computing device 400 to communicate over a network with other computing devices including computing systems such as described with respect to FIG. 1 and FIG. 5 that execute the described services.

An audio interface 440 can be used to provide audible signals to and receive audible signals from the user. For example, the audio interface 440 can be coupled to a speaker to provide audible output and a microphone to receive audible input, such as to facilitate verbal commands or even a telephone conversation. Computing device 400 may further include video interface 445 that enables an operation of an optional camera (450) to record still images, video stream, and the like. Visual output can be provided via a display 455. In some cases, the display may be a touch screen. In some cases, additional user input elements, such as buttons, keys, roller wheel, and the like, are used to select items displayed as part of a graphical user interface on the display 455. A keypad 460 can also be included for user input. The keypad 460 may be a physical keypad or a soft keypad generated on the touch screen display 455.

It should be understood that any computing device implementing computing device 400 may have more or fewer features or functionality and is not limited to the configurations described herein.

FIG. 5 illustrates a block diagram of a computing system that may implement the service platform described herein. Referring to FIG. 5, system 500 may be implemented within a single computing device or distributed across multiple computing devices or sub-systems that cooperate in executing program instructions. The system 500 can include one or more blade server devices, standalone server devices, personal computers, routers, hubs, switches, bridges, firewall devices, intrusion detection devices, mainframe computers, network-attached storage devices, and other types of computing devices. The system hardware can be configured according to any suitable computer architectures such as a Symmetric Multi-Processing (SMP) architecture or a Non-Uniform Memory Access (NUMA) architecture.

The system 500 can include a processing system 520, which may include one or more hardware processors and/or other circuitry that retrieves and executes software 505 from storage system 515. Processing system 520 may be implemented within a single processing device but may also be distributed across multiple processing devices or sub-systems that cooperate in executing program instructions.

Examples of processing system 520 include general purpose central processing units, application specific processors, and logic devices, as well as any other type of processing device, combinations, or variations thereof. The one or more processing devices may include multiprocessors or multi-core processors and may operate according to one or more suitable instruction sets including, but not limited to, a Reduced Instruction Set Computing (RISC) instruction set, a Complex Instruction Set Computing (CISC) instruction set, or a combination thereof. In certain embodiments, one or more digital signal processors (DSPs) may be included as part of the computer hardware of the system in place of or in addition to a general purpose CPU.

Storage system(s) 515 can include any computer readable storage media readable by processing system 520 and capable of storing software 505. Storage system 515 may include volatile and nonvolatile, removable and non-removable media implemented in any method or technology for storage of information. Examples of storage media include random access memory, read-only memory, magnetic disks, optical disks, CDs, DVDs, flash memory, magnetic cassettes, magnetic tape, magnetic disk storage or other magnetic storage devices, or any other suitable storage media. In some cases, storage system 515 can include virtual memory hosted on a hardware system. In no case is the storage medium of storage system 515 a propagated signal or carrier wave.

Storage, system 515 may be implemented as a single storage device but may also be implemented across multiple storage devices or sub-systems co-located or distributed relative to each other. Storage system 515 may include additional elements, such as a controller, capable of communicating with processing system 520.

The described services, including process 200, can be carried out by instructions stored on storage system 515, for example as service 510. Data collected by the service can be stored at storage system 515 or as part of a separate system with which system 500 communicates, such as a remote storage provider. For example, data, such as user input, sensor data, and various outcomes of analysis (including intermediary values when desired) may be stored on any number of remote storage platforms that may be accessed by the system 500 over communication networks via the communications interface 525. Such remote storage providers might include, for example, a server computer in a distributed computing network, such as the Internet. They may also include "cloud storage providers" whose data and functionality are accessible to applications through OS functions or APIs.

Software 505 may be implemented in program instructions and among other functions may, when executed by system 500 in general or processing system 520 in particular, direct the system 500 or processing system 520 to operate as described herein for tracking neurodevelopment and identifying a risk of neurodevelopment disorder and/or a typical development (as service 510).

Software 505 may also include additional processes, programs, or components, such as operating system software or other application software. It should be noted that the operating system may be implemented both natively on the computing device and on software virtualization layers running atop the native device operating system (OS). Virtualized OS layers, while not depicted in FIG. 5, can be thought of as additional, nested groupings within the operating system space, each containing an OS, application programs, and APIs.

Software 505 may also include firmware or some other form of machine-readable processing instructions executable by processing system 520.

System 500 may represent any computing system on which software 505, including the specialized digital service 510, may be staged and from where software 505 may be distributed, transported, downloaded, or otherwise provided to yet another computing system for deployment and execution, or yet additional distribution.

In embodiments where the system 500 includes multiple computing devices, the server can include one or more communications networks that facilitate communication among the computing devices. For example, the one or more communications networks can include a local or wide area network that facilitates communication among the computing devices. One or more direct communication links can be included between the computing devices. In addition, in some cases, the computing devices can be installed at geographically distributed locations. In other cases, the multiple computing devices can be installed at a single geographic location, such as a server farm or an office.

A communication interface 525 may be, included, providing communication connections and devices that allow for communication between system 500 and other computing systems (not shown) over a communication network or collection of networks (not shown) or the air. Examples of connections and devices that together allow for inter-system communication may include network interface cards, antennas, power amplifiers, RF circuitry, transceivers, and other communication circuitry. The connections and devices may communicate over communication media (such as metal, glass, air, or any other suitable communication media) to exchange communications with other computing systems or networks of systems. Transmissions to and from the communications interface can be controlled by the OS, which informs applications of communications events when necessary.

Alternatively, or in addition, the functionality, methods and processes described herein can be implemented, at least in part, by one or more hardware modules (or logic components). For example, the hardware modules can include, but are not limited to, application-specific integrated circuit (ASIC) chips, field programmable gate arrays (FPGAs), system-on-a-chip (SoC) systems, complex programmable logic devices (CPLDs) and other programmable logic devices now known or later developed. When the hardware modules are activated, the hardware modules perform the functionality, methods and processes included within the hardware modules.

Embodiments may be implemented as a computer process, a computing system, or as an article of manufacture, such as a computer program product or computer-readable storage medium. Certain methods and processes described herein can be embodied as software, code and/or data, which may be stored on one or more storage media. Certain embodiments of the invention contemplate the use of a machine in the form of a computer system within which a set of instructions, when executed, can cause the system to perform any one or more of the methodologies discussed above. Certain computer program products may be one or more computer-readable storage media readable by a computer system and encoding a computer program of instructions for executing a computer process.

By way of example, and not limitation (other than the explicit disclaimer below), computer-readable storage media may include volatile and non-volatile, removable and non-removable media implemented in any method or technology for storage of information such as computer-readable instructions, data structures, program modules or other data. Examples of computer-readable storage media include volatile memory such as random access memories (RAM, DRAM, SRAM); non-volatile memory such as flash memory, various read-only-memories (ROM, PROM, EPROM, EEPROM), phase change memory, magnetic and ferromagnetic/ferroelectric memories (MRAM, FeRAM), and magnetic and optical storage devices (hard drives, magnetic tape, CDs, DVDs). As used herein, in no case does the term "storage media" consist of carrier waves or propagating signals.

The above illustrated embodiments are advantageous over prior art systems in that the system captures and generates digital representation (e.g., a plot) that represents increment data on physical body measures of head circumference, body length and body weight reflecting the rate of change of physical growth. The above systems and methods correct and standardize the rate of change data to provide age- and sex-appropriate bases of comparison. For example, by dividing the size data by the number of days since birth, the system converts absolute size data to increment (velocity) data and capture its rate of change (i.e. to find inflection points indicating the system is poised for rapid change or stunted).

It should be understood that the examples and embodiments described herein are for illustrative purposes only and that various modifications or changes in light thereof will be suggested to persons skilled in the art and are to be included within the purview of this application.

The invention claimed is:

1. A system for tracking neuro-development disorder in a subject, the system comprising:
a processor;
one or more wearable sensors configured to be attached to a subject and to capture, at each of a plurality of time periods:
a rhythm produced by a nervous system of the subject, the rhythm comprising one or more waveforms produced by the one or more wearable sensors, each rhythm is associated with the time period, and
one or more physical characteristics values of the subject, the one or more physical characteristics values are each associated with the time period on which measurements of the one or more physical characteristics values were taken; and
a non-transitory computer readable storage medium containing programming instructions configured to cause the processor to:
estimate trajectories of fluctuations of the rhythm over the plurality of time periods,
generate a digital representation that represents the estimated trajectories against a change in one of the physical characteristics values between each two successive time periods over the plurality of time periods,
perform a fitting for the digital representation to determine a fitted curve, and
use the fitted curve to identify whether the subject has a normal neuro-development or has a risk of neuro-development disorder.

2. The system of claim 1, wherein the programming instructions for estimating the trajectories of fluctuations of the rhythm comprise programming instructions configured to determine segments representing changes in parameters on Gamma parameter planes of two successive time periods over the plurality of time periods.

3. The system of claim 2, wherein the parameters on each Gamma parameter plane comprise a shape and a scale parameter of a continuous Gamma distribution family for the one or more waveforms of the rhythm associated with each time period.

4. The system of claim 3, wherein the programming instructions for estimating the trajectories of fluctuations of the rhythm comprise programming instructions configured to determine maximum shift amplitude for each time period by:
determining a vector based on a first point and a second point on the Gamma parameter plane for the time period, the first point having a minimum scale value and a maximum shape value, and the second point having a minimum shape value and a maximum scale value; and
determining a magnitude of the vector using a norm.

5. The system of claim 2, further comprising additional programming instructions configured to cause the processor to determine that each of the segments:
represents a stationary transition if the changes represented by the segment indicates an inner-quadrant transition; or
represents a non-stationary transition if the changes represented by the segment indicates an inter-quadrant transition.

6. The system of claim 5, further comprising additional programming instructions configured to cause the processor to identify a preliminary risk assessment for the subject by determining that, among the segments representing changes over the plurality of time periods:
a percentage of stationary transitions satisfies a condition with a stationary transition threshold value; and/or
a percentage of non-stationary transitions satisfies a condition with a non-stationary transition threshold value.

7. The system of claim 6, wherein the condition with the stationary transition threshold value is a value indicating the percentage of stationary transitions of less than 50% and the condition with the stationary transition threshold value is a value indicating the percentage of non-stationary transitions of less than 1%.

8. The system of claim 1, wherein the subject is an infant and each of the plurality of time periods is a number of days since birth of the subject.

9. The system of claim 8, wherein the one or more physical characteristics values comprise one or more of the following of the subject:
a head circumference value;
a weight value; or
a body length value for the infant.

10. The system of claim 8, wherein the rhythm comprises one or more biorhythms from a nervous system of the subject comprising: a movement, a heartbeat, a skin conductance, a respiration, a swallowing, or a sucking.

11. The system of claim 1, wherein the digital representation comprises a plot.

12. The system of claim 11, wherein:
the fitting comprises a linear regression;
the fitted curve is a line; and
the programming instructions for identifying whether the subject has a normal neuro-development or has a risk of neuro-development disorder comprises programming instructions configured to:
identify the subject as having the normal neuro-development when a slope of the line is in a range from 0.8 to 1 or 0.5 to 0.8; and
identify the subject as having the risk of neuro-development disorder when the slope of the line is in a range of less than 0.5.

13. The system of claim 1, further comprising a display and additional programming instructions contained in the storage medium configured to cause the processor to determine a longitudinal assessment for the subject over the plurality of time periods by:
generating a Gamma parameter lag plane at each of the plurality of time periods;
stacking a plurality of Gamma parameter lag planes, each plane corresponding to a time period in sequence over the plurality of time periods; and
outputting the stacked Gamma parameter lag planes on the display.

14. The system of claim 13, wherein each Gamma parameter lag plane comprises a shape and a scale parameter of a continuous Gamma distribution family for the one or more waveforms of the rhythm associated with each time period for at least one of the wearable sensors.

15. The system of claim 14, wherein the one or more wearable sensors are configured to be attached to one or more body part of the subject selected from a group consisting of: a head, a core and a limb.

16. The system of claim 14, wherein:
each Gamma parameter lag plane also comprises an intersecting point at which a median scale line and a median shape line intersects; and
the programming instructions for outputting the stacked Gamma parameter lag planes on the display comprise programming instructions to display a trajectory of the intersecting point at each Gamma parameter lag plane over the plurality of time periods.

17. The system of claim 1, wherein the programming instructions are further configured to, after using the fitted curve to identify whether the subject has a normal neuro-development or has a risk of neuro-development disorder, re-track neuro-development disorder in the subject, after a therapy intervention is completed, by:
receiving a second rhythm produced by the nervous system of the subject at each of a second plurality of time periods after the therapy intervention, the second rhythm comprising one or more waveforms produced by the one or more wearable sensors, the second rhythm is associated with a time period of the second plurality of time periods;
receiving one or more physical characteristics values of the subject, the one or more physical characteristics values are each associated with the time period of the second plurality of time periods after the therapy intervention, on which measurements of the one or more physical characteristics values were taken;
estimating trajectories of fluctuations of the second rhythm over the plurality of time periods for the second rhythm;
generating a digital representation that represents the estimated trajectories against a change in one of the physical characteristics values between each two successive time periods over the plurality of time periods for the second rhythm;
performing a fitting for the digital representation to determine a fitted curve;
using the fitted curve to identify whether the subject has a normal neuro-development or has a risk of neuro-development disorder;
comparing an outcome of tracking the neuro-development disorder before and after the therapy intervention is complete to generate a comparison result; and
outputting the comparison result.

18. The system of claim 1, wherein the programming instructions are further configured to, after using the fitted curve to identify whether the subject has a normal neuro-development or has a risk of neuro-development disorder, re-track neuro-development disorder in the subject, after a medication intake, by:
receiving a second rhythm produced by the nervous system of the subject at each of a second plurality of time periods after the medication intake, the second rhythm comprising one or more waveforms produced by the one or more wearable sensors, the second rhythm is associated with a time period of the second plurality of time periods;
receiving one or more physical characteristics values of the subject, the one or more physical characteristics values are each associated with the time period of the second plurality of time periods after the medication intake, on which measurements of the one or more physical characteristics values were taken;
estimating trajectories of fluctuations of the second rhythm over the plurality of time periods for the second rhythm;
generating a digital representation that represents the estimated trajectories against a change in one of the physical characteristics values between each two successive time periods over the plurality of time periods for the second rhythm;
performing a fitting for the digital representation to determine a fitted curve;
using the fitted curve to identify whether the subject has a normal neuro-development or has a risk of neuro-development disorder;
comparing an outcome of tracking the neuro-development disorder before and after the medication intake to generate a comparison result; and
outputting the comparison result.

19. A method for tracking neuro-development disorder in a subject, comprising:
capturing, by one or more wearable sensors attached to a subject, at each of a plurality of time periods:
a rhythm produced by a nervous system of the subject, the rhythm comprising one or more waveforms produced by the one or more wearable sensors, each rhythm is associated with the time period, and
one or more physical characteristics values of the subject, the one or more physical characteristics values are each associated with the time period on which measurements of the one or more physical characteristics values were taken;
estimating, by a processor, trajectories of fluctuations of the rhythm over the plurality of time periods;

generating, by the processor, a digital representation that represents the estimated trajectories against a change in one of the physical characteristics values between each two successive time periods over the plurality of time periods;
performing, by the processor, a fitting for the digital representation to determine a fitted curve; and
using the fitted curve to identify whether the subject has a normal neuro-development or has a risk of neuro-development disorder.

* * * * *